US011142544B2

(12) United States Patent
Liu et al.

(10) Patent No.: US 11,142,544 B2
(45) Date of Patent: Oct. 12, 2021

(54) PHOSPHOROTHIOATE DNAZYME COMPLEXES AND USE THEREOF

(71) Applicants: Juewen Liu, Kitchener (CA); Po-Jung Jimmy Huang, Taipei (TW)

(72) Inventors: Juewen Liu, Kitchener (CA); Po-Jung Jimmy Huang, Taipei (TW)

(*) Notice: Subject to any disclaimer, the term of this patent is extended or adjusted under 35 U.S.C. 154(b) by 109 days.

(21) Appl. No.: 15/307,499

(22) PCT Filed: Apr. 28, 2015

(86) PCT No.: PCT/CA2015/000292
§ 371 (c)(1),
(2) Date: Oct. 28, 2016

(87) PCT Pub. No.: WO2015/164957
PCT Pub. Date: Nov. 5, 2015

(65) Prior Publication Data
US 2017/0241971 A1 Aug. 24, 2017

Related U.S. Application Data

(60) Provisional application No. 62/177,018, filed on Mar. 4, 2015, provisional application No. 61/996,034, filed on Apr. 28, 2014.

(51) Int. Cl.
C12Q 1/68 (2018.01)
C07H 21/04 (2006.01)
C12N 15/11 (2006.01)
C12N 15/10 (2006.01)

(52) U.S. Cl.
CPC .......... C07H 21/04 (2013.01); C12N 15/10 (2013.01); C12N 15/111 (2013.01); C12Q 1/68 (2013.01); C12N 2310/127 (2013.01); C12N 2310/315 (2013.01); C12N 2310/3519 (2013.01); C12N 2310/531 (2013.01); C12N 2320/10 (2013.01)

(58) Field of Classification Search
None
See application file for complete search history.

(56) References Cited

U.S. PATENT DOCUMENTS

| | | | |
|---|---|---|---|
| 6,630,306 B1 * | 10/2003 | Breaker | C12N 15/101 435/196 |
| 6,706,474 B1 | 3/2004 | Lu et al. | |
| 6,890,719 B2 | 5/2005 | Lu et al. | |
| 7,192,708 B2 | 3/2007 | Lu et al. | |
| 7,332,283 B2 | 2/2008 | Lu et al. | |
| 7,612,185 B2 | 11/2009 | Lu et al. | |
| 7,902,353 B2 | 3/2011 | Lu et al. | |
| 7,906,320 B2 | 3/2011 | Lu et al. | |
| 8,043,802 B2 | 10/2011 | Lu et al. | |
| 8,206,915 B2 | 6/2012 | Lu et al. | |

FOREIGN PATENT DOCUMENTS

| | | |
|---|---|---|
| WO | 2005100602 A2 | 10/2005 |
| WO | 2009045632 A2 | 4/2009 |
| WO | 2015164957 A1 | 11/2015 |

OTHER PUBLICATIONS

Xu et al., "MRI Biosensor for Lead Detection Based on the DNAzyme-Induced Catalytic Reaction," The Journal of Physical Chemistry B, 117, 14367-14371. (Year: 2013).*
"Catalyst", Merriam-Webster.com; accessed Oct. 29, 2018. (Year: 2018).*
Schubert et al., "RNA cleaving '10-23' DNAzymes with enhanced stability and activity", Nucleic Acids Research, vol. 31, No. 20, 5982-5992. (Year: 2003).*
Huang, P-J. J. et al. "A new heavy lanthanide-dependent DNAzyme displaying strong metal cooperativity and unrescuable phosphorothioate effect." Nucleic Acids Res., vol. 43, No. 1, pp. 461-469, Jan. 2015.
Breaker, R.R., et al., "A DNA enzyme that cleaves RNA." Chem Biol., vol. 1, No. 4, pp. 223-229, Dec. 1994.
Schubert, S., et al., "RNA cleaving '10-23' DNAzymes with enhanced stability and activity." Nucleic Acids Res. vol. 31, No. 20, pp. 5982-5992, Oct. 2003.
Huang, P.-J. J. and Liu, J., "Sensing parts-per-trillion Cd(2+), Hg(2+), and Pb(2+) collectively and individually using phosphorothioate DNAzymes." Anal Chem, vol. 86, No. 12, pp. 5999-6005, Jun. 2014.
International Search Report and Written Opinion for PCT/CA2015/000292 dated Aug. 5, 2015.

* cited by examiner

Primary Examiner — Bradley L. Sisson
(74) Attorney, Agent, or Firm — Susan Tandan; Gowling WLG (Canada) LLP

(57) ABSTRACT

A novel substrate-bound DNAzyme complex is provided comprising a DNAzyme bound to a nucleic acid-based substrate. The DNAzyme comprises a pair of binding arms which hybridize to binding regions on the substrate, and a catalytic domain between the binding arms. The nucleic acid-based substrate comprises a phosphorothioate-modified ribonucleotide cleavage site between the binding regions of the substrate. The catalytic domain of the DNAzyme catalyzes heavy metal-dependent cleavage of the substrate cleavage site. The DNAzyme complex is useful in a method of heavy metal sensing. A novel cadmium-selective DNAzyme is also described for cadmium sensing.

12 Claims, 19 Drawing Sheets

Specification includes a Sequence Listing.

PO: AGGTCAAAGGTGGGTG
1:  A*GGTCAAAGGTGGGTG
2:  AG*GTCAAAGGTGGGTG
3:  AGG*TCAAAGGTGGGTG
4:  AGGT*CAAAGGTGGGTG
5:  AGGTC*AAAGGTGGGTG
6:  AGGTCA*AAGGTGGGTG
7:  AGGTCAA*AGGTGGGTG
8:  AGGTCAAA*GGTGGGTG
9:  AGGTCAAAG*GTGGGTG
10: AGGTCAAAGG*TGGGTG
11: AGGTCAAAGGT*GGGTG
12: AGGTCAAAGGTG*GGTG
13: AGGTCAAAGGTGG*GTG
14: AGGTCAAAGGTGGG*TG
15: AGGTCAAAGGTGGGT*G
FIG. 3A
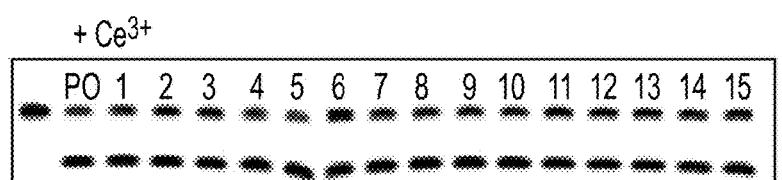
FIG. 3B
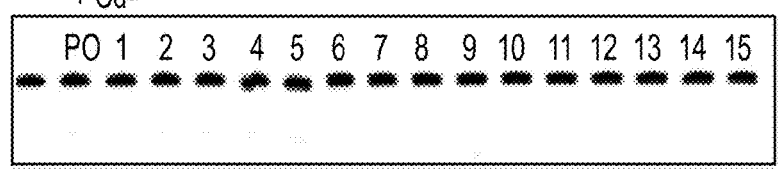
FIG. 3C
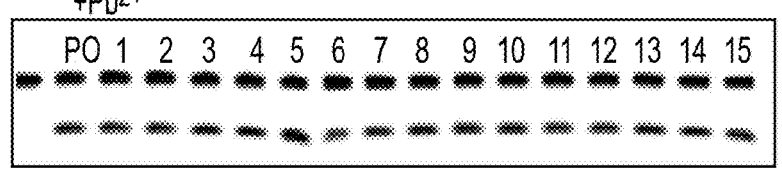
FIG. 3D

| | |
|---|---|
| TCGATAGTTAAA | (16, 19) |
| TCGATAGTTAAG | (22, 33) |
| TCGATAGTTGAA | (5, 8) |
| TCGATAGTTGAG | (15, 29) |
| TCGATAGCTAAG | (9, 24, 34) |
| TCGATAGCCCAG | (17, 23) |
| TCGATAGCACAA | (25) |
| TCGATAGCTCAA | (26) |
| TCGACAGCCCAG | (11) |
| TCGACAGTAGAG | (7, 12, 35) |

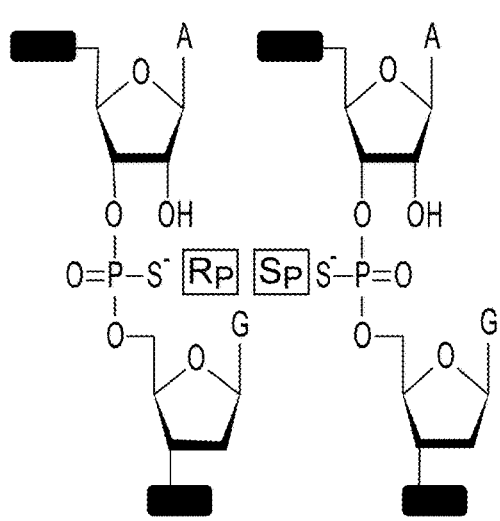
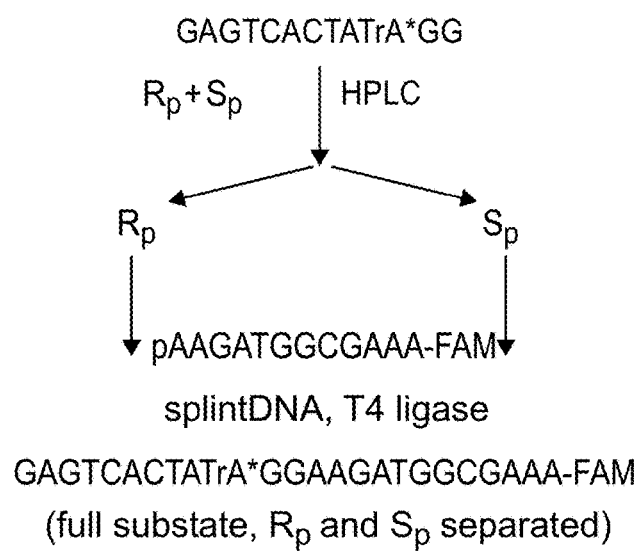
FIG. 11A
FIG. 11B
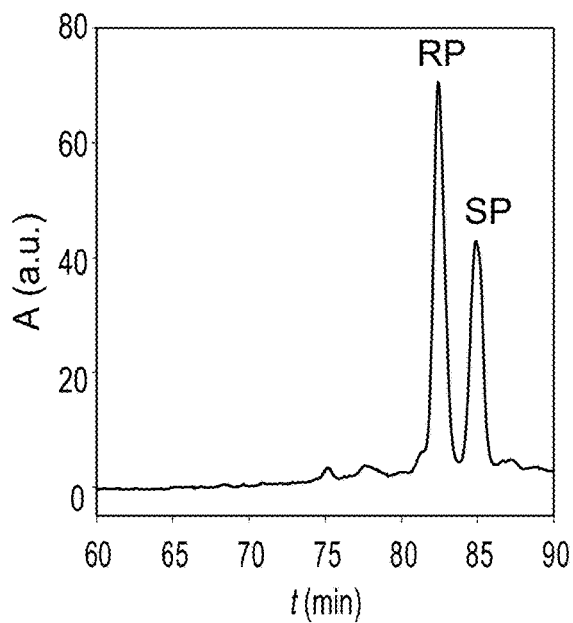
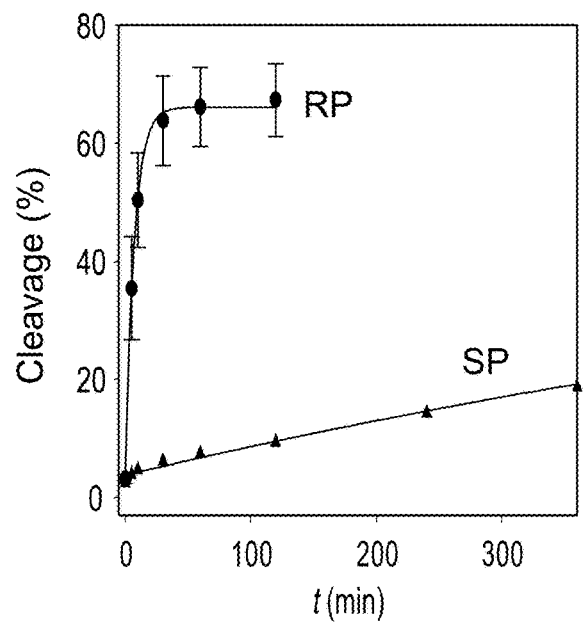
FIG. 11C
FIG. 11D

SEQUENCE LISTING

<160> NUMBER OF SEQ ID NOS: 188

<210> SEQ ID NO 1
<211> LENGTH: 32
<212> TYPE: DNA
<213> ORGANISM: Artificial
<220> FEATURE:
<223> OTHER INFORMATION: substrate

<400> SEQUENCE: 1
cgttcgcctc atgacgttga aggatccaga ct        32

<210> SEQ ID NO 2
<211> LENGTH: 30
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (15)..(16)
<223> OTHER INFORMATION: phosphorothioate linkage

<400> SEQUENCE: 2
gtcacgagtc actataggaa gatggcgaaa        30

```
<210> SEQ ID NO 3
<211> LENGTH: 30
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (16)..(17)
<223> OTHER INFORMATION: phosphorothioate linkage

<400> SEQUENCE: 3
gtcacgagtc actataggaa gatggcgaaa                                   30

<210> SEQ ID NO 4
<211> LENGTH: 30
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (15)..(17)
<223> OTHER INFORMATION: phosphorothioate linkages between T(15), A(16)
      and G(17)

<400> SEQUENCE: 4
gtcacgagtc actataggaa gatggcgaaa                                   30

<210> SEQ ID NO 5
<211> LENGTH: 56
<212> TYPE: DNA
<213> ORGANISM: Artificial
<220> FEATURE:
<223> OTHER INFORMATION: DNAzyme

<400> SEQUENCE: 5
tttcgccata ggtcaaaggt gggtgcgagt ttttactcgt tatagtgact cgtgac      56

<210> SEQ ID NO 6
<211> LENGTH: 40
<212> TYPE: DNA
<213> ORGANISM: Artificial
<220> FEATURE:
<223> OTHER INFORMATION: DNAzyme

<400> SEQUENCE: 6
cgccatcttc tccgagccgg tcgaaatagt gactcgtgac                        40

<210> SEQ ID NO 7
<211> LENGTH: 42
<212> TYPE: DNA
<213> ORGANISM: Artificial
<220> FEATURE:
<223> OTHER INFORMATION: DNAzyme

<400> SEQUENCE: 7
tttcgccatc tgaagtagcg ccgccgtata gtgactcgtg ac                     42

<210> SEQ ID NO 8
<211> LENGTH: 51
<212> TYPE: DNA
<213> ORGANISM: Artificial
<220> FEATURE:
<223> OTHER INFORMATION: DNAzyme

<400> SEQUENCE: 8
tttcgccatc ttcagttcgg aaacgaacct tcagacatag tgactcgtga c           51
```

<210> SEQ ID NO 9
<211> LENGTH: 57
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (1)..(1)
<223> OTHER INFORMATION: nucleotide at position 1 is labelled with a
      carboxyfluoroscein label
<220> FEATURE:
<221> NAME/KEY: misc_feature
<222> LOCATION: (1)..(1)
<223> OTHER INFORMATION: r is a carboxyfluoroscein label

<400> SEQUENCE: 9
rtttcgccat aggtcaaagg tgggtgcgag tttttactcg ttatagtgac tcgtgac    57

<210> SEQ ID NO 10
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (1)..(1)
<223> OTHER INFORMATION: nucleotide at position 1 is labelled with a
      carboxyfluoroscein label
<220> FEATURE:
<221> NAME/KEY: misc_feature
<222> LOCATION: (1)..(1)
<223> OTHER INFORMATION: r is a carboxyfluoroscein label

<400> SEQUENCE: 10
tttcgccata ggtcaaaggt gggtgcgagt ttttactcgt tatagtgact cgtgac    56

<210> SEQ ID NO 11
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (10)..(11)
<223> OTHER INFORMATION: phosphorothioate linkage

<400> SEQUENCE: 11
tttcgccata ggtcaaaggt gggtgcgagt ttttactcgt tatagtgact cgtgac    56

<210> SEQ ID NO 12
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (11)..(12)
<223> OTHER INFORMATION: phosphorothioate linkage

<400> SEQUENCE: 12
tttcgccata ggtcaaaggt gggtgcgagt ttttactcgt tatagtgact cgtgac    56

<210> SEQ ID NO 13
<211> LENGTH: 56
<212> TYPE: DNA

-continued

```
<213> ORGANISM: Artificial
<220> FEATURE:
<223> OTHER INFORMATION: DNAzyme
<220> FEATURE:
<221> NAME/KEY: misc_feature
<222> LOCATION: (12)..(13)
<223> OTHER INFORMATION: phosphorothioate linkage

<400> SEQUENCE: 13
tttcgccata ggtcaaaggt gggtgcgagt ttttactcgt tatagtgact cgtgac      56

<210> SEQ ID NO 14
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (13)..(14)
<223> OTHER INFORMATION: phosphorothioate linkage

<400> SEQUENCE: 14
tttcgccata ggtcaaaggt gggtgcgagt ttttactcgt tatagtgact cgtgac      56

<210> SEQ ID NO 15
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (14)..(15)
<223> OTHER INFORMATION: phosphorothioate linkage

<400> SEQUENCE: 15
tttcgccata ggtcaaaggt gggtgcgagt ttttactcgt tatagtgact cgtgac      56

<210> SEQ ID NO 16
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (15)..(16)
<223> OTHER INFORMATION: phosphorothioate linkage

<400> SEQUENCE: 16
tttcgccata ggtcaaaggt gggtgcgagt ttttactcgt tatagtgact cgtgac      56

<210> SEQ ID NO 17
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (16)..(17)
<223> OTHER INFORMATION: phosphorothioate linkage

<400> SEQUENCE: 17
tttcgccata ggtcaaaggt gggtgcgagt ttttactcgt tatagtgact cgtgac      56

<210> SEQ ID NO 18
<211> LENGTH: 56
```

```
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (17)..(18)
<223> OTHER INFORMATION: phosphorothioate linkage

<400> SEQUENCE: 18
tttcgccata ggtcaaaggt gggtgcgagt ttttactcgt tatagtgact cgtgac      56

<210> SEQ ID NO 19
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (18)..(19)
<223> OTHER INFORMATION: phosphorothioate linkage

<400> SEQUENCE: 19
tttcgccata ggtcaaaggt gggtgcgagt ttttactcgt tatagtgact cgtgac      56

<210> SEQ ID NO 20
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (19)..(20)
<223> OTHER INFORMATION: phosphorothioate linkage

<400> SEQUENCE: 20
tttcgccata ggtcaaaggt gggtgcgagt ttttactcgt tatagtgact cgtgac      56

<210> SEQ ID NO 21
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (20)..(21)
<223> OTHER INFORMATION: phosphorothioate linkage

<400> SEQUENCE: 21
tttcgccata ggtcaaaggt gggtgcgagt ttttactcgt tatagtgact cgtgac      56

<210> SEQ ID NO 22
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (21)..(22)
<223> OTHER INFORMATION: phosphorothioate linkage

<400> SEQUENCE: 22
tttcgccata ggtcaaaggt gggtgcgagt ttttactcgt tatagtgact cgtgac      56

<210> SEQ ID NO 23
```

```
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (22)..(23)
<223> OTHER INFORMATION: phosphorothioate linkage

<400> SEQUENCE: 23
tttcgccata ggtcaaaggt gggtgcgagt ttttactcgt tatagtgact cgtgac      56

<210> SEQ ID NO 24
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (23)..(24)
<223> OTHER INFORMATION: phosphorothioate linkage

<400> SEQUENCE: 24
tttcgccata ggtcaaaggt gggtgcgagt ttttactcgt tatagtgact cgtgac      56

<210> SEQ ID NO 25
<211> LENGTH: 56
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (24)..(25)
<223> OTHER INFORMATION: phosphorothioate linkage

<400> SEQUENCE: 25
tttcgccata ggtcaaaggt gggtgcgagt ttttactcgt tatagtgact cgtgac      56

<210> SEQ ID NO 26
<211> LENGTH: 35
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (14)..(64)
<223> OTHER INFORMATION: N may be a chain of up to 50 nucleotides

<400> SEQUENCE: 26
ggcgaaacat cttntagtga cggtaagctt ggcac                             35

<210> SEQ ID NO 27
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(17)
<223> OTHER INFORMATION: phosphorothioate linkage

<400> SEQUENCE: 27
aatacgagtc actataggaa gat                                          23
```

-continued

```
<210> SEQ ID NO 28
<211> LENGTH: 35
<212> TYPE: DNA
<213> ORGANISM: Artificial
<220> FEATURE:
<223> OTHER INFORMATION: splint DNA

<400> SEQUENCE: 28
aagatgtttc gccatcttcc tatagtccac cacca                              35

<210> SEQ ID NO 29
<211> LENGTH: 15
<212> TYPE: DNA
<213> ORGANISM: Artificial
<220> FEATURE:
<223> OTHER INFORMATION: primer

<400> SEQUENCE: 29
gtgccaagct taccg                                                    15

<210> SEQ ID NO 30
<211> LENGTH: 44
<212> TYPE: DNA
<213> ORGANISM: Artificial
<220> FEATURE:
<223> OTHER INFORMATION: primer

<400> SEQUENCE: 30
ctgcagaatt ctaatacgag tcactatagg aagatggcga aaca                    44

<210> SEQ ID NO 31
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (28)..(29)
<223> OTHER INFORMATION: phosphorothioate linkage

<400> SEQUENCE: 31
aaatgatcca ctaatacgac tcactatagg                                    30

<210> SEQ ID NO 32
<211> LENGTH: 28
<212> TYPE: DNA
<213> ORGANISM: Artificial
<220> FEATURE:
<223> OTHER INFORMATION: primer
<220> FEATURE:
<221> NAME/KEY: misc_feature
<223> OTHER INFORMATION: r is an 18-atom hexa-ethyleneglycol spacer
<220> FEATURE:
<221> NAME/KEY: misc_feature
<222> LOCATION: (13)..(31)
<223> OTHER INFORMATION: sp is an 18-atom hexa-ethyleneglycol spacer
<220> FEATURE:
<221> NAME/KEY: misc_feature
<222> LOCATION: (13)..(13)
<223> OTHER INFORMATION: sp is an 18-atom hexa-ethyleneglycol spacer

<400> SEQUENCE: 32
aacaacaaca acrgtgccaa gcttaccg                                      28

<210> SEQ ID NO 33
<211> LENGTH: 22
<212> TYPE: DNA
<213> ORGANISM: Artificial
```

```
<220> FEATURE:
<223> OTHER INFORMATION: blocking DNA

<400> SEQUENCE: 33
cgcacctacc tttgacctat gg                                              22

<210> SEQ ID NO 34
<211> LENGTH: 22
<212> TYPE: DNA
<213> ORGANISM: Artificial
<220> FEATURE:
<223> OTHER INFORMATION: blocking DNA

<400> SEQUENCE: 34
cgcacccacc tttgacctat gg                                              22

<210> SEQ ID NO 35
<211> LENGTH: 60
<212> TYPE: DNA
<213> ORGANISM: Artificial
<220> FEATURE:
<223> OTHER INFORMATION: DNAzyme

<400> SEQUENCE: 35
cgccatcttc aattcgatag agtccacgtc tacaggaatg tgggaaatag tgactcgtga     60

<210> SEQ ID NO 36
<211> LENGTH: 42
<212> TYPE: DNA
<213> ORGANISM: Artificial
<220> FEATURE:
<223> OTHER INFORMATION: DNAzyme

<400> SEQUENCE: 36
tttcgccatc ttccttcgac agcccagata gtgactcgtg ac                       42

<210> SEQ ID NO 37
<211> LENGTH: 42
<212> TYPE: DNA
<213> ORGANISM: Artificial
<220> FEATURE:
<223> OTHER INFORMATION: DNAzyme

<400> SEQUENCE: 37
tttcgccatc ttccttcgat agttaaaata gtgactcgtg ac                       42

<210> SEQ ID NO 38
<211> LENGTH: 42
<212> TYPE: DNA
<213> ORGANISM: Artificial
<220> FEATURE:
<223> OTHER INFORMATION: DNAzyme

<400> SEQUENCE: 38
tttcgccatc ttccttcgat agcccagata gtgactcgtg ac                       42

<210> SEQ ID NO 39
<211> LENGTH: 42
<212> TYPE: DNA
<213> ORGANISM: Artificial
<220> FEATURE:
<223> OTHER INFORMATION: DNAzyme

<400> SEQUENCE: 39
tttcgccatc tttccttcgat agttaagata gtgactcgtg ac                      42
```

```
<210> SEQ ID NO 40
<211> LENGTH: 41
<212> TYPE: DNA
<213> ORGANISM: Artificial
<220> FEATURE:
<223> OTHER INFORMATION: DNAzyme

<400> SEQUENCE: 40
tttcgccatc ttgaaacgca cgaagaatag tgactcgtga c                              41

<210> SEQ ID NO 41
<211> LENGTH: 39
<212> TYPE: DNA
<213> ORGANISM: Artificial
<220> FEATURE:
<223> OTHER INFORMATION: DNAzyme

<400> SEQUENCE: 41
tttcgccatc taacaggaaa cactttagtg actcgtgac                                 39

<210> SEQ ID NO 42
<211> LENGTH: 60
<212> TYPE: DNA
<213> ORGANISM: Artificial
<220> FEATURE:
<223> OTHER INFORMATION: DNAzyme

<400> SEQUENCE: 42
cgccatcttt acccaaaagg aaggttttct attttagaa acacaggagt agtgactcgt           60

<210> SEQ ID NO 43
<211> LENGTH: 31
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (16)..(17)
<223> OTHER INFORMATION: phosphorothioate linkage
<220> FEATURE:
<221> NAME/KEY: misc_feature
<222> LOCATION: (31)..(31)
<223> OTHER INFORMATION: r is carboxyfluoroscein

<400> SEQUENCE: 43
gtcacgagtc actataggaa gatggcgaaa r                                         31

<210> SEQ ID NO 44
<211> LENGTH: 32
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (31)..(31)
<223> OTHER INFORMATION: r is carboxyfluoroscein

<400> SEQUENCE: 44
gtcacgagtc actatragga agatggcgaa ar                                        32

<210> SEQ ID NO 45
<211> LENGTH: 53
<212> TYPE: DNA
<213> ORGANISM: Artificial
<220> FEATURE:
<223> OTHER INFORMATION: DNAzyme
```

<400> SEQUENCE: 45
tttcgccata ggtcaaaggt gggtgcgagt ttttactcgt tatagtgact cgt        53

<210> SEQ ID NO 46
<211> LENGTH: 43
<212> TYPE: DNA
<213> ORGANISM: Artificial
<220> FEATURE:
<223> OTHER INFORMATION: DNAzyme

<400> SEQUENCE: 46
tttcgccatc ttctccgagc cggtcgaaat agtgactcgt gac                    43

<210> SEQ ID NO 47
<211> LENGTH: 25
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (1)..(1)
<223> OTHER INFORMATION: r is a carboxyfluorscein label
<220> FEATURE:
<221> NAME/KEY: misc_feature
<222> LOCATION: (11)..(12)
<223> OTHER INFORMATION: phosphorothioate linkage

<400> SEQUENCE: 47
ragtcactat aggaagatgg cgaac                                        25

<210> SEQ ID NO 48
<211> LENGTH: 36
<212> TYPE: DNA
<213> ORGANISM: Artificial
<220> FEATURE:
<223> OTHER INFORMATION: DNAzyme

<400> SEQUENCE: 48
gttcgccatc ttccttcgat agttaaaata gtgact                            36

<210> SEQ ID NO 49
<211> LENGTH: 35
<212> TYPE: DNA
<213> ORGANISM: Artificial
<220> FEATURE:
<223> OTHER INFORMATION: DNA splint

<400> SEQUENCE: 49
aaaaaaaaaa tttcgccatc ttcctatagt gactc                             35

<210> SEQ ID NO 50
<211> LENGTH: 13
<212> TYPE: DNA
<213> ORGANISM: Artificial
<220> FEATURE:
<223> OTHER INFORMATION: primer

<400> SEQUENCE: 50
gagtcactat agg                                                     13

<210> SEQ ID NO 51
<211> LENGTH: 12
<212> TYPE: DNA
<213> ORGANISM: Artificial
<220> FEATURE:

<223> OTHER INFORMATION: primer

<400> SEQUENCE: 51
aagatggcga aa                                                            12

<210> SEQ ID NO 52
<211> LENGTH: 12
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (5)..(5)
<223> OTHER INFORMATION: N may be T or C
<220> FEATURE:
<221> NAME/KEY: misc_feature
<222> LOCATION: (8)..(8)
<223> OTHER INFORMATION: N may be T or C
<220> FEATURE:
<221> NAME/KEY: misc_feature
<222> LOCATION: (9)..(10)
<223> OTHER INFORMATION: N may be A, T, G or C
<220> FEATURE:
<221> NAME/KEY: misc_feature
<222> LOCATION: (12)..(12)
<223> OTHER INFORMATION: N may be A or G

<400> SEQUENCE: 52
tcganagnnn an                                                            12

<210> SEQ ID NO 53
<211> LENGTH: 12
<212> TYPE: DNA
<213> ORGANISM: Artificial
<220> FEATURE:
<223> OTHER INFORMATION: DNAzyme

<400> SEQUENCE: 53
tcgatagtaa aa                                                            12

<210> SEQ ID NO 54
<211> LENGTH: 12
<212> TYPE: DNA
<213> ORGANISM: Artificial
<220> FEATURE:
<223> OTHER INFORMATION: DNAzyme

<400> SEQUENCE: 54
tcgatagtat aa                                                            12

<210> SEQ ID NO 55
<211> LENGTH: 12
<212> TYPE: DNA
<213> ORGANISM: Artificial
<220> FEATURE:
<223> OTHER INFORMATION: DNAzyme

<400> SEQUENCE: 55
tcgatagtag aa                                                            12

<210> SEQ ID NO 56
<211> LENGTH: 12
<212> TYPE: DNA
<213> ORGANISM: Artificial
<220> FEATURE:
<223> OTHER INFORMATION: DNAzyme

<400> SEQUENCE: 56
tcgatagtac aa                                                          12

<210> SEQ ID NO 57
<211> LENGTH: 12
<212> TYPE: DNA
<213> ORGANISM: Artificial
<220> FEATURE:
<223> OTHER INFORMATION: DNAzyme

<400> SEQUENCE: 57
tcgatagttt aa                                                          12

<210> SEQ ID NO 58
<211> LENGTH: 12
<212> TYPE: DNA
<213> ORGANISM: Artificial
<220> FEATURE:
<223> OTHER INFORMATION: DNAzyme

<400> SEQUENCE: 58
tcgatagtta aa                                                          12

<210> SEQ ID NO 59
<211> LENGTH: 12
<212> TYPE: DNA
<213> ORGANISM: Artificial
<220> FEATURE:
<223> OTHER INFORMATION: DNAzyme

<400> SEQUENCE: 59
tcgatagttc aa                                                          12

<210> SEQ ID NO 60
<211> LENGTH: 12
<212> TYPE: DNA
<213> ORGANISM: Artificial
<220> FEATURE:
<223> OTHER INFORMATION: DNAzyme

<400> SEQUENCE: 60
tcgatagttg aa                                                          12

<210> SEQ ID NO 61
<211> LENGTH: 12
<212> TYPE: DNA
<213> ORGANISM: Artificial
<220> FEATURE:
<223> OTHER INFORMATION: DNAzyme

<400> SEQUENCE: 61
tcgatagtgg aa                                                          12

<210> SEQ ID NO 62
<211> LENGTH: 12
<212> TYPE: DNA
<213> ORGANISM: Artificial
<220> FEATURE:
<223> OTHER INFORMATION: DNAzyme

<400> SEQUENCE: 62
tcgatagtga aa                                                          12

<210> SEQ ID NO 63
<211> LENGTH: 12
<212> TYPE: DNA

```
<213> ORGANISM: Artificial
<220> FEATURE:
<223> OTHER INFORMATION: DNAzyme

<400> SEQUENCE: 63
tcgatagtgt aa                                                             12

<210> SEQ ID NO 64
<211> LENGTH: 12
<212> TYPE: DNA
<213> ORGANISM: Artificial
<220> FEATURE:
<223> OTHER INFORMATION: DNAzyme

<400> SEQUENCE: 64
tcgatagtgc aa                                                             12

<210> SEQ ID NO 65
<211> LENGTH: 12
<212> TYPE: DNA
<213> ORGANISM: Artificial
<220> FEATURE:
<223> OTHER INFORMATION: DNAzyme

<400> SEQUENCE: 65
tcgatagtcc aa                                                             12

<210> SEQ ID NO 66
<211> LENGTH: 12
<212> TYPE: DNA
<213> ORGANISM: Artificial
<220> FEATURE:
<223> OTHER INFORMATION: DNAzyme

<400> SEQUENCE: 66
tcgatagtca aa                                                             12

<210> SEQ ID NO 67
<211> LENGTH: 12
<212> TYPE: DNA
<213> ORGANISM: Artificial
<220> FEATURE:
<223> OTHER INFORMATION: DNAzyme

<400> SEQUENCE: 67
tcgatagtct aa                                                             12

<210> SEQ ID NO 68
<211> LENGTH: 12
<212> TYPE: DNA
<213> ORGANISM: Artificial
<220> FEATURE:
<223> OTHER INFORMATION: DNAzyme

<400> SEQUENCE: 68
tcgatagtcg aa                                                             12

<210> SEQ ID NO 69
<211> LENGTH: 12
<212> TYPE: DNA
<213> ORGANISM: Artificial
<220> FEATURE:
<223> OTHER INFORMATION: DNAzyme

<400> SEQUENCE: 69
tcgatagtaa ag                                                             12
```

```
<210> SEQ ID NO 70
<211> LENGTH: 12
<212> TYPE: DNA
<213> ORGANISM: Artificial
<220> FEATURE:
<223> OTHER INFORMATION: DNAzyme

<400> SEQUENCE: 70
tcgatagtat ag                                                          12

<210> SEQ ID NO 71
<211> LENGTH: 12
<212> TYPE: DNA
<213> ORGANISM: Artificial
<220> FEATURE:
<223> OTHER INFORMATION: DNAzyme

<400> SEQUENCE: 71
tcgatagtag ag                                                          12

<210> SEQ ID NO 72
<211> LENGTH: 12
<212> TYPE: DNA
<213> ORGANISM: Artificial
<220> FEATURE:
<223> OTHER INFORMATION: DNAzyme

<400> SEQUENCE: 72
tcgatagtac ag                                                          12

<210> SEQ ID NO 73
<211> LENGTH: 12
<212> TYPE: DNA
<213> ORGANISM: Artificial
<220> FEATURE:
<223> OTHER INFORMATION: DNAzyme

<400> SEQUENCE: 73
tcgatagttt ag                                                          12

<210> SEQ ID NO 74
<211> LENGTH: 12
<212> TYPE: DNA
<213> ORGANISM: Artificial
<220> FEATURE:
<223> OTHER INFORMATION: DNAzyme

<400> SEQUENCE: 74
tcgatagtta ag                                                          12

<210> SEQ ID NO 75
<211> LENGTH: 12
<212> TYPE: DNA
<213> ORGANISM: Artificial
<220> FEATURE:
<223> OTHER INFORMATION: DNAzyme

<400> SEQUENCE: 75
tcgatagttc ag                                                          12

<210> SEQ ID NO 76
<211> LENGTH: 12
<212> TYPE: DNA
<213> ORGANISM: Artificial
<220> FEATURE:
```

```
<223> OTHER INFORMATION: DNAzyme

<400> SEQUENCE: 76
tcgatagttg ag                                                            12

<210> SEQ ID NO 77
<211> LENGTH: 12
<212> TYPE: DNA
<213> ORGANISM: Artificial
<220> FEATURE:
<223> OTHER INFORMATION: DNAzyme

<400> SEQUENCE: 77
tcgatagtgg ag                                                            12

<210> SEQ ID NO 78
<211> LENGTH: 12
<212> TYPE: DNA
<213> ORGANISM: Artificial
<220> FEATURE:
<223> OTHER INFORMATION: DNAzyme

<400> SEQUENCE: 78
tcgatagtga ag                                                            12

<210> SEQ ID NO 79
<211> LENGTH: 12
<212> TYPE: DNA
<213> ORGANISM: Artificial
<220> FEATURE:
<223> OTHER INFORMATION: DNAzyme

<400> SEQUENCE: 79
tcgatagtgt ag                                                            12

<210> SEQ ID NO 80
<211> LENGTH: 12
<212> TYPE: DNA
<213> ORGANISM: Artificial
<220> FEATURE:
<223> OTHER INFORMATION: DNAzyme

<400> SEQUENCE: 80
tcgatagtgc ag                                                            12

<210> SEQ ID NO 81
<211> LENGTH: 12
<212> TYPE: DNA
<213> ORGANISM: Artificial
<220> FEATURE:
<223> OTHER INFORMATION: DNAzyme

<400> SEQUENCE: 81
tcgatagtcc ag                                                            12

<210> SEQ ID NO 82
<211> LENGTH: 12
<212> TYPE: DNA
<213> ORGANISM: Artificial
<220> FEATURE:
<223> OTHER INFORMATION: DNAzyme

<400> SEQUENCE: 82
tcgatagtca ag                                                            12
```

```
<210> SEQ ID NO 83
<211> LENGTH: 12
<212> TYPE: DNA
<213> ORGANISM: Artificial
<220> FEATURE:
<223> OTHER INFORMATION: DNAzyme

<400> SEQUENCE: 83
tcgatagtct ag                                                          12

<210> SEQ ID NO 84
<211> LENGTH: 12
<212> TYPE: DNA
<213> ORGANISM: Artificial
<220> FEATURE:
<223> OTHER INFORMATION: DNAzyme

<400> SEQUENCE: 84
tcgatagtcg ag                                                          12

<210> SEQ ID NO 85
<211> LENGTH: 12
<212> TYPE: DNA
<213> ORGANISM: Artificial
<220> FEATURE:
<223> OTHER INFORMATION: DNAzyme

<400> SEQUENCE: 85
tcgacagcaa aa                                                          12

<210> SEQ ID NO 86
<211> LENGTH: 12
<212> TYPE: DNA
<213> ORGANISM: Artificial
<220> FEATURE:
<223> OTHER INFORMATION: DNAzyme

<400> SEQUENCE: 86
tcgacagcat aa                                                          12

<210> SEQ ID NO 87
<211> LENGTH: 12
<212> TYPE: DNA
<213> ORGANISM: Artificial
<220> FEATURE:
<223> OTHER INFORMATION: DNAzyme

<400> SEQUENCE: 87
tcgacagcag aa                                                          12

<210> SEQ ID NO 88
<211> LENGTH: 12
<212> TYPE: DNA
<213> ORGANISM: Artificial
<220> FEATURE:
<223> OTHER INFORMATION: DNAzyme

<400> SEQUENCE: 88
tcgacagcac aa                                                          12

<210> SEQ ID NO 89
<211> LENGTH: 12
<212> TYPE: DNA
<213> ORGANISM: Artificial
<220> FEATURE:
<223> OTHER INFORMATION: DNAzyme
```

```
<400> SEQUENCE: 89
tcgacagctt aa                                                    12

<210> SEQ ID NO 90
<211> LENGTH: 12
<212> TYPE: DNA
<213> ORGANISM: Artificial
<220> FEATURE:
<223> OTHER INFORMATION: DNAzyme

<400> SEQUENCE: 90
tcgacagcta aa                                                    12

<210> SEQ ID NO 91
<211> LENGTH: 12
<212> TYPE: DNA
<213> ORGANISM: Artificial
<220> FEATURE:
<223> OTHER INFORMATION: DNAzyme

<400> SEQUENCE: 91
tcgacagctc aa                                                    12

<210> SEQ ID NO 92
<211> LENGTH: 12
<212> TYPE: DNA
<213> ORGANISM: Artificial
<220> FEATURE:
<223> OTHER INFORMATION: DNAzyme

<400> SEQUENCE: 92
tcgacagctg aa                                                    12

<210> SEQ ID NO 93
<211> LENGTH: 12
<212> TYPE: DNA
<213> ORGANISM: Artificial
<220> FEATURE:
<223> OTHER INFORMATION: DNAzyme

<400> SEQUENCE: 93
tcgacagcgg aa                                                    12

<210> SEQ ID NO 94
<211> LENGTH: 12
<212> TYPE: DNA
<213> ORGANISM: Artificial
<220> FEATURE:
<223> OTHER INFORMATION: DNAzyme

<400> SEQUENCE: 94
tcgacagcga aa                                                    12

<210> SEQ ID NO 95
<211> LENGTH: 12
<212> TYPE: DNA
<213> ORGANISM: Artificial
<220> FEATURE:
<223> OTHER INFORMATION: DNAzyme

<400> SEQUENCE: 95
tcgacagcgt aa                                                    12

<210> SEQ ID NO 96
<211> LENGTH: 12
```

```
<212> TYPE: DNA
<213> ORGANISM: Artificial
<220> FEATURE:
<223> OTHER INFORMATION: DNAzyme

<400> SEQUENCE: 96
tcgacagcgc aa                                                            12

<210> SEQ ID NO 97
<211> LENGTH: 12
<212> TYPE: DNA
<213> ORGANISM: Artificial
<220> FEATURE:
<223> OTHER INFORMATION: DNAzyme

<400> SEQUENCE: 97
tcgacagccc aa                                                            12

<210> SEQ ID NO 98
<211> LENGTH: 12
<212> TYPE: DNA
<213> ORGANISM: Artificial
<220> FEATURE:
<223> OTHER INFORMATION: DNAzyme

<400> SEQUENCE: 98
tcgacagcca aa                                                            12

<210> SEQ ID NO 99
<211> LENGTH: 12
<212> TYPE: DNA
<213> ORGANISM: Artificial
<220> FEATURE:
<223> OTHER INFORMATION: DNAzyme

<400> SEQUENCE: 99
tcgacagcct aa                                                            12

<210> SEQ ID NO 100
<211> LENGTH: 12
<212> TYPE: DNA
<213> ORGANISM: Artificial
<220> FEATURE:
<223> OTHER INFORMATION: DNAzyme

<400> SEQUENCE: 100
tcgacagccg aa                                                            12

<210> SEQ ID NO 101
<211> LENGTH: 12
<212> TYPE: DNA
<213> ORGANISM: Artificial
<220> FEATURE:
<223> OTHER INFORMATION: DNAzyme

<400> SEQUENCE: 101
tcgacagcaa ag                                                            12

<210> SEQ ID NO 102
<211> LENGTH: 12
<212> TYPE: DNA
<213> ORGANISM: Artificial
<220> FEATURE:
<223> OTHER INFORMATION: DNAzyme

<400> SEQUENCE: 102
```
tcgacagcat ag                                                              12

<210> SEQ ID NO 103
<211> LENGTH: 12
<212> TYPE: DNA
<213> ORGANISM: Artificial
<220> FEATURE:
<223> OTHER INFORMATION: DNAzyme

<400> SEQUENCE: 103
tcgacagcag ag                                                              12

<210> SEQ ID NO 104
<211> LENGTH: 12
<212> TYPE: DNA
<213> ORGANISM: Artificial
<220> FEATURE:
<223> OTHER INFORMATION: DNAzyme

<400> SEQUENCE: 104
tcgacagcac ag                                                              12

<210> SEQ ID NO 105
<211> LENGTH: 12
<212> TYPE: DNA
<213> ORGANISM: Artificial
<220> FEATURE:
<223> OTHER INFORMATION: DNAzyme

<400> SEQUENCE: 105
tcgacagctt ag                                                              12

<210> SEQ ID NO 106
<211> LENGTH: 12
<212> TYPE: DNA
<213> ORGANISM: Artificial
<220> FEATURE:
<223> OTHER INFORMATION: DNAzyme

<400> SEQUENCE: 106
tcgacagcta ag                                                              12

<210> SEQ ID NO 107
<211> LENGTH: 12
<212> TYPE: DNA
<213> ORGANISM: Artificial
<220> FEATURE:
<223> OTHER INFORMATION: DNAzyme

<400> SEQUENCE: 107
tcgacagctc ag                                                              12

<210> SEQ ID NO 108
<211> LENGTH: 12
<212> TYPE: DNA
<213> ORGANISM: Artificial
<220> FEATURE:
<223> OTHER INFORMATION: DNAzyme

<400> SEQUENCE: 108
tcgacagctg ag                                                              12

<210> SEQ ID NO 109
<211> LENGTH: 12
<212> TYPE: DNA
<213> ORGANISM: Artificial

```
<220> FEATURE:
<223> OTHER INFORMATION: DNAzyme

<400> SEQUENCE: 109
tcgacagcgg ag                                                            12

<210> SEQ ID NO 110
<211> LENGTH: 12
<212> TYPE: DNA
<213> ORGANISM: Artificial
<220> FEATURE:
<223> OTHER INFORMATION: DNAzyme

<400> SEQUENCE: 110
tcgacagcga ag                                                            12

<210> SEQ ID NO 111
<211> LENGTH: 12
<212> TYPE: DNA
<213> ORGANISM: Artificial
<220> FEATURE:
<223> OTHER INFORMATION: DNAzyme

<400> SEQUENCE: 111
tcgacagcgt ag                                                            12

<210> SEQ ID NO 112
<211> LENGTH: 12
<212> TYPE: DNA
<213> ORGANISM: Artificial
<220> FEATURE:
<223> OTHER INFORMATION: DNAzyme

<400> SEQUENCE: 112
tcgacagcgc ag                                                            12

<210> SEQ ID NO 113
<211> LENGTH: 12
<212> TYPE: DNA
<213> ORGANISM: Artificial
<220> FEATURE:
<223> OTHER INFORMATION: DNAzyme

<400> SEQUENCE: 113
tcgacagccc ag                                                            12

<210> SEQ ID NO 114
<211> LENGTH: 12
<212> TYPE: DNA
<213> ORGANISM: Artificial
<220> FEATURE:
<223> OTHER INFORMATION: DNAzyme

<400> SEQUENCE: 114
tcgacagcca ag                                                            12

<210> SEQ ID NO 115
<211> LENGTH: 12
<212> TYPE: DNA
<213> ORGANISM: Artificial
<220> FEATURE:
<223> OTHER INFORMATION: DNAzyme

<400> SEQUENCE: 115
tcgacagcct ag                                                            12
```

```
<210> SEQ ID NO 116
<211> LENGTH: 12
<212> TYPE: DNA
<213> ORGANISM: Artificial
<220> FEATURE:
<223> OTHER INFORMATION: DNAzyme

<400> SEQUENCE: 116
tcgacagccg ag                                                          12

<210> SEQ ID NO 117
<211> LENGTH: 12
<212> TYPE: DNA
<213> ORGANISM: Artificial
<220> FEATURE:
<223> OTHER INFORMATION: DNAzyme

<400> SEQUENCE: 117
tcgacagtaa aa                                                          12

<210> SEQ ID NO 118
<211> LENGTH: 12
<212> TYPE: DNA
<213> ORGANISM: Artificial
<220> FEATURE:
<223> OTHER INFORMATION: DNAzyme

<400> SEQUENCE: 118
tcgacagtat aa                                                          12

<210> SEQ ID NO 119
<211> LENGTH: 12
<212> TYPE: DNA
<213> ORGANISM: Artificial
<220> FEATURE:
<223> OTHER INFORMATION: DNAzyme

<400> SEQUENCE: 119
tcgacagtag aa                                                          12

<210> SEQ ID NO 120
<211> LENGTH: 12
<212> TYPE: DNA
<213> ORGANISM: Artificial
<220> FEATURE:
<223> OTHER INFORMATION: DNAzyme

<400> SEQUENCE: 120
tcgacagtac aa                                                          12

<210> SEQ ID NO 121
<211> LENGTH: 12
<212> TYPE: DNA
<213> ORGANISM: Artificial
<220> FEATURE:
<223> OTHER INFORMATION: DNAzyme

<400> SEQUENCE: 121
tcgacagttt aa                                                          12

<210> SEQ ID NO 122
<211> LENGTH: 12
<212> TYPE: DNA
<213> ORGANISM: Artificial
<220> FEATURE:
<223> OTHER INFORMATION: DNAzyme
```

```
<400> SEQUENCE: 122
tcgacagtta aa                                                    12

<210> SEQ ID NO 123
<211> LENGTH: 12
<212> TYPE: DNA
<213> ORGANISM: Artificial
<220> FEATURE:
<223> OTHER INFORMATION: DNAzyme

<400> SEQUENCE: 123
tcgacagttc aa                                                    12

<210> SEQ ID NO 124
<211> LENGTH: 12
<212> TYPE: DNA
<213> ORGANISM: Artificial
<220> FEATURE:
<223> OTHER INFORMATION: DNAzyme

<400> SEQUENCE: 124
tcgacagttg aa                                                    12

<210> SEQ ID NO 125
<211> LENGTH: 12
<212> TYPE: DNA
<213> ORGANISM: Artificial
<220> FEATURE:
<223> OTHER INFORMATION: DNAzyme

<400> SEQUENCE: 125
tcgacagtgg aa                                                    12

<210> SEQ ID NO 126
<211> LENGTH: 12
<212> TYPE: DNA
<213> ORGANISM: Artificial
<220> FEATURE:
<223> OTHER INFORMATION: DNAzyme

<400> SEQUENCE: 126
tcgacagtga aa                                                    12

<210> SEQ ID NO 127
<211> LENGTH: 12
<212> TYPE: DNA
<213> ORGANISM: Artificial
<220> FEATURE:
<223> OTHER INFORMATION: DNAzyme

<400> SEQUENCE: 127
tcgacagtgt aa                                                    12

<210> SEQ ID NO 128
<211> LENGTH: 12
<212> TYPE: DNA
<213> ORGANISM: Artificial
<220> FEATURE:
<223> OTHER INFORMATION: DNAzyme

<400> SEQUENCE: 128
tcgacagtgc aa                                                    12

<210> SEQ ID NO 129
```

```
<211> LENGTH: 12
<212> TYPE: DNA
<213> ORGANISM: Artificial
<220> FEATURE:
<223> OTHER INFORMATION: DNAzyme

<400> SEQUENCE: 129
tcgacagtcc aa                                                     12

<210> SEQ ID NO 130
<211> LENGTH: 12
<212> TYPE: DNA
<213> ORGANISM: Artificial
<220> FEATURE:
<223> OTHER INFORMATION: DNAzyme

<400> SEQUENCE: 130
tcgacagtca aa                                                     12

<210> SEQ ID NO 131
<211> LENGTH: 12
<212> TYPE: DNA
<213> ORGANISM: Artificial
<220> FEATURE:
<223> OTHER INFORMATION: DNAzyme

<400> SEQUENCE: 131
tcgacagtct aa                                                     12

<210> SEQ ID NO 132
<211> LENGTH: 12
<212> TYPE: DNA
<213> ORGANISM: Artificial
<220> FEATURE:
<223> OTHER INFORMATION: DNAzyme

<400> SEQUENCE: 132
tcgacagtcg aa                                                     12

<210> SEQ ID NO 133
<211> LENGTH: 12
<212> TYPE: DNA
<213> ORGANISM: Artificial
<220> FEATURE:
<223> OTHER INFORMATION: DNAzyme

<400> SEQUENCE: 133
tcgacagtaa ag                                                     12

<210> SEQ ID NO 134
<211> LENGTH: 12
<212> TYPE: DNA
<213> ORGANISM: Artificial
<220> FEATURE:
<223> OTHER INFORMATION: DNAzyme

<400> SEQUENCE: 134
tcgacagtat ag                                                     12

<210> SEQ ID NO 135
<211> LENGTH: 12
<212> TYPE: DNA
<213> ORGANISM: Artificial
<220> FEATURE:
<223> OTHER INFORMATION: DNAzyme

<400> SEQUENCE: 135
```
tcgacagtag ag                                                                   12

<210> SEQ ID NO 136
<211> LENGTH: 12
<212> TYPE: DNA
<213> ORGANISM: Artificial
<220> FEATURE:
<223> OTHER INFORMATION: DNAzyme

<400> SEQUENCE: 136
tcgacagtac ag                                                                   12

<210> SEQ ID NO 137
<211> LENGTH: 12
<212> TYPE: DNA
<213> ORGANISM: Artificial
<220> FEATURE:
<223> OTHER INFORMATION: DNAzyme

<400> SEQUENCE: 137
tcgacagttt ag                                                                   12

<210> SEQ ID NO 138
<211> LENGTH: 12
<212> TYPE: DNA
<213> ORGANISM: Artificial
<220> FEATURE:
<223> OTHER INFORMATION: DNAzyme

<400> SEQUENCE: 138
tcgacagtta ag                                                                   12

<210> SEQ ID NO 139
<211> LENGTH: 12
<212> TYPE: DNA
<213> ORGANISM: Artificial
<220> FEATURE:
<223> OTHER INFORMATION: DNAzyme

<400> SEQUENCE: 139
tcgacagttc ag                                                                   12

<210> SEQ ID NO 140
<211> LENGTH: 12
<212> TYPE: DNA
<213> ORGANISM: Artificial
<220> FEATURE:
<223> OTHER INFORMATION: DNAzyme

<400> SEQUENCE: 140
tcgacagttg ag                                                                   12

<210> SEQ ID NO 141
<211> LENGTH: 12
<212> TYPE: DNA
<213> ORGANISM: Artificial
<220> FEATURE:
<223> OTHER INFORMATION: DNAzyme

<400> SEQUENCE: 141
tcgacagtgg ag                                                                   12

<210> SEQ ID NO 142
<211> LENGTH: 12
<212> TYPE: DNA

```
<213> ORGANISM: Artificial
<220> FEATURE:
<223> OTHER INFORMATION: DNAzyme

<400> SEQUENCE: 142
tcgacagtga ag                                                         12

<210> SEQ ID NO 143
<211> LENGTH: 12
<212> TYPE: DNA
<213> ORGANISM: Artificial
<220> FEATURE:
<223> OTHER INFORMATION: DNAzyme

<400> SEQUENCE: 143
tcgacagtgt ag                                                         12

<210> SEQ ID NO 144
<211> LENGTH: 12
<212> TYPE: DNA
<213> ORGANISM: Artificial
<220> FEATURE:
<223> OTHER INFORMATION: DNAzyme

<400> SEQUENCE: 144
tcgacagtgc ag                                                         12

<210> SEQ ID NO 145
<211> LENGTH: 12
<212> TYPE: DNA
<213> ORGANISM: Artificial
<220> FEATURE:
<223> OTHER INFORMATION: DNAzyme

<400> SEQUENCE: 145
tcgacagtcc ag                                                         12

<210> SEQ ID NO 146
<211> LENGTH: 12
<212> TYPE: DNA
<213> ORGANISM: Artificial
<220> FEATURE:
<223> OTHER INFORMATION: DNAzyme

<400> SEQUENCE: 146
tcgacagtca ag                                                         12

<210> SEQ ID NO 147
<211> LENGTH: 12
<212> TYPE: DNA
<213> ORGANISM: Artificial
<220> FEATURE:
<223> OTHER INFORMATION: DNAzyme

<400> SEQUENCE: 147
tcgacagtct ag                                                         12

<210> SEQ ID NO 148
<211> LENGTH: 12
<212> TYPE: DNA
<213> ORGANISM: Artificial
<220> FEATURE:
<223> OTHER INFORMATION: DNAzyme

<400> SEQUENCE: 148
tcgacagtcg ag                                                         12
```

<210> SEQ ID NO 149
<211> LENGTH: 12
<212> TYPE: DNA
<213> ORGANISM: Artificial
<220> FEATURE:
<223> OTHER INFORMATION: DNAzyme

<400> SEQUENCE: 149
tcgatagcaa aa                                                         12

<210> SEQ ID NO 150
<211> LENGTH: 12
<212> TYPE: DNA
<213> ORGANISM: Artificial
<220> FEATURE:
<223> OTHER INFORMATION: DNAzyme

<400> SEQUENCE: 150
tcgatagcat aa                                                         12

<210> SEQ ID NO 151
<211> LENGTH: 12
<212> TYPE: DNA
<213> ORGANISM: Artificial
<220> FEATURE:
<223> OTHER INFORMATION: DNAzyme

<400> SEQUENCE: 151
tcgatagcag aa                                                         12

<210> SEQ ID NO 152
<211> LENGTH: 12
<212> TYPE: DNA
<213> ORGANISM: Artificial
<220> FEATURE:
<223> OTHER INFORMATION: DNAzyme

<400> SEQUENCE: 152
tcgatagcac aa                                                         12

<210> SEQ ID NO 153
<211> LENGTH: 12
<212> TYPE: DNA
<213> ORGANISM: Artificial
<220> FEATURE:
<223> OTHER INFORMATION: DNAzyme

<400> SEQUENCE: 153
tcgatagctt aa                                                         12

<210> SEQ ID NO 154
<211> LENGTH: 12
<212> TYPE: DNA
<213> ORGANISM: Artificial
<220> FEATURE:
<223> OTHER INFORMATION: DNAzyme

<400> SEQUENCE: 154
tcgatagcta aa                                                         12

<210> SEQ ID NO 155
<211> LENGTH: 12
<212> TYPE: DNA
<213> ORGANISM: Artificial
<220> FEATURE:

<223> OTHER INFORMATION: DNAzyme

<400> SEQUENCE: 155
tcgatagctc aa					12

<210> SEQ ID NO 156
<211> LENGTH: 12
<212> TYPE: DNA
<213> ORGANISM: Artificial
<220> FEATURE:
<223> OTHER INFORMATION: DNAzyme

<400> SEQUENCE: 156
tcgatagctg aa					12

<210> SEQ ID NO 157
<211> LENGTH: 12
<212> TYPE: DNA
<213> ORGANISM: Artificial
<220> FEATURE:
<223> OTHER INFORMATION: DNAzyme

<400> SEQUENCE: 157
tcgatagcgg aa					12

<210> SEQ ID NO 158
<211> LENGTH: 12
<212> TYPE: DNA
<213> ORGANISM: Artificial
<220> FEATURE:
<223> OTHER INFORMATION: DNAzyme

<400> SEQUENCE: 158
tcgatagcga aa					12

<210> SEQ ID NO 159
<211> LENGTH: 12
<212> TYPE: DNA
<213> ORGANISM: Artificial
<220> FEATURE:
<223> OTHER INFORMATION: DNAzyme

<400> SEQUENCE: 159
tcgatagcgt aa					12

<210> SEQ ID NO 160
<211> LENGTH: 12
<212> TYPE: DNA
<213> ORGANISM: Artificial
<220> FEATURE:
<223> OTHER INFORMATION: DNAzyme

<400> SEQUENCE: 160
tcgatagcgc aa					12

<210> SEQ ID NO 161
<211> LENGTH: 12
<212> TYPE: DNA
<213> ORGANISM: Artificial
<220> FEATURE:
<223> OTHER INFORMATION: DNAzyme

<400> SEQUENCE: 161
tcgatagccc aa					12

```
<210> SEQ ID NO 162
<211> LENGTH: 12
<212> TYPE: DNA
<213> ORGANISM: Artificial
<220> FEATURE:
<223> OTHER INFORMATION: DNAzyme

<400> SEQUENCE: 162
tcgatagcca aa                                                            12

<210> SEQ ID NO 163
<211> LENGTH: 12
<212> TYPE: DNA
<213> ORGANISM: Artificial
<220> FEATURE:
<223> OTHER INFORMATION: DNAzyme

<400> SEQUENCE: 163
tcgatagcct aa                                                            12

<210> SEQ ID NO 164
<211> LENGTH: 12
<212> TYPE: DNA
<213> ORGANISM: Artificial
<220> FEATURE:
<223> OTHER INFORMATION: DNAzyme

<400> SEQUENCE: 164
tcgatagccg aa                                                            12

<210> SEQ ID NO 165
<211> LENGTH: 12
<212> TYPE: DNA
<213> ORGANISM: Artificial
<220> FEATURE:
<223> OTHER INFORMATION: DNAzyme

<400> SEQUENCE: 165
tcgatagcaa ag                                                            12

<210> SEQ ID NO 166
<211> LENGTH: 12
<212> TYPE: DNA
<213> ORGANISM: Artificial
<220> FEATURE:
<223> OTHER INFORMATION: DNAzyme

<400> SEQUENCE: 166
tcgatagcat ag                                                            12

<210> SEQ ID NO 167
<211> LENGTH: 12
<212> TYPE: DNA
<213> ORGANISM: Artificial
<220> FEATURE:
<223> OTHER INFORMATION: DNAzyme

<400> SEQUENCE: 167
tcgatagcag ag                                                            12

<210> SEQ ID NO 168
<211> LENGTH: 12
<212> TYPE: DNA
<213> ORGANISM: Artificial
<220> FEATURE:
<223> OTHER INFORMATION: DNAzyme
```

```
<400> SEQUENCE: 168
tcgatagcac ag                                                              12

<210> SEQ ID NO 169
<211> LENGTH: 12
<212> TYPE: DNA
<213> ORGANISM: Artificial
<220> FEATURE:
<223> OTHER INFORMATION: DNAzyme

<400> SEQUENCE: 169
tcgatagctt ag                                                              12

<210> SEQ ID NO 170
<211> LENGTH: 12
<212> TYPE: DNA
<213> ORGANISM: Artificial
<220> FEATURE:
<223> OTHER INFORMATION: DNAzyme

<400> SEQUENCE: 170
tcgatagcta ag                                                              12

<210> SEQ ID NO 171
<211> LENGTH: 12
<212> TYPE: DNA
<213> ORGANISM: Artificial
<220> FEATURE:
<223> OTHER INFORMATION: DNAzyme

<400> SEQUENCE: 171
tcgatagctc ag                                                              12

<210> SEQ ID NO 172
<211> LENGTH: 12
<212> TYPE: DNA
<213> ORGANISM: Artificial
<220> FEATURE:
<223> OTHER INFORMATION: DNAzyme

<400> SEQUENCE: 172
tcgatagctg ag                                                              12

<210> SEQ ID NO 173
<211> LENGTH: 12
<212> TYPE: DNA
<213> ORGANISM: Artificial
<220> FEATURE:
<223> OTHER INFORMATION: DNAzyme

<400> SEQUENCE: 173
tcgatagcgg ag                                                              12

<210> SEQ ID NO 174
<211> LENGTH: 12
<212> TYPE: DNA
<213> ORGANISM: Artificial
<220> FEATURE:
<223> OTHER INFORMATION: DNAzyme

<400> SEQUENCE: 174
tcgatagcga ag                                                              12

<210> SEQ ID NO 175
<211> LENGTH: 12
```

```
<212> TYPE: DNA
<213> ORGANISM: Artificial
<220> FEATURE:
<223> OTHER INFORMATION: DNAzyme

<400> SEQUENCE: 175
tcgatagcgt ag                                                          12

<210> SEQ ID NO 176
<211> LENGTH: 12
<212> TYPE: DNA
<213> ORGANISM: Artificial
<220> FEATURE:
<223> OTHER INFORMATION: DNAzyme

<400> SEQUENCE: 176
tcgatagcgc ag                                                          12

<210> SEQ ID NO 177
<211> LENGTH: 12
<212> TYPE: DNA
<213> ORGANISM: Artificial
<220> FEATURE:
<223> OTHER INFORMATION: DNAzyme

<400> SEQUENCE: 177
tcgatagccc ag                                                          12

<210> SEQ ID NO 178
<211> LENGTH: 12
<212> TYPE: DNA
<213> ORGANISM: Artificial
<220> FEATURE:
<223> OTHER INFORMATION: DNAzyme

<400> SEQUENCE: 178
tcgatagcca ag                                                          12

<210> SEQ ID NO 179
<211> LENGTH: 12
<212> TYPE: DNA
<213> ORGANISM: Artificial
<220> FEATURE:
<223> OTHER INFORMATION: DNAzyme

<400> SEQUENCE: 179
tcgatagcct ag                                                          12

<210> SEQ ID NO 180
<211> LENGTH: 12
<212> TYPE: DNA
<213> ORGANISM: Artificial
<220> FEATURE:
<223> OTHER INFORMATION: DNAzyme

<400> SEQUENCE: 180
tcgatagccg ag                                                          12

<210> SEQ ID NO 181
<211> LENGTH: 30
<212> TYPE: DNA
<213> ORGANISM: Artificial
<220> FEATURE:
<223> OTHER INFORMATION: substrate
<220> FEATURE:
<221> NAME/KEY: misc_feature
<222> LOCATION: (16)..(16)
```

<223> OTHER INFORMATION: A is a ribonucleotide

<400> SEQUENCE: 181
gtcacgagtc actataggaa gatggcgaaa                                      30

<210> SEQ ID NO 182
<211> LENGTH: 41
<212> TYPE: DNA
<213> ORGANISM: Artificial
<220> FEATURE:
<223> OTHER INFORMATION: DNAzyme

<400> SEQUENCE: 182
tttcgccatc tttacaagga acggttatag tgactcgtga c                         41

<210> SEQ ID NO 183
<211> LENGTH: 35
<212> TYPE: DNA
<213> ORGANISM: Artificial
<220> FEATURE:
<223> OTHER INFORMATION: DNAzyme

<400> SEQUENCE: 183
tttcgccatc ttcgatactc tctttgactc gtgac                                35

<210> SEQ ID NO 184
<211> LENGTH: 40
<212> TYPE: DNA
<213> ORGANISM: Artificial
<220> FEATURE:
<223> OTHER INFORMATION: DNAzyme

<400> SEQUENCE: 184
aatgtagaga ggctagctac aacgagcggt ggtccttgag                           40

<210> SEQ ID NO 185
<211> LENGTH: 16
<212> TYPE: DNA
<213> ORGANISM: Artificial
<220> FEATURE:
<223> OTHER INFORMATION: DNAzyme

<400> SEQUENCE: 185
gtgggtggaa actgga                                                     16

<210> SEQ ID NO 186
<211> LENGTH: 70
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (22)..(22)
<223> OTHER INFORMATION: n is a, c, g, or t

<400> SEQUENCE: 186
cacggttcga atggcagtga tnttctacaa agcggtagaa ggatatcact gagcataatc     60
acctagtaaa                                                            70

<210> SEQ ID NO 187
<211> LENGTH: 89
<212> TYPE: DNA
<213> ORGANISM: Artificial
<220> FEATURE:
<223> OTHER INFORMATION: DNAzyme

```
<400> SEQUENCE: 187
tgacagtgat attgatcagc tatactatgc tggtcgtggg tggaaactgg ataccgaggt    60
acaaagcggt agaaggatat cactgagca                                      89

<210> SEQ ID NO 188
<211> LENGTH: 25
<212> TYPE: DNA
<213> ORGANISM: Artificial
<220> FEATURE:
<223> OTHER INFORMATION: substrate

<400> SEQUENCE: 188
gagtcactat aggaagatgg cgaaa                                          25
```

US 11,142,544 B2

PHOSPHOROTHIOATE DNAZYME COMPLEXES AND USE THEREOF

FIELD OF THE INVENTION

The present invention generally relates to DNAzymes, and more particularly, to the generation of novel modified DNAzyme complexes useful for the detection of heavy metals.

SUBMISSION OF SEQUENCE LISTING

The contents of the electronic submission of the text file Sequence Listing, which is titled HB 531218-1.txt, which was created on Jan. 12, 2016 and is 35 KB in size, is incorporated herein by reference in its entirety.

BACKGROUND OF THE INVENTION

Cadmium, mercury and lead are the most common heavy metal contaminants. These metals are bioaccumulative, and can impose serious organ damage, leading to cancer and even death. For this reason, they have collectively been banned by the European Union according to the Restriction of Hazardous Substances Directive since 2006. California has also imposed similar regulations. To enforce such regulations and to manage their adverse environmental and health effects, convenient analytical strategies are critical. The current standard method is inductive-coupled plasmon-mass spectrometry (ICP-MS). Being highly reliable, it is available only in centralized labs at a high cost and long turnaround time. However, in order to provide on-site analysis, a number of metal sensing platforms have been developed.

DNAzymes (also known as deoxyribozymes and catalytic DNA) are DNA-based catalysts obtained through in vitro selection. Owing to their high catalytic efficiency and versatility in sensor design, RNA-cleaving DNAzymes have emerged as a unique metal sensing platform. Since DNAzymes require metal cofactors, by using specific metals during selection, RNA-cleaving DNAzymes selective for $Mg^{2+}$, $Pb^{2+}$, $UO_2^{2+}$ and lanthanides have been reported. These metals are hard or borderline Lewis acids.

High thiophilicity is a common feature of many toxic metals including cadmium and mercury, but natural DNA does not contain sulfur, which might be a reason for the lack of DNAzymes selective for these metals. By incorporating modified bases with soft base ligands (e.g. imidazole group), $Zn^{2+}$- and $Hg^{2+}$-dependent DNAzymes were also isolated. Since these modified bases are not commercially available, their analytical applications have not been widely pursued. Using modified bases also complicates in vitro selection since DNA polymerase may not incorporate such bases. Phosphorothioate (PS) DNA refers to replacement of one of the non-bridging oxygen atoms in the phosphate backbone by sulfur. PS modification has been used in antisense technology to increase DNA stability against nuclease degradation. It is also useful for studying the mechanism of (deoxy) ribozyme catalysis, assembling nanoparticles, and forming DNA structures. However, PS-modified RNA-cleaving DNAzymes have not been studied.

Thus, it would be desirable to develop novel RNA-cleaving DNAzymes having beneficial metal sensing properties.

SUMMARY OF THE INVENTION

Novel substrate-bound DNAzymes have now been developed which are useful for the detection of heavy metals.

In one aspect of the invention, substrate-bound DNAzyme complex is provided comprising a DNAzyme bound to a nucleic acid-based substrate, wherein the DNAzyme comprises a pair of binding arms which hybridize to binding regions on the substrate, and a catalytic domain between the binding arms, and the nucleic acid-based substrate comprises a phosphorothioate-modified ribonucleotide DNAzyme cleavage site between the binding regions, wherein the catalytic domain of the DNAzyme catalyzes heavy metal-dependent cleavage of the substrate cleavage site.

In another aspect, a method of sensing heavy metals in a sample is provided, comprising i) incubating the sample with a substrate-bound DNAzyme complex comprising a DNAzyme bound to a detectably labelled nucleic acid-based substrate, wherein the DNAzyme comprises a pair of binding arms which hybridize to binding regions on the substrate, and a catalytic domain between the binding arms, and the nucleic acid-based substrate comprises a phosphorothioate-modified ribonucleotide DNAzyme cleavage site between the binding regions, wherein the catalytic domain of the DNAzyme catalyzes heavy metal-dependent cleavage of the substrate cleavage site, and ii) determining the presence of a heavy metal in the sample by detecting a labelled substrate cleavage product.

In another aspect, a heavy metal-detecting array is provided comprising at least two different DNAzyme complexes as described.

In a further aspect, a cadmium-selective DNAzyme is provided comprising a pair of binding arms and a catalytic domain between the binding arms, wherein the catalytic domain comprises the sequence:

(SEQ ID NO: 52)
5'-TCGA-T/C-AG-T/C-NN-A-A/G.

In another aspect, a method of detecting cadmium in a sample is provided, comprising i) incubating the sample with a cadmium-selective substrate-bound DNAzyme complex, wherein the DNAzyme comprises a pair of binding arms hybridized to binding regions on the substrate, and a catalytic domain between the binding arms comprising the sequence, 5'-TCGA-T/C-AG-T/C-NN-A-A/G, and a detectably labelled nucleic acid-based substrate comprising a phosphorothioate-modified ribonucleotide cleavage site between the binding regions, and ii) determining the presence of cadmium in the sample by detecting a labelled substrate cleavage product.

In another aspect, a method of chiral separation of an isomeric DNAzyme substrate comprising a phosphorothioate-modified ribonucleotide target site is provided, comprising incubating a $Mg^{2+}$-dependent DNAzyme with the substrate for a sufficient period of time to permit degradation of an $S_p$-stereoisomer to provide a substrate enriched for the $R_p$-stereoisomer.

These and other aspects of the invention will be described by reference to the following Figures.

BRIEF DESCRIPTION OF THE FIGURES

FIG. 3 illustrates the enzyme loop sequence of Ce13d (the nucleotides in black of FIG. 1B) and the sites of PS modification (blue stars) (A), as well as gel images of 16 Ce13d-based enzyme assays with (B) $Ce^{3+}$, (C) $Cd^{2+}$ or (D) $Pb^{2+}$ (the first lane is the substrate alone, the second lane is with the normal PO enzyme and the rest are the PS modified)

FIG. 11 illustrates (A) the structures of the two PS diastereomers at the cleavage junction of a DNAzyme; (B) a scheme of HPLC separation followed by ligation to obtain the two diastereomers of the substrate; (C) an HPLC trace of the separation; and (D) kinetics of the $R_p$ and $S_p$ substrate cleaved by the BN-Cd16 and $Cd^{2+}$.

DETAILED DESCRIPTION OF THE INVENTION

Figure 1A:
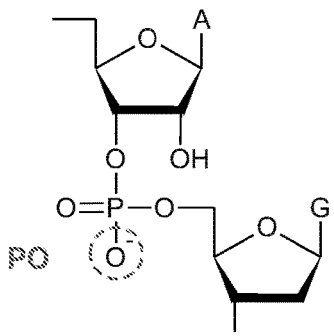
FIG. 1 illustrates (A) the structure of a normal phosphodiester (PO) linkage vs. a phosphorothioate (PS) modification at the cleavage junction (rA-G), and secondary structures of the four DNAzymes used in this work: (B) Ce13d; (C) GR5; (D) 17E; and (E) 39E; as well as sequence information for: (F) Lu12; (G) Tm7; and (H) 10-23.
Figure 1A:
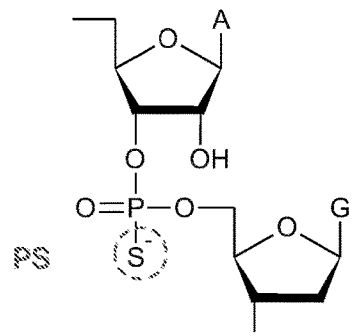
Figure 1B:
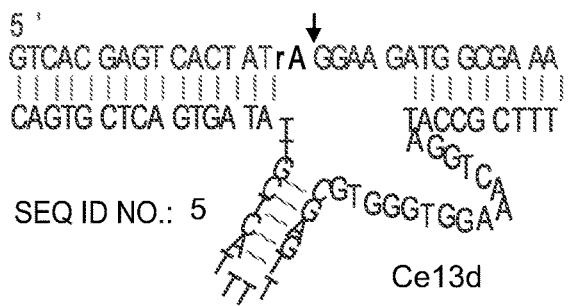
Figure 1C:
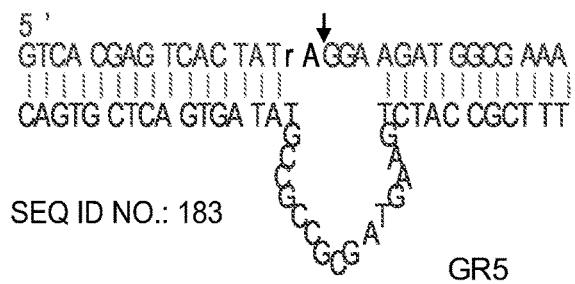
Figure 1D:
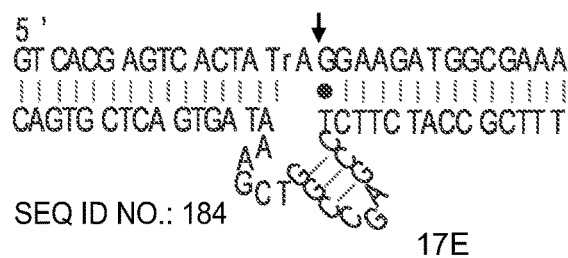
Figure 1E:
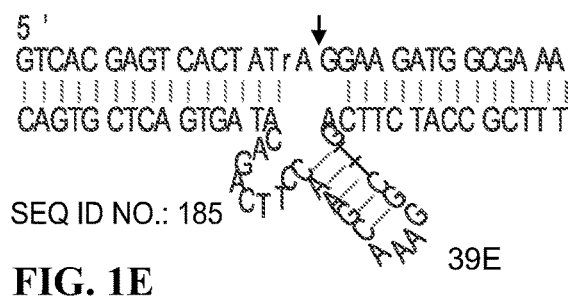
Figure 1F:
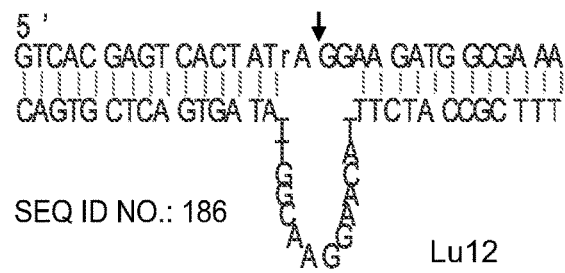
Figure 1G:
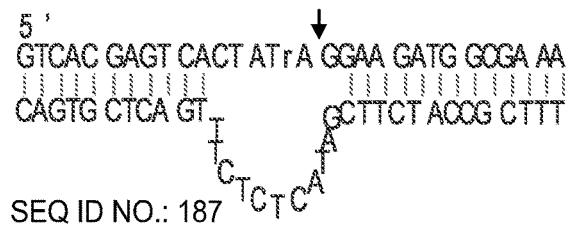
Figure 1H:
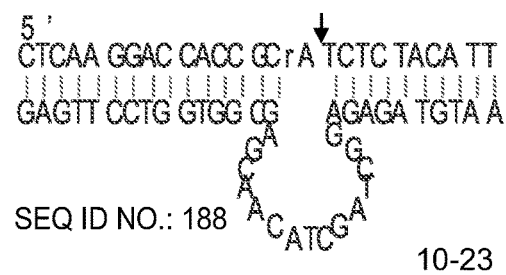

In one aspect of the invention, substrate-bound DNAzyme complex is provided comprising a DNAzyme bound to a nucleic acid-based substrate, wherein the DNAzyme comprises a pair of binding arms which hybridize to binding regions on the substrate, and a catalytic domain between the binding arms, and the nucleic acid-based substrate comprises a phosphorothioate-modified ribonucleotide DNAzyme cleavage site between the binding regions, wherein the catalytic domain of the DNAzyme catalyzes heavy metal-dependent cleavage of the substrate target site.

The term "DNAzyme" is used herein to encompass deoxyribonucleic acid (DNA)-based catalysts capable of cleaving a nucleic acid-based substrate comprising a ribo-nucleotide at a cleavage site within the substrate in the presence of a metal cofactor. The DNAzyme comprises a pair of binding arms which are complementary to binding regions on the nucleic acid substrate. Each binding arm of the DNAzyme comprises a number of nucleotides to permit sufficient bonding between the DNAzyme and its substrate to facilitate DNAzyme activity (i.e. cleavage of the substrate at the target cleavage site), for example, each binding arm may comprise at least about 5 nucleotides, preferably at least about 10 nucleotides, 15 nucleotides or 20 nucleotides. The binding arms may be the same or different lengths. The binding arms may also comprise modified DNA, including modified bases such as xanthine, hypoxanthine, 2-aminoadenine, 6-methyl, 2-propyl and other alkyl adenines, 5-halo uracil, 5-halo cytosine, 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydrolyl guanine and other 8-substituted guanines, other aza and deaza uracils, thymidines, cytosines, adenines, or guanines, 5-trifluoromethyl uracil and 5-trifluoro cytosine; modified phosphorous, oxygen heteroatoms in the phosphate backbone, short chain alkyl or cycloalkyl intersugar linkages or short chain heteroatomic or heterocyclic intersugar linkages. For example, the binding arms may contain phosphorothioates, phosphotriesters, methyl phosphonates and phosphorodithioates, and may contain a combination of linkages, for example, phosphorothioate bonds may link only the four to six 3'-terminal bases, may link all the nucleotides or may link only 1 pair of bases. The binding arms may further include peptide nucleic acid (PNA) in which the deoxribose (or ribose) phosphate backbone in the DNA is replaced with a polyamide backbone, or may include polymer backbones, cyclic backbones, or acyclic backbones. The binding regions may incorporate sugar mimetics, and may additionally include protective groups, particularly at terminal ends thereof, to prevent undesirable degradation.

The DNAzyme additionally comprises a catalytic domain between the binding arms, generally in the form of a loop, which includes single-stranded DNA, and may optionally include double-stranded regions. The terminal 5'- and 3' ends of the catalytic domain are each linked to a binding arm at the appropriate corresponding terminus of the binding arm (e.g. 5' to 3'). The catalytic region may incorporate modified nucleotides, including modified bases, backbone, sugars and/or linkages to the extent that such modifications do not have an adverse affect on catalytic activity (i.e. cleavage activity) of the DNAzyme. The size of the catalytic domain in each DNAzyme is not particularly limited, and may include, for example, at least about 2 nucleotides or more, for example, 2 to about 50-100 nucleotides, such 5 to 30 nucleotides, e.g. 8 to 12 nucleotides, as long as it is reactive with the target site of the selected substrate. The term "about" is used herein to mean an amount that may differ somewhat from the given value, by an amount that would not be expected to significantly affect activity or outcome as appreciated by one of skill in the art, for example, a variance of from 1-10% from the given value.

Examples of DNAzymes in accordance with the invention, include, but are not limited to, lanthanide-dependent DNAzymes such as Ce13d, Lu12 and Tm7, magnesium-dependent DNAzymes such as 17E and 10-23, uranyl-specific DNAzymes such as 39E, lead-dependent DNAzymes such as GR5, and functionally equivalent DNAzymes derived from any of these which exhibit a high degree of sequence identity, e.g. at least about 70%, preferably at least about 80%, 85%, 90% or 95%. The term "functionally equivalent" refers to DNAzymes which retain the ability to cleave the DNAzyme substrate. Nucleotide sequences of DNAzymes are shown in FIG. 1.

The present DNAzymes target a nucleic acid-based substrate comprising binding regions which are essentially complementary to the binding arms of the DNAzyme, and which hybridize with the binding arms of the DNAzyme. In this regard, it is noted that the binding regions need not be fully complementary with the binding arms of the DNAzyme, provided that they hybridize sufficiently with the DNAzyme such that the catalytic activity of the DNAzyme is not adversely affected (e.g. exhibit at least about 70% complementarity, preferably 80-90%, and more preferably, 95% or greater). Likewise, the binding regions of the DNAzyme substrate may incorporate modified nucleotides, including modified bases, backbone, sugars and/or linkages to the extent that such modifications do not have an adverse effect on DNAzyme catalytic activity, for example, as a result of reduced hybridization. The substrate additionally comprises a phosphorothioate-modified ribonucleotide cleavage site which is targeted by the catalytic domain of the DNAzyme. The cleavage site may be any phosphorothioate-modified ribonucleotide, e.g. including adenine, cytosine, guanine or uracil, and may be linked to any nucleotide, e.g. including adenine, cytosine, guanine, thymine (uracil). In one embodiment, the cleavage site is a ribonucleotide including adenine, linked to a nucleotide including guanine.

The cleavage site is within a target region of the substrate situated between the binding regions. The terminal 5'- and 3' ends of the target region are each linked to a binding region at the appropriate corresponding terminus (e.g. 5' to 3') of the binding arm. The target region may include only the cleavage site, or may include additional nucleotides, e.g. deoxyribonucleotides or ribonucleotides, on either side thereof. Additional nucleotides may be modified, including modified backbone, sugars and/or linkages, to the extent that such modifications do not have an adverse affect on catalytic activity (i.e. cleavage activity) of the DNAzyme. The number of nucleotides within the target region is not particularly restricted.

The size of the DNAzyme substrate is also not particularly restricted, as long as it hybridizes to the DNAzyme and is cleavable by the DNAzyme. In one embodiment, the DNAzyme substrate has the nucleotide sequence, 5'GTCACGAGTCACTATrAGGAAGATGGCGAAA3', wherein "r" denotes ribonucleotide, rA being the cleavage site (SEQ ID NO.181).

The term "phosphorothioate (PS) modified" as it used herein regarding the ribonucleotide cleavage site of the DNAzyme substrate refers to replacement of a non-bridging oxygen atom in the phosphate backbone of the ribonucleotide with a sulfur atom. PS-modification of the substrate is readily accomplished using standard chemical reactions, as would be appreciated by those of skill in the art. The PS-modified ribonucleotide may incorporate any one of adenine, uracil, guanine or cytosine, and may be linked on either side to a nucleotide incorporating any one of adenine, thymine (uracil), guanine or cytosine. In one embodiment, the cleavage site is a PS-modified ribonucleotide incorporating adenine linked to a nucleotide incorporating guanine (at the cleavage junction). It is noted that the PS modification yields to diastereomers, e.g. R- and S-diastereomers. Different DNAzymes may exhibit different activity for each of these diastereomers. In one embodiment, the substrate comprises a mixture of diastereomers. In another embodiment, the substrate is predominantly the R-isomer, and in another embodiment, the substrate is predominantly the S-isomer. The term "predominantly" is used herein to refer to a substrate solution that comprises more of the predominant isomer, e.g. greater than 50% of the predominant isomer, and preferably, greater than 80%, 85%, 90%, 95% or 100%, of the predominant isomer.

The DNAzyme and its PS-modified substrate may be connected at their corresponding 5' and 3' termini, e.g. by a looped or other structure. Alternatively, their terminal ends may be capped, for example, with protecting groups, to prevent undesired breakdown and degradation, particularly on exposure to aqueous samples to be tested as will described. It is also noted that the binding arms of the DNAzyme may overhang the corresponding binding region of the substrate, or the binding region of the substrate may overhang the corresponding binding arm of the DNAzyme, without affecting the activity of the complex.

The DNAzyme and its nucleic acid-based substrate may be prepared using standard chemical synthetic techniques. In addition, substrate-bound DNAzyme complex is prepared using standard hybridization protocols.

While not wishing to be bound by any particular theory, the PS modification at the substrate cleavage site shifts the activity of the DNAzyme from dependence on a metal cofactor that prefers an oxygen-based ligand, to dependence on a metal cofactor that prefers a sulfur-based ligand, rendering the DNAzyme to be dependent on thiophilic metal cofactors, including, for example, mercury, lead, copper, thallium, silver and cadmium. The present PS-modified substrate-bound DNAzymes, thus, cleave PS-modified substrate in the presence of heavy metal cofactors. Since DNAzymes are not known to cleave unmodified substrate (i.e. PO substrate) in the presence of heavy metals, PS-modified substrate-bound DNAzyme complex may be used to detect the presence of a heavy metal, i.e. as heavy metal biosensors.

Thus, in another aspect of the invention, a method of sensing heavy metals in a sample is provided. The method includes the step of incubating a sample with a PS-modified substrate-bound DNAzyme complex to determine the presence of a heavy metal in the sample for a period of time sufficient to permit cleavage of the substrate, for example, about 1-60 minutes, such as 1-30 minutes. The incubation is conducted under conditions suitable to permit cleavage, e.g. room temperature, and at a pH in the range of about 6-7.8 (e.g. 7-7.6). The sample is not particularly limited and may include any aqueous sample, including water samples (e.g. drinking water, water used for irrigation, water from natural sources such as lakes, ponds and rivers, community or municipal water sources, water from aquariums or other fish farming tanks, etc.), as well as aqueous extracts from various sources to determine exposure to heavy metals, including fruits, vegetables, crops such as maize (corn), wheat, rice, legumes such soybeans, hay, and sugarcane, soil, and the like. For heavy metal detection, the amount of substrate-bound DNAzyme complex will vary with the detection method used. In one embodiment, an amount of DNAzyme complex in the range of about 5 nM to 1 µM is used for metal sensing. With respect to the sample to be tested, an amount of aqueous sample in the range of about 5 µL to 5 mL may be used for metal sensing.

In order to detect DNAzyme activity, the PS-modified substrate is detectably labelled so as to yield a detectable cleavage product. In this regard, the substrate is tagged, for example, at its 3' end, with a detectable label. Any suitable detectable label may be used including, but not limited to, a fluorescent label such as rhodamine, fluorescein (e.g. carboxyfluorescein) and cyanine derivatives; hapten labels such as biotin and digoxigenin; radiolabels such as $^2$H, $^{13}$C, and $^{15}$N; chromogenic labels; chemiluminescent labels; phosphorescent labels; nanoparticle labels; enzymatic labels; and the like. On cleavage of the substrate by the DNAzyme, the labelled cleavage product is released, and can be detected using well-established techniques based on the selected detectable label. For example, the detection may be conducted in solution, and release of the labelled cleavage product may be identified using a separation technique such as gel electrophoresis, e.g. polyacrylamide gel electrophoresis. Alternatively, the DNAzyme complex may be immobilized on a surface, exposed to the sample to be tested, and release of the cleavage product subsequently detected.

Detection of the cleaved PS-modified substrate product on incubation of a sample with the present DNAzyme complex indicates the presence of a heavy thiophilic metal in the sample. Generally, the greater the amount of cleaved substrate, indicated by the strength of the detected label, the greater the level of heavy metal in the sample. In this regard, however, it is noted that the activity of a DNAzyme may be the same or different in the presence of different metals. Thus, a DNAzyme may be highly selective for cadmium, i.e. exhibit a high degree of substrate cleavage in the presence of cadmium, while the same DNAzyme may be equally selective for lead, and much less selective for mercury, i.e. exhibit a reduced degree of substrate cleavage in comparison to that in the presence of cadmium. In addition, the substrate cleavage activity of different DNAzymes may be the same or different in the presence of the same heavy metal. For example, one DNAzyme may be highly selective for cadmium, i.e. exhibit a high degree of substrate cleavage in the presence of cadmium, and a second DNAzyme may be equally selective for cadmium; while a third DNAzyme may be much less selective for cadmium, i.e. exhibit a reduced degree of substrate cleavage in comparison to that of the first DNAzyme in the presence of cadmium. Selectivity of a DNAzyme for a given thiophilic metal is readily determined using standardized heavy metal solutions.

In embodiments of the invention, using a PS-modified substrate, Ce13d DNAzyme exhibits substrate cleavage activity in the presence of each of the metals, cadmium, lead and mercury, GR5 and 39E exhibit substrate cleavage activity in the presence of mercury and lead, and 17E exhibits cleavage activity in the presence of lead only.

The present method not only provides specific detection of heavy metals, but also exhibits sensitive heavy metal detection at parts-per-trillion levels, for example, heavy metal levels as low as about 0.1-50 nM of metal. As one of skill in the art will appreciate, detection level will vary with the selectivity of a given DNAzyme complex for a heavy metal as herein described.

In view of the variable activity of DNAzymes for a PS-modified substrate in the presence of a thiophilic metal cofactor, a heavy metal sensor array comprising two or more different DNAzyme/PS-modified substrate complexes, may be utilized to identify the heavy metal in a sample. Preferably, the array comprises at least two DNAzyme complexes exhibiting unique activity in the presence of different heavy metal cofactors. In an embodiment of the invention, the PS-modified substrate-bound DNAzymes, Ce13d, GR5, 17E and 39E, may be used in an array to identify which heavy metals are in a sample. As described above, each of the PS-modified substrate-bound DNAzymes are incubated in the presence of a sample for a period of time sufficient to permit cleavage of the substrate, followed by detection of cleaved substrate. Detection of substrate cleavage by Ce13d only indicates that the sample contains cadmium, detection of substrate cleavage by each of Ce13d, GR5, 17E and 39E indicates the presence of lead in the sample, while detection of substrate cleavage by Ce13d, GR5, 39E, but not 17E indicates that the presence of mercury in the sample.

The present detection method advantageously provides a means of heavy metal detection that is straight-forward, cost-effective, and provides detection which is both sensitive (below toxic levels) and selective.

For use to conduct the present method, a kit is provided comprising at least one of a PS-modified substrate for a ribonucleotide-cleaving DNAzyme, optionally labelled for detection; one or more DNAzymes; solutions, buffers, and the like, including a detectable label and/or quencher, for use to form a DNAzyme complex with a PS-modified substrate, and/or to conduct a DNAzyme cleavage reaction; and heavy metal standard solutions. The kit may also include instructions describing how to conduct the method as described herein.

In a further aspect, a novel cadmium-selective DNAzyme is provided comprising a pair of binding arms and a single-stranded catalytic domain between the binding arms, wherein the catalytic domain comprises the sequence:

```
                                             (SEQ ID NO: 52)
    5' TCGA-T/C-AG-T/C-NN-A-A/G 3'.
```

The catalytic domain comprises 12 nucleotides, including both conserved and variable regions. Conserved nucleotides occur at positions 1-4, 6-7 and 11. A pyrimidine base, e.g. cytosine or thymine, occur at position 5 and 8, and a purine base occurs at position 12. A nucleotide including any one of adenine, guanine, cytosine or thymine, may occur at positions 9 and 10 without impact on cleavage activity of the DNAzyme.

Thus, the catalytic domain may comprise, for example, any of the following sequences (5' to 3'):

```
                      (SEQ ID NO: 53)
TCGA-T-AG-T-AA-A-A;

(SEQ ID NO: 54)
TCGA-T-AG-T-AT-A-A;

(SEQ ID NO: 55)
TCGA-T-AG-T-AG-A-A;

(SEQ ID NO: 56)
TCGA-T-AG-T-AC-A-A;

(SEQ ID NO: 57)
TCGA-T-AG-T-TT-A-A;

(SEQ ID NO: 58)
TCGA-T-AG-T-TA-A-A;

(SEQ ID NO: 59)
TCGA-T-AG-T-TC-A-A;

(SEQ ID NO: 60)
TCGA-T-AG-T-TG-A-A;

(SEQ ID NO: 61)
TCGA-T-AG-T-GG-A-A;

(SEQ ID NO: 62)
TCGA-T-AG-T-GA-A-A;

(SEQ ID NO: 63)
TCGA-T-AG-T-GT-A-A;

(SEQ ID NO: 64)
TCGA-T-AG-T-GC-A-A;

(SEQ ID NO: 65)
TCGA-T-AG-T-CC-A-A;

(SEQ ID NO: 66)
TCGA-T-AG-T-CA-A-A;

(SEQ ID NO: 67)
TCGA-T-AG-T-CT-A-A;

(SEQ ID NO: 68)
TCGA-T-AG-T-CG-A-A;

(SEQ ID NO: 69)
TCGA-T-AG-T-AA-A-G;

(SEQ ID NO: 70)
TCGA-T-AG-T-AT-A-G;

(SEQ ID NO: 71)
TCGA-T-AG-T-AG-A-G;

(SEQ ID NO: 72)
TCGA-T-AG-T-AC-A-G;

(SEQ ID NO: 73)
TCGA-T-AG-T-TT-A-G;

(SEQ ID NO: 74)
TCGA-T-AG-T-TA-A-G;

(SEQ ID NO: 75)
TCGA-T-AG-T-TC-A-G;

(SEQ ID NO: 76)
TCGA-T-AG-T-TG-A-G;

(SEQ ID NO: 77)
TCGA-T-AG-T-GG-A-G;

(SEQ ID NO: 78)
TCGA-T-AG-T-GA-A-G;

(SEQ ID NO: 79)
TCGA-T-AG-T-GT-A-G;

(SEQ ID NO: 80)
TCGA-T-AG-T-GC-A-G;

(SEQ ID NO: 81)
TCGA-T-AG-T-CC-A-G;

(SEQ ID NO: 82)
TCGA-T-AG-T-CA-A-G;

(SEQ ID NO: 83)
TCGA-T-AG-T-CT-A-G;

(SEQ ID NO: 84)
TCGA-T-AG-T-CG-A-G;

(SEQ ID NO: 85)
TCGA-C-AG-C-AA-A-A;

(SEQ ID NO: 86)
TCGA-C-AG-C-AT-A-A;

(SEQ ID NO: 87)
TCGA-C-AG-C-AG-A-A;

(SEQ ID NO: 88)
TCGA-C-AG-C-AC-A-A;

(SEQ ID NO: 89)
TCGA-C-AG-C-TT-A-A;

(SEQ ID NO: 90)
TCGA-C-AG-C-TA-A-A;

(SEQ ID NO: 91)
TCGA-C-AG-C-TC-A-A;

(SEQ ID NO: 92)
TCGA-C-AG-C-TG-A-A;

(SEQ ID NO: 93)
TCGA-C-AG-C-GG-A-A;

(SEQ ID NO: 94)
TCGA-C-AG-C-GA-A-A;

(SEQ ID NO: 95)
TCGA-C-AG-C-GT-A-A;

(SEQ ID NO: 96)
TCGA-C-AG-C-GC-A-A;

(SEQ ID NO: 97)
TCGA-C-AG-C-CC-A-A;

(SEQ ID NO: 98)
TCGA-C-AG-C-CA-A-A;

(SEQ ID NO: 99)
TCGA-C-AG-C-CT-A-A;

(SEQ ID NO: 100)
TCGA-C-AG-C-CG-A-A;
```

-continued

TCGA-C-AG-C-AA-A-G; (SEQ ID NO: 101)

TCGA-C-AG-C-AT-A-G; (SEQ ID NO: 102)

TCGA-C-AG-C-AG-A-G; (SEQ ID NO: 103)

TCGA-C-AG-C-AC-A-G; (SEQ ID NO: 104)

TCGA-C-AG-C-TT-A-G; (SEQ ID NO: 105)

TCGA-C-AG-C-TA-A-G; (SEQ ID NO: 106)

TCGA-C-AG-C-TC-A-G; (SEQ ID NO: 107)

TCGA-C-AG-C-TG-A-G; (SEQ ID NO: 108)

TCGA-C-AG-C-GG-A-G; (SEQ ID NO: 109)

TCGA-C-AG-C-GA-A-G; (SEQ ID NO: 110)

TCGA-C-AG-C-GT-A-G; (SEQ ID NO: 111)

TCGA-C-AG-C-GC-A-G; (SEQ ID NO: 112)

TCGA-C-AG-C-CC-A-G; (SEQ ID NO: 113)

TCGA-C-AG-C-CA-A-G; (SEQ ID NO: 114)

TCGA-C-AG-C-CT-A-G; (SEQ ID NO: 115)

TCGA-C-AG-C-CG-A-G; (SEQ ID NO: 116)

TCGA-C-AG-T-AA-A-A; (SEQ ID NO: 117)

TCGA-C-AG-T-AT-A-A; (SEQ ID NO: 118)

TCGA-C-AG-T-AG-A-A; (SEQ ID NO: 119)

TCGA-C-AG-T-AC-A-A; (SEQ ID NO: 120)

TCGA-C-AG-T-TT-A-A; (SEQ ID NO: 121)

TCGA-C-AG-T-TA-A-A; (SEQ ID NO: 122)

TCGA-C-AG-T-TC-A-A; (SEQ ID NO: 123)

TCGA-C-AG-T-TG-A-A; (SEQ ID NO: 124)

TCGA-C-AG-T-GG-A-A; (SEQ ID NO: 125)

TCGA-C-AG-T-GA-A-A; (SEQ ID NO: 126)

TCGA-C-AG-T-GT-A-A; (SEQ ID NO: 127)

TCGA-C-AG-T-GC-A-A; (SEQ ID NO: 128)

TCGA-C-AG-T-CC-A-A; (SEQ ID NO: 129)

TCGA-C-AG-T-CA-A-A; (SEQ ID NO: 130)

TCGA-C-AG-T-CT-A-A; (SEQ ID NO: 131)

TCGA-C-AG-T-CG-A-A; (SEQ ID NO: 132)

TCGA-C-AG-T-AA-A-G; (SEQ ID NO: 133)

TCGA-C-AG-T-AT-A-G; (SEQ ID NO: 134)

TCGA-C-AG-T-AG-A-G; (SEQ ID NO: 135)

TCGA-C-AG-T-AC-A-G; (SEQ ID NO: 136)

TCGA-C-AG-T-TT-A-G; (SEQ ID NO: 137)

TCGA-C-AG-T-TA-A-G; (SEQ ID NO: 138)

TCGA-C-AG-T-TC-A-G; (SEQ ID NO: 139)

TCGA-C-AG-T-TG-A-G; (SEQ ID NO: 140)

TCGA-C-AG-T-GG-A-G; (SEQ ID NO: 141)

TCGA-C-AG-T-GA-A-G; (SEQ ID NO: 142)

TCGA-C-AG-T-GT-A-G; (SEQ ID NO: 143)

TCGA-C-AG-T-GC-A-G; (SEQ ID NO: 144)

TCGA-C-AG-T-CC-A-G; (SEQ ID NO: 145)

TCGA-C-AG-T-CA-A-G; (SEQ ID NO: 146)

TCGA-C-AG-T-CT-A-G; (SEQ ID NO: 147)

TCGA-C-AG-T-CG-A-G; (SEQ ID NO: 148)

TCGA-T-AG-C-AA-A-A; (SEQ ID NO: 149)

TCGA-T-AG-C-AT-A-A; (SEQ ID NO: 150)

TCGA-T-AG-C-AG-A-A; (SEQ ID NO: 151)

TCGA-T-AG-C-AC-A-A; (SEQ ID NO: 152)

TCGA-T-AG-C-TT-A-A; (SEQ ID NO: 153)

TCGA-T-AG-C-TA-A-A; (SEQ ID NO: 154)

-continued

TCGA-T-AG-C-TC-A-A; (SEQ ID NO: 155)

TCGA-T-AG-C-TG-A-A; (SEQ ID NO: 156)

TCGA-T-AG-C-GG-A-A; (SEQ ID NO: 157)

TCGA-T-AG-C-GA-A-A; (SEQ ID NO: 158)

TCGA-T-AG-C-GT-A-A; (SEQ ID NO: 159)

TCGA-T-AG-C-GC-A-A; (SEQ ID NO: 160)

TCGA-T-AG-C-CC-A-A; (SEQ ID NO: 161)

TCGA-T-AG-C-CA-A-A; (SEQ ID NO: 162)

TCGA-T-AG-C-CT-A-A; (SEQ ID NO: 163)

TCGA-T-AG-C-CG-A-A; (SEQ ID NO: 164)

TCGA-T-AG-C-AA-A-G; (SEQ ID NO: 165)

TCGA-T-AG-C-AT-A-G; (SEQ ID NO: 166)

TCGA-T-AG-C-AG-A-G; (SEQ ID NO: 167)

TCGA-T-AG-C-AC-A-G; (SEQ ID NO: 168)

TCGA-T-AG-C-TT-A-G; (SEQ ID NO: 169)

TCGA-T-AG-C-TA-A-G; (SEQ ID NO: 170)

TCGA-T-AG-C-TC-A-G; (SEQ ID NO: 171)

TCGA-T-AG-C-TG-A-G; (SEQ ID NO: 172)

TCGA-T-AG-C-GG-A-G; (SEQ ID NO: 173)

TCGA-T-AG-C-GA-A-G; (SEQ ID NO: 174)

TCGA-T-AG-C-GT-A-G; (SEQ ID NO: 175)

TCGA-T-AG-C-GC-A-G; (SEQ ID NO: 176)

TCGA-T-AG-C-CC-A-G; (SEQ ID NO: 177)

TCGA-T-AG-C-CA-A-G; (SEQ ID NO: 178)

-continued

TCGA-T-AG-C-CT-A-G; (SEQ ID NO: 179)
AND

TCGA-T-AG-C-CG-A-G. (SEQ ID NO: 180)

Thus, a DNAzyme comprising the cadmium-selective catalytic region is advantageously used in a method to selectively detect cadmium. As described above, the DNAzyme, bound to its PS-modified and detectably-labelled substrate is incubated with an aqueous sample under conditions and for period of time sufficient for substrate cleavage to occur. Suitable PS-modified ribonucleotide substrates are described above. Detection of substrate cleavage (e.g. by detecting labelled cleavage product) indicates the presence of cadmium in the sample. In one embodiment, the PS-modified ribonucleotide substrate utilized in the method is the R-stereoisomer.

In another aspect, a method of chiral separation of an isomeric DNAzyme substrate comprising a phosphorothioate-modified ribonucleotide target site is provided, comprising incubating an $Mg^{2+}$-dependent DNAzyme with the substrate, in the presence of $Mg^{2+}$, for a sufficient period of time to permit degradation of an S-stereoisomer to provide a substrate enriched for the R-stereoisomer.

Examples of $Mg^{2+}$-dependent DNAzymes that may be used in this method include, but are not limited to, 17E and 10-23. The DNAzyme/PS-modified substrate complex is formed and incubated, in the presence of a catalytic amount of magnesium, e.g. 0.1-50 nM, for a period of time sufficient to permit cleavage of the substrate, for example, about 1-60 minutes, The incubation is conducted under conditions suitable to permit cleavage, e.g. room temperature, and at a pH in the range of about 6-7.8 (e.g. 7-7.6). This incubation results in preferential cleavage of the S-isomer. The uncleaved DNAzyme complex may then be separated from the reaction mixture, enriched with the R-isomer. Using well-established techniques, the R-isomer can then be isolated for a desired utility, e.g. heavy metal sensing.

Embodiments of the invention are described in the following examples which are not to be construed as limiting.

Example 1—PS-modified DNAzyme Complexes

PS-modified DNAzymes that detect $Hg^{2+}$, $Cd^{2+}$ and $Pb^{2+}$ as a group and individually with ultrahigh sensitivity were prepared and tested as follows.

Materials and Methods

Chemicals.

The fluorophore/quencher-modified DNAs were purchased from Integrated DNA Technologies (IDT, Coralville, Iowa). The unmodified and phosphorothioate (PS) modified enzyme strands were from Eurofins (Huntsville, Ala.). The DNA sequences used in this study are listed in Table 1. Cerium chloride heptahydrate, magnesium sulfate, manganese chloride tetrahydrate, iron chloride tetrahydrate, cobalt chloride hexahydrate, nickel chloride, copper chloride dihydrate, zinc chloride, cadmium chloride hydrate, mercury perchlorate, and lead acetate were purchased from Sigma-Aldrich except the iron salt was from Alfa Aesar. The solutions were made by directly dissolving their salts in water. 2-(N-morpholino)ethanesulfonic acid (MES), 2-[4-(2-hydroxyethyl)piperazin-1-yl]ethanesulfonic acid (HEPES), EDTA disodium salt dehydrate, and sodium chloride were purchased from Mandel Scientific Inc (Guelph, Ontario, Canada). Acrylamide/bisacrylamide 40% solution (29:1), urea, and 10×TBE solution were purchased from Bio Basic Inc.

TABLE 1

DNAzyme and substrate sequences used in this work.

| DNA Name | Sequences and modifications (from 5'-terminus) |
|---|---|
| PO substrate | CGTTCGCCTCATGACGTTGAAGGATCCAGACT-FAM (SEQ ID NO: 1) |
| PS1 | GTCACGAGTCACTAT*rAGGAAGATGGCGAAA-FAM (SEQ ID NO: 2) |
| PS2 | GTCACGAGTCACTATrA*GGAAGATGGCGAAA-FAM (SEQ ID NO: 3) |
| PS3 | GTCACGAGTCACTAT*rA*GGAAGATGGCGAAA-FAM (SEQ ID NO: 4) |
| Ce13d | TTTCGCCATAGGTCAAAGGTGGGTGCGAGTTTTTACTCGTTATAGTGACTCGTGAC (SEQ ID NO: 5) |
| 17E | CGCCATCTTCTCCGAGCCGGTCGAAATAGTGACTCGTGAC (SEQ ID NO: 6) |
| GR5 | TTTCGCCATCTGAAGTAGCGCCGCCGTATAGTGACTCGTGAC (SEQ ID NO: 7) |
| 39E | TTTCGCCATCTTCAGTTCGGAAACGAACCTTCAGACATAGTGACTCGTGAC (SEQ ID NO: 8) |
| Ce13d-Q | Q-TTTCGCCATAGGTCAAAGGTGGGTGCGAGTTTTTACTCGTTATAGTGACTCGTGAC (SEQ ID NO: 9) |
| GR5-Q | Q-TTTCGCCATCTGAAGTAGCGCCGCCGTATAGTGACTCGTGAC (SEQ ID NO: 10) |
| Ce13d-A1* | TTTCGCCATA*GGTCAAAGGTGGGTGCGAGTTTTTACTCGTTATAGTGACTCGTGAC (SEQ ID NO: 11) |
| Ce13d-G2* | TTTCGCCATAG*GTCAAAGGTGGGTGCGAGTTTTTACTCGTTATAGTGACTCGTGAC (SEQ ID NO: 12) |
| Ce13d-G3* | TTTCGCCATAGG*TCAAAGGTGGGTGCGAGTTTTTACTCGTTATAGTGACTCGTGAC (SEQ ID NO: 13) |
| Ce13d-T4* | TTTCGCCATAGGT*CAAAGGTGGGTGCGAGTTTTTACTCGTTATAGTGACTCGTGAC (SEQ ID NO: 14) |
| Ce13d-C5* | TTTCGCCATAGGTC*AAAGGTGGGTGCGAGTTTTTACTCGTTATAGTGACTCGTGAC (SEQ ID NO: 15) |
| Ce13d-A6* | TTTCGCCATAGGTCA*AAGGTGGGTGCGAGTTTTTACTCGTTATAGTGACTCGTGAC (SEQ ID NO: 16) |
| Ce13d-A7* | TTTCGCCATAGGTCAA*AGGTGGGTGCGAGTTTTACTCGTTATAGTGACTCGTGAC (SEQ ID NO: 17) |
| Ce13d-A8* | TTTCGCCATAGGTCAAA*GGTGGGTGCGAGTTTTTACTCGTTATAGTGACTCGTGAC (SEQ ID NO: 18) |
| Ce13d-G9* | TTTCGCCATAGGTCAAAG*GTGGGTGCGAGTTTTTACTCGTTATAGTGACTCGTGAC (SEQ ID NO: 19) |
| Ce13d-G10* | TTTCGCCATAGGTCAAAGG*TGGGTGCGAGTTTTTACTCGTTATAGTGACTCGTGAC (SEQ ID NO: 20) |
| Ce13d-T11* | TTTCGCCATAGGTCAAAGGT*GGGTGCGAGTTTTTACTCGTTATAGTGACTCGTGAC (SEQ ID NO: 21) |
| Ce13d-G12* | TTTCGCCATAGGTCAAAGGTG*GGTGCGAGTTTTTACTCGTTATAGTGACTCGTGAC (SEQ ID NO: 22) |
| Ce13d-G13* | TTTCGCCATAGGTCAAAGGTGG*GTGCGAGTTTTTACTCGTTATAGTGACTCGTGAC (SEQ ID NO: 23) |
| Ce13d-G14* | TTTCGCCATAGGTCAAAGGTGGG*TGCGAGTTTTTACTCGTTATAGTGACTCGTGAC (SEQ ID NO: 24) |
| Ce13d-G15* | TTTCGCCATAGGTCAAAGGTGGGT*GCGAGTTTTTACTCGTTATAGTGACTCGTGAC (SEQ ID NO: 25) | rA = riboadenosine
Q = Iowa Black ® FQ;
FAM = carboxyfluorescein;
*= PS modification.

Gel Electrophoresis.

The DNAzyme complexes were formed by annealing the FAM-labeled substrate and the enzyme at a molar ratio of 1:1.5 in buffer A (25 mM NaCl, 50 mM MES, pH 6). For a typical gel-based activity assay, a final concentration of 10 µM metal ions were incubated with 5 µL of 1 µM DNAzyme complex in buffer A for 30 min to 1 h. The samples were then quenched with 1× loading dye with 8 M urea and 2 mM EDTA and run in 15% dPAGE at 120V for 80 min. The gel images were taken with a ChemiDoc MP imaging system (Bio-Rad).

DNAzyme Beacon Assay.

The sensor kinetic studies were carried out with 96 well plates and monitored with a SpectraMax M3 microplate reader. The stock complex was formed by annealing the FAM-labeled substrate and the quencher-labeled enzyme with a molar ratio of 1:1.5 in buffer A. The stock complex was stored in −20° C. overnight before use. Each complex was further diluted with 25 mM HEPES buffer (pH 7.6). For each well, 100 µL of 50 nM FAM-Q DNAzyme was used. 1 µL of metal ion was added after 5 mM of background reading to initiate cleavage. The samples were continuously monitored after addition for at least 30 min with 25 s intervals.

Results and Discussion

PS-modified substrate. The Ce13d DNAzyme (FIG. 1B) contains a substrate strand with the ribo-adenosine (rA) being the cleavage site. The bottom strand is the enzyme. With a lanthanide ($Ln^{3+}$), the substrate is cleaved into two pieces. To measure its cleavage activity, the 3'-end of the substrate was labeled with a FAM (carboxyfluorescein). A gel-based assay was performed with the first row divalent transition metal, group 2B ions, $Mg^{2+}$ and $Pb^{2+}$. $Ce^{3+}$ was also included to represent $Ln^{3+}$. With the normal phosphate oxygen (PO) substrate, Ce13d was cleaved only with $Ce^{3+}$ and to a lesser extent with $Pb^{2+}$. With a single PS in the substrate at the linkage between rA and G (PS2) (FIG. 1A), the $Ce^{3+}$-dependent activity was significantly suppressed, cleaving only ~5%. At the same time, high activity appeared with thiophilic metals ($Cu^{2+}$, $Cd^{2+}$, $Hg^{2+}$ and $Pb^{2+}$), while very low activity was observed with $Fe^{2+}$ and $Zn^{2+}$. All the other metals remained inactive. The influence of the PS modification on shifting the metal preference was clear.

Figure 2A:
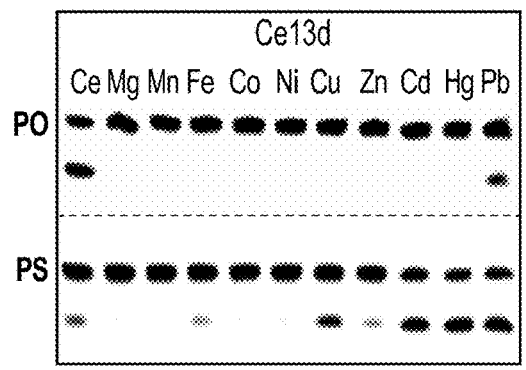
FIG. 2 illustrates gel images of the four DNAzymes with different metal ions and PO or PS substrate (A-D), schemes of the Ce13d DNAzyme substrate with different sites of the PS modification (denoted by the stars) (E), and gel image of the PS-modified substrates with the Ce13d DNAzyme in the presence of different metal ions (F).
Figure 2B:
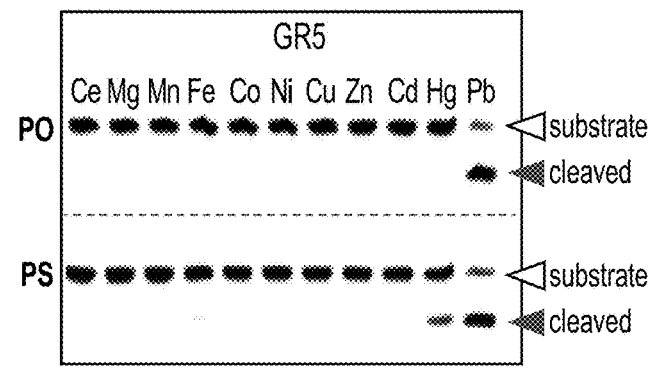
Figure 2C:
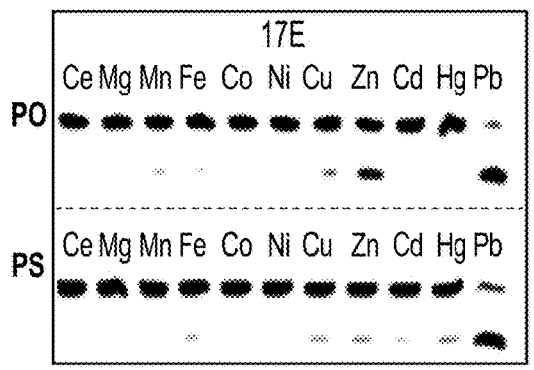
Figure 2D:
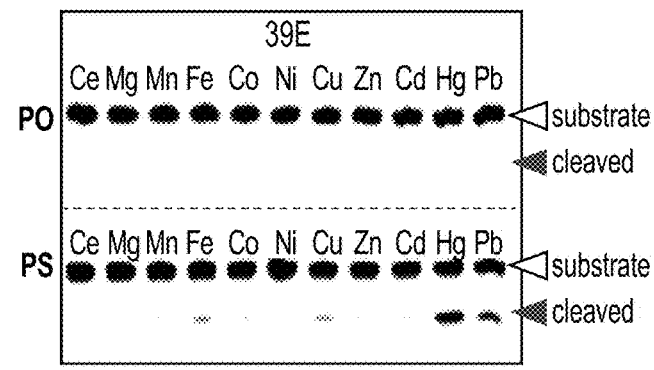
Figure 2E:
Figure 2F:
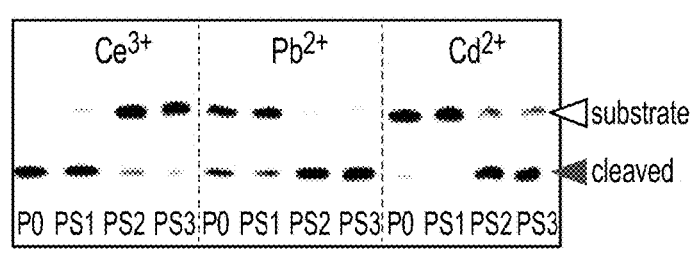

To confirm specificity of the PS modification, control substrates were also tested in which the PS was placed on the neighboring linkage (PS1) or dual PS modifications were introduced (PS3) (see FIG. 2E). $Ce^{3+}$, $Cd^{2+}$, and $Pb^{2+}$ were tested (FIG. 2F). PS1 behaved similar to the original PO substrate, indicating that the PS modification at this site has no effect. PS3 behaved similar to PS2, therefore implying that metal coordination to the phosphate at the cleavage site (FIG. 1A) is crucial. The $Ce^{3+}$ activity was suppressed with the PS2 substrate, which could be rescued by using thiophilic metals. From the analytical standpoint, Ce13d/PS2 is useful for detecting each of these toxic metals as a group.

PS-Modified Enzymes.

Previous studies indicate that the nucleotides in the Ce13d enzyme loop (FIG. 1B, in black) are highly conserved and crucial for activity. To test whether their phosphates are involved in metal binding, each linkage was systematically PS-modified (FIG. 3A). Together with the unmodified enzyme (PO), a total of 16 enzymes were tested as above with $Ce^{3+}$, $Cd^{2+}$, and $Pb^{2+}$. Gel images of the results are shown in FIG. 3. The first lane is substrate alone, the second lane is with the normal PO enzyme and the remaining lanes 1-15 are the PS modified enzymes as shown in FIG. 3A. Interestingly, in all cases, $Ce^{3+}$ and $Pb^{2+}$ showed similar activity (FIG. 3B, D), while $Cd^{2+}$ was completely inactive (FIG. 3C). Therefore, the phosphates in the enzyme loop are unlikely to bind the metal and the additional ligands may be from the nucleobases in the loop. This enzyme loop is rich in guanine and adenine; both are good ligands for lanthanides. Overall, the PS modification at the cleavage junction has the largest effect in shifting metal preference.

Other PS-Modified DNAzymes.

Ce13d detects thiophilic metals as a group. The four examples in FIG. 1 represent the main independent and well characterized metal-specific DNAzymes. For the GR5 DNAzyme, indeed only $Pb^{2+}$ cleaved the normal PO substrate (FIG. 2B). When the PS2 substrate was used, $Hg^{2+}$ was also slightly active. Therefore, with this pair of DNAzymes, we can already identify $Pb^{2+}$ and $Hg^{2+}$ with high confidence. The 17E DNAzyme is the most active with a low concentration of $Pb^{2+}$, and $Zn^{2+}$ can also assist cleavage (FIG. 2C). Interestingly, it becomes slightly more selective for $Pb^{2+}$ over $Zn^{2+}$ with the PS substrate. Since 39E is highly selective for $UO_2^{2+}$, none of the tested metals was active with the normal PO substrate, but $Hg^{2+}$ and $Pb^{2+}$ were active with the PS substrate.

Thus, Ce13d can be activated by all thiophilic metals with the PS substrate. All the other DNAzymes are only active with $Pb^{2+}$ and $Hg^{2+}$ under the same conditions. It is likely that Ce13d has a general metal binding site that is not available in other DNAzyme.

Metal Sensor Array.

Figure 4A:
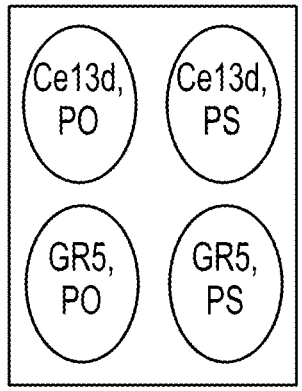
FIG. 4 illustrates a scheme of a four-component sensor array (A), with a flow chart of detecting $Hg^{2+}$, $Pb^{2+}$ and $Cd^{2+}$ based on reaction with Ce13d and GR5 DNAzymes and the PO and PS substrates (B), and a schematic showing the DNAzyme beacon sensor design (C).
Figure 4C:
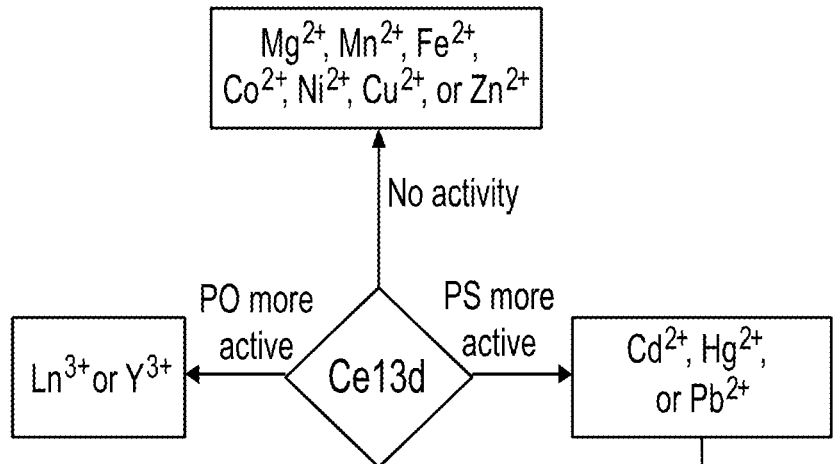
Figure 4C:
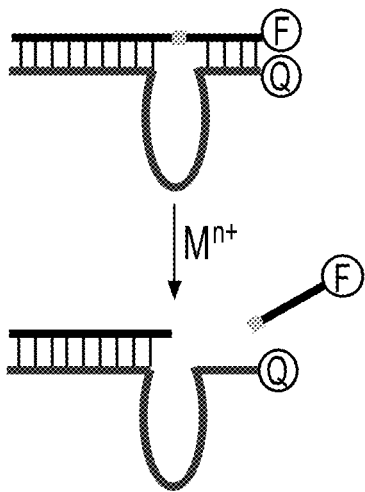

With the above results, a sensor array was made (FIG. 4A) to individually detect $Cd^{2+}$, $Hg^{2+}$ and $Pb^{2+}$ (i.e. toxic heavy metals). Based on the activity of Ce13d (FIG. 4A), the metal ions were separated into three groups. If it is inactive with either the PO or PS substrate, the sample might contain no divalent metals or only the first row transition metals. $Cu^{2+}$ and $Zn^{2+}$ were included in this group based on the subsequent biosensor assays (FIG. 4C, vide infra). On the other hand, if it is more active with the PO substrate, the metal is $Ln^{3+}$ or $Y^{3+}$. Otherwise, if it is more active with the PS substrate, the sample contains the three toxic metals. Among these three, $Pb^{2+}$ and $Hg^{2+}$ could be identified based on the response of the GR5 DNAzyme. After ruling out these two, the only one left is $Cd^{2+}$. We did not include 17E or 39E in the array since their information is redundant. The key component is Ce13d, which can narrow down the metals to a group of only three.

Figure 4B:
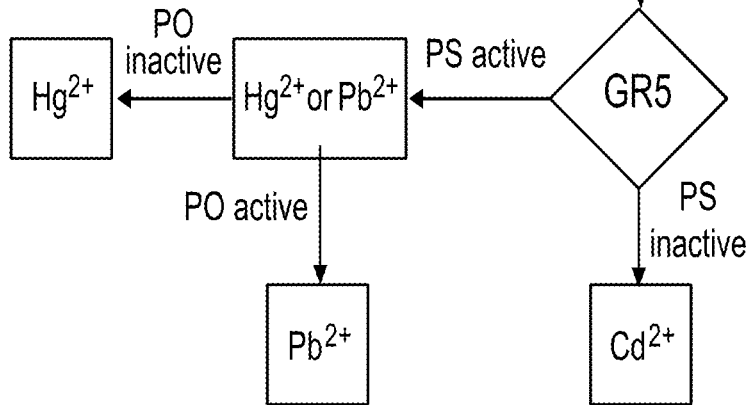
Figure 5A:
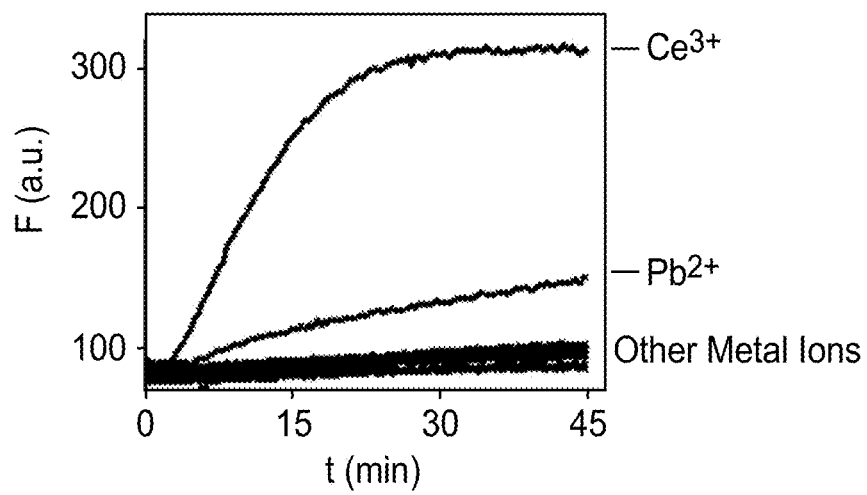
FIG. 5 illustrates sensor signaling kinetic traces with different metal ions using the Ce13d/PO (A) or Ce13d/PS (B) as a sensor. Quantification of the rate of fluorescence increase with various concentrations of different metal ions with the Ce13d/PO sensor (C) or Ce13d/PS sensor (D), and their difference (E). Rate of fluorescence increases with various concentrations of different metal ions with the GR5/PO (F) or GR5/PS (G) sensor.
Figure 5B:
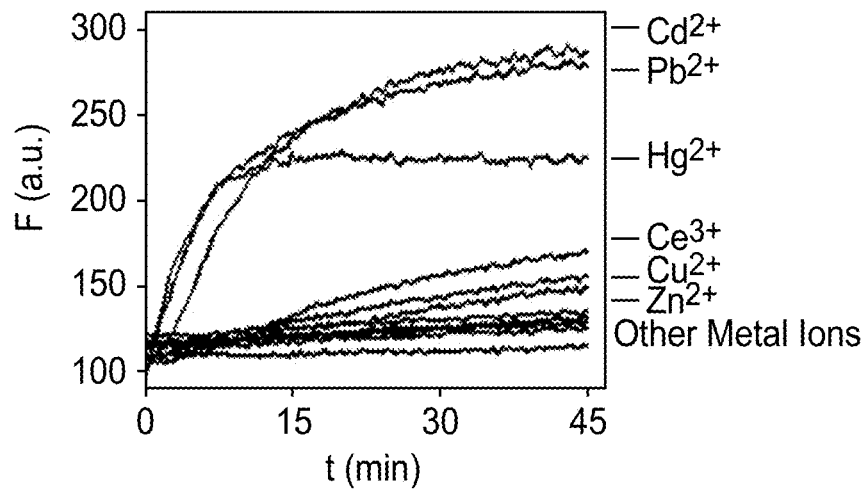
Figure 5C:
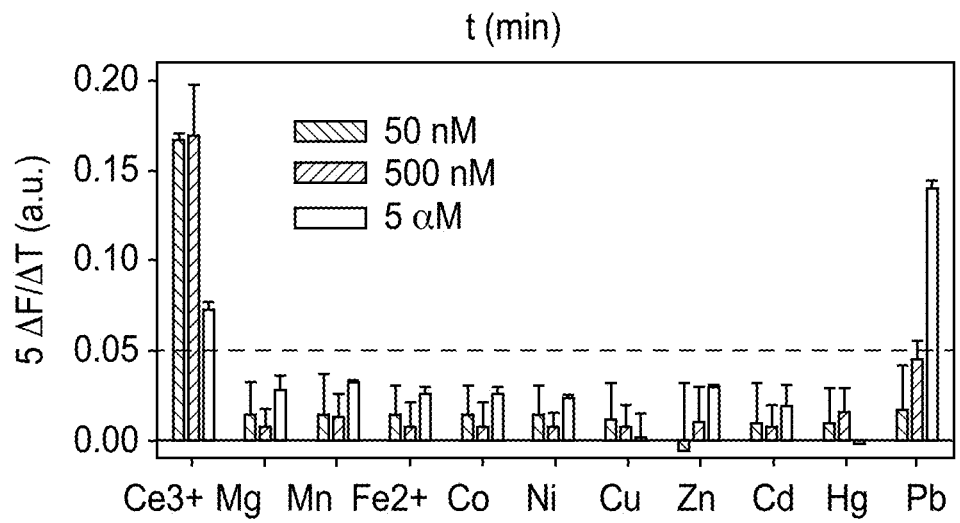
Figure 5D:
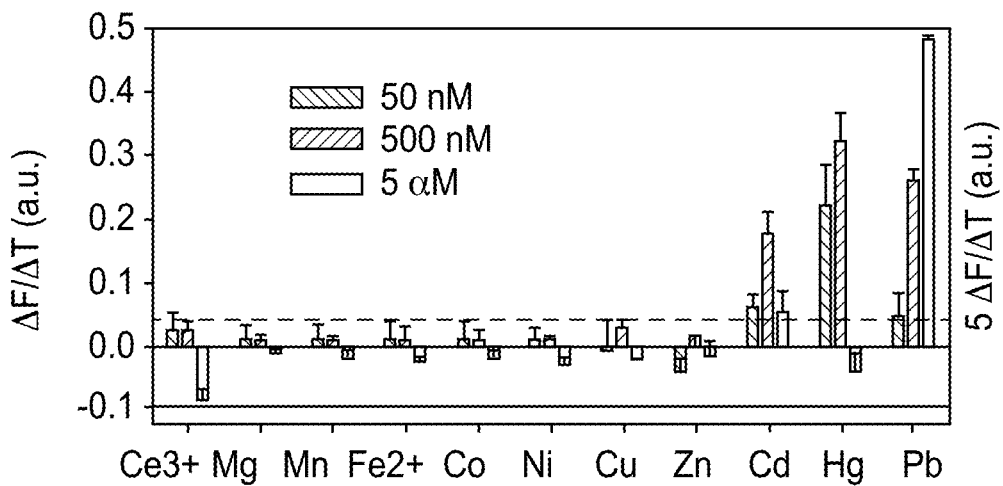
Figure 5E:
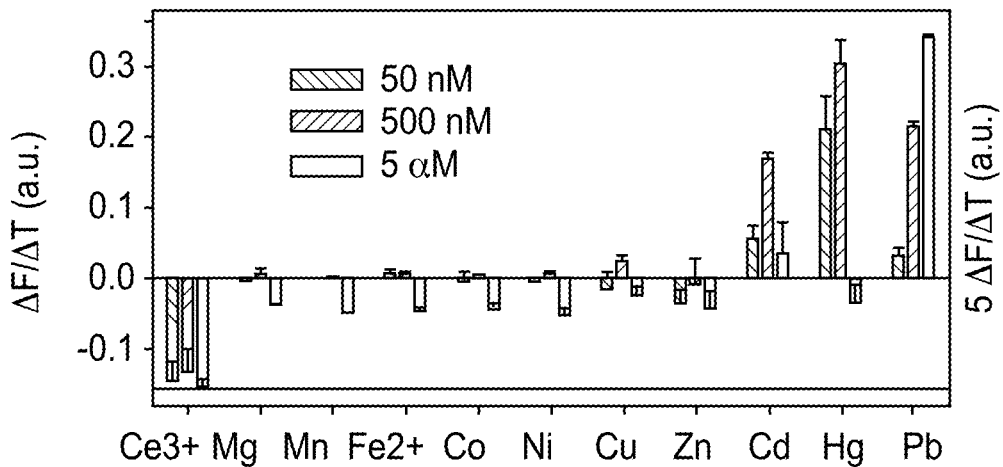

Since all the DNAzymes share the same substrate sequence, a common DNAzyme beacon strategy was employed for signaling. The beacons were made by hybridizing a quencher labeled enzyme with the FAM-labeled substrate (FIG. 4C). Enhanced fluorescence is observed after cleavage. With 500 nM metal, the response of the Ce13d/PO sensor is shown in FIG. 5A, where only $Ce^{3+}$ and $Pb^{2+}$ showed activity, consistent with the gel-based assay. The initial slope of the kinetic trace is plotted in FIG. 5C. To have a complete understanding, three metal concentrations from 50 nM to 5 µM were tested. Using a rate of 0.05 units as cut-off, only $Ce^{3+}$ and $Pb^{2+}$ showed response. With the Ce13d/PS sensor, $Cd^{2+}$, $Hg^{2+}$ and $Pb^{2+}$ showed the highest response (FIG. 5B), which is also consistent with the gel-based assay. On the other hand, $Cu^{2+}$ was more active in the gel assay than $Ce^{3+}$, but in the sensor, their responses were similar. This is attributed to fluorescence quenching effect of $Cu^{2+}$. With this sensor, only $Cd^{2+}$, $Hg^{2+}$ and $Pb^{2+}$ were active with a cut-off value of 0.05. FIG. 5E is obtained by subtracting the PO response from the PS data, where a clear separation of the three groups can be observed: $Ce^{3+}$ as one group, $Cd^{2+}$, $Hg^{2+}$ and $Pb^{2+}$ as the second group and the rest being the third, supporting the classification in FIG. 4B.

Figure 5F:
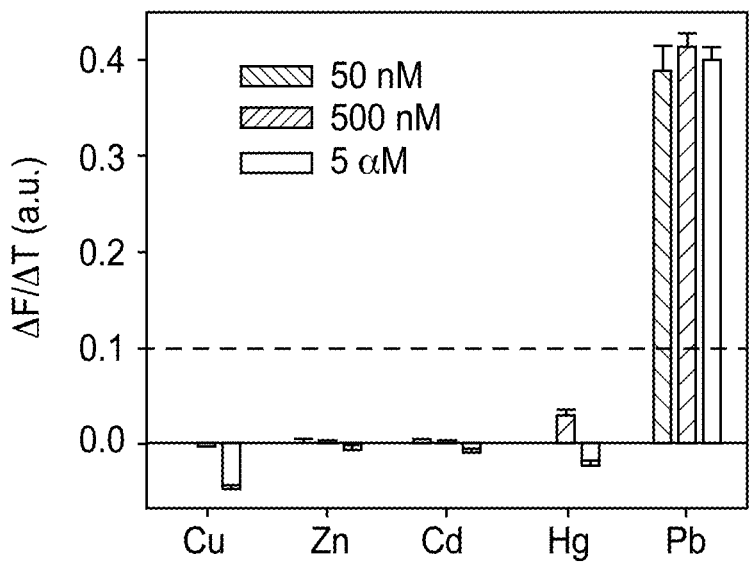
Figure 5G:
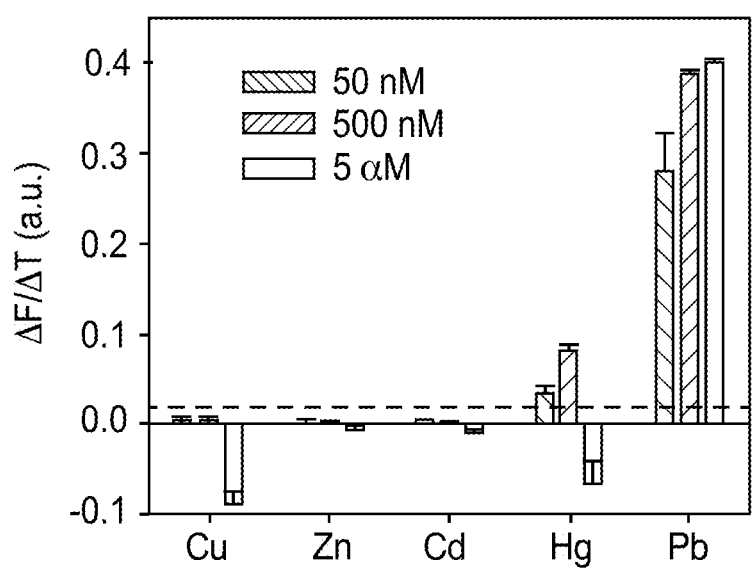

Since the other component of this test is GR5, the same assay was performed with it. With the GR5/PO sensor, only $Pb^{2+}$ was active using 0.1 unit as the cut-off (FIG. 5F). With the GR5/PS sensor and 0.02 as the cut-off (FIG. 5G), $Hg^{2+}$ and $Pb^{2+}$ are the active ones. $Hg^{2+}$ induced significant quenching at 5 μM and appeared inactive from the sensors (see Figure S2 for the kinetic traces).

Individual Sensor Performance.

Figure 6A:
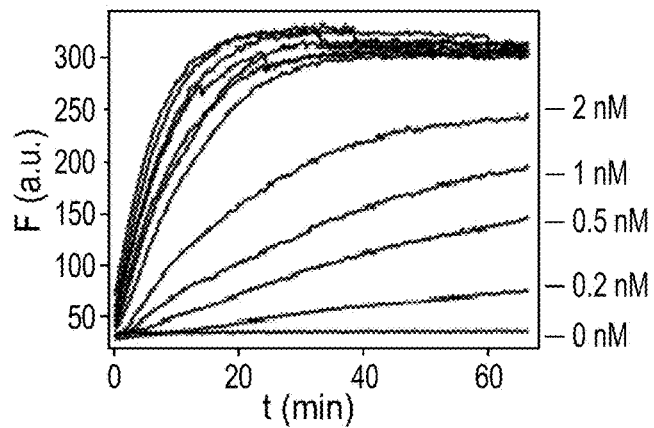
FIG. 6 graphically illustrates the kinetics of sensor fluorescence increase with the GR5/PO DNAzyme with $Pb^{2+}$ (A), Ce13d/PS with $Cd^{2+}$ (C) and Ce13d/PS with $Hg^{2+}$ (E). The initial rates of fluorescence increase as a function of $Pb^{2+}$ (B), $Cd^{2+}$ (D) and $Hg^{2+}$ (F) concentration. Insets: the responses to low metal concentrations.

Once a metal is identified, one of the sensors may be used for quantification. By far, GR5 is the best sensor for $Pb^{2+}$ with a previously reported detection limit was 3.7 nM (in pH 7.0 HEPES buffer). Significantly improved activity was observed at pH 7.6. For all the tests, the DNAzyme concentration was 50 nM in pH 7.6 HEPES buffer. The $Pb^{2+}$-dependent fluorescence kinetic traces are shown in FIG. 6A, where even 0.2 nM $Pb^{2+}$ is clearly distinguished from the background. With 5 nM $Pb^{2+}$, full cleavage was observed in 30 min. Since DNAzyme concentration was 50 nM, each $Pb^{2+}$ turned over 10 sensor molecules in 30 min to amplify the signal, highlighting the advantage of using DNAzyme for metal detection.

Figure 6B:
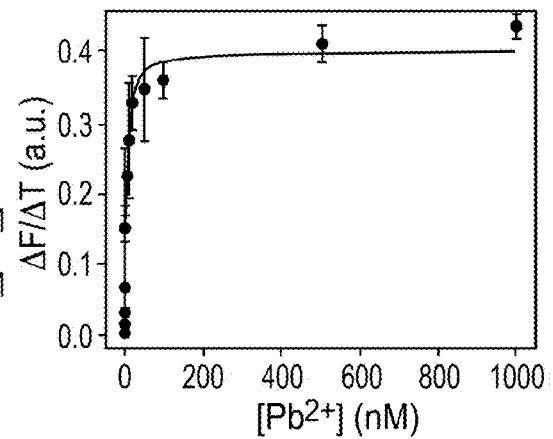
Figure 6C:
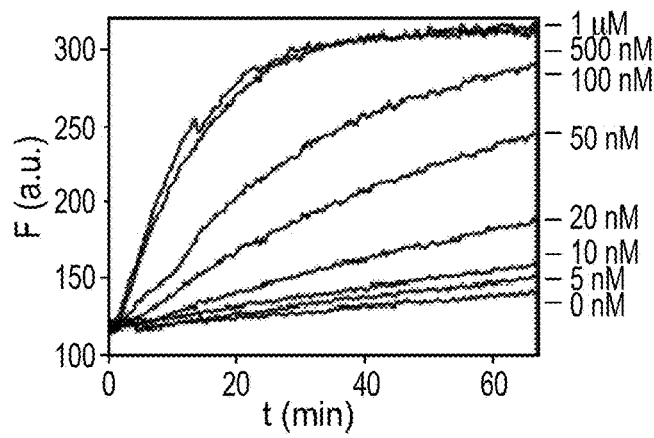
Figure 6D:
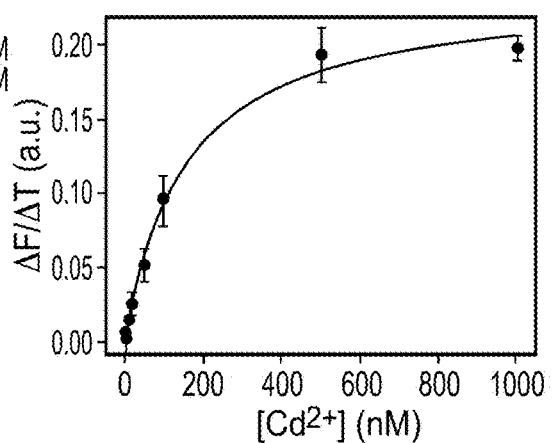
Figure 6E:
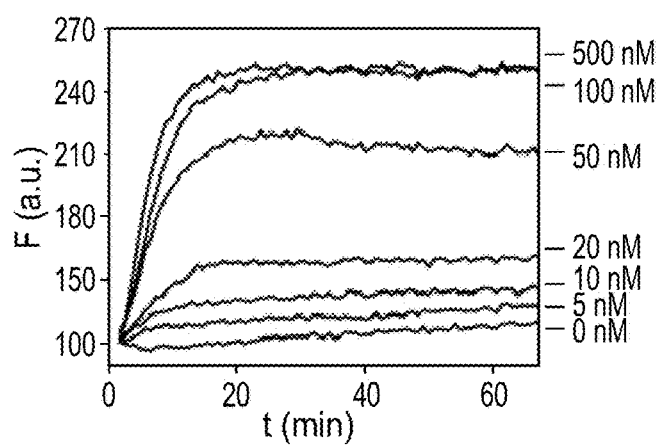
Figure 6F:
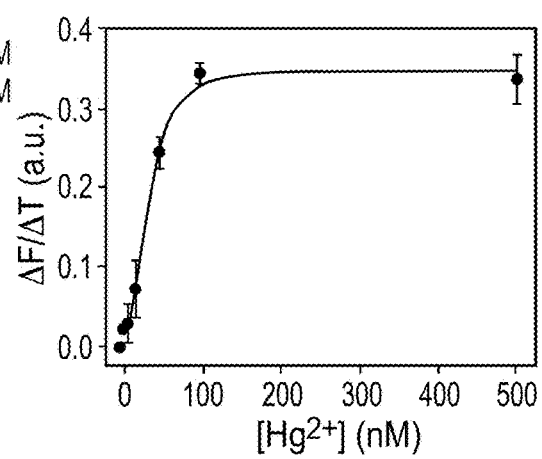

The calibration curve is shown in FIG. 6B; an apparent dissociation constant ($K_d$) of 4.2 nM $Pb^{2+}$ was obtained. This is the tightest metal binding in DNAzymes reported to date. The detection limit was 0.1 nM $Pb^{2+}$ from 3σ/slope, where σ is the standard deviation of background variation. $Cd^{2+}$ detection was carried out using the Ce13d/PS sensor (FIG. 6C, D). It has an apparent $K_d$ of 154 nM $Cd^{2+}$, and the detection limit was 4.8 nM $Cd^{2+}$. Finally, the Ce13d/PS sensor was also tested for $Hg^{2+}$ (FIG. 6E, F) and the detection limit was determined to be 2 nM. The US Environmental Protection Agency (EPA) maximal contamination limits are 15 ppb (72 nM) for $Pb^{2+}$, 5 ppb (45 nM) for $Cd^{2+}$, and 2 ppb (10 nM) for $Hg^{2+}$. Thus, each of sensors tested meet these limits of target detection, and in fact, exhibit a level of parts-per-trillion detection.

Example 2—$Cd^{2+}$-dependent DNAzyme

A biosensor for $Cd^{2+}$ was developed with ultrahigh sensitivity and specificity based on $Cd^{2+}$-dependent DNAzyme selections using a PS modified library. Since each PS produces two diastereomers, a DNAzyme-based method for the chiral assignment and separation was developed.

Materials and Methods
Chemicals.

The DNAs for selection (Table 2) and sensing were purchased from Integrated DNA Technologies (Coralville, Iowa). The cleavage site ribo-adenine is denoted by rA, FAM=carboxyfluorescein, iSp18 is an 18-atom hexa-ethyleneglycol spacer. The 5' of the Lib-rA* DNA is phosphorylated (denoted by the p) for the ligation reaction. The star (*) denotes phosphorothioate modification. The other DNAs (Table 3) were from Eurofins (Huntsville, Ala.). BHQ denotes Black Hole Quencher® 1, and p denotes phosphorylation. Most of these sequences are to test the activity of individual clones from the blocked negative selection. The metal salts were from Sigma-Aldrich at the highest available purity. Tris(hydroxymethyl)aminomethane (Tris), 2-(N-morpholino)ethanesulfonic acid (MES), 2-[4-(2-hydroxyethyl)piperazin-1-yl]ethanesulfonic acid (HEPES), EDTA, NaCl, and ammonium acetate were from Mandel Scientific (Guelph, Ontario, Canada). SsoFast EvaGreen supermix was from Bio-Rad. T4-DNA ligase, dNTP mix, Taq DNA polymerase, and DNA ladder were from New England Biolabs.

TABLE 2

DNA sequences related to in vitro selection in this work.

| DNA Name | Sequence and modifications (from 5' to 3') |
|---|---|
| Lib-FAM | pGGCGAAACATCTTN$_{50}$TAGTGACGGTAAGCTTGGCAC-FAM (SEQ ID NO: 26) |
| Lib-rA* | 5'-AATACGAGTCACTATrA*GGAAGAT (SEQ ID NO: 27) |
| Splint DNA | 5'-AAGATGTTTCGCCATCTTCCTATAGTCCACCACCA (SEQ ID NO: 28) |
| P1 primer | 5'-GTGCCAAGCTTACCG (SEQ ID NO: 29) |
| P2 primer | 5'-CTGCAGAATTCTAATACGAGTCACTATAGGAAGATGGCGAAACA (SEQ ID NO: 30) |
| P3 primer | 5'-FAM-AAATGATCCACTAATACGACTCACTATrA*GG (SEQ ID NO: 31) |
| P4 primer | 5'-AACAACAACAAC-iSp18-GTGCCAAGCTTACCG (SEQ ID NO: 32) |
| Blocking DNA1 | CGCACCTACCTTTGACCTATGG (SEQ ID NO: 33) |
| Blocking DNA2 | CGCACCCACCTTTGACCTATGG (SEQ ID NO: 34) |

TABLE 3

Other DNA sequences used in this study.

| DNA Name | Sequence and modifications (from 5' to 3') |
|---|---|
| BN-Cd13 | CGC CAT CTT CAA TIC GAT AGA GTC CAC GIC TAC AGG AAT GTG GGA AAT AGT GAC TCG TGA (SEQ ID NO: 35) |
| BN-Cd11 | TTT CGC CAT CTT CCT TCG ACA GCC CAG ATA GTG ACT CGT GAC (SEQ ID NO: 36) |

TABLE 3 -continued

Other DNA sequences used in this study.

| DNA Name | Sequence and modifications (from 5' to 3') |
|---|---|
| BN-Cd16 | TTT CGC CAT CTT CCT TCG ATA GTT AAA ATA GTG ACT CGT GAC (SEQ ID NO: 37) |
| BN-Cd23 | TTT CGC CAT CTT CCT TCG ATA GCC CAG ATA GTG ACT CGT GAC (SEQ ID NO: 38) |
| BN-Cd22 | TTT CGC CAT CTT TCT TCG ATA GTT AAG ATA GTG ACT CGT GAC (SEQ ID NO: 39) |
| BN-Cd04 | TTT CGC CAT CTT GAA ACG CAC GAA GAA TAG TGA CTC GTG AC (SEQ ID NO: 40) |
| BN-Cd40 | TTT CGC CAT CTA ACA GGA AAC ACT TTA GTG ACT CGT GAC (SEQ ID NO: 41) |
| BN-Cd18 | CGC CAT CTT TAC CCA AAA GGA AGG TTT TCT ATT TTT AGA AAC ACA GGA GTA GTG ACT CGT (SEQ ID NO: 42) |
| PS-Sub | GTC ACG AGT CAC TAT rA*GG AAG ATG GCG AAA-FAM (SEQ ID NO: 43) |
| PO-Sub | GTC ACG AGT CAC TAT rAGG AAG ATG GCG AAA-FAM (SEQ ID NO: 44) |
| Ce13d | TTTC GCC ATA GGT CAA AGG TGG GTG CGA GTT TTT ACT CGT TAT AGT GAC TCG T (SEQ ID NO: 45) |
| 17E | TTT CG CCA TCT TCT CCG AGC CGG TCG AAA TAG TGA CTC GTG AC (SEQ ID NO: 46) |
| FAM-Sub | FAM-AGT CACTAT rA*GG AAG ATG GCG AAC (SEQ ID NO: 47) |
| Q-BN-Cd16 | GTT CGC CAT CTT CCT TCG ATA GTT AAA ATA GTG ACT-BHQ (SEQ ID NO: 48) |
| HPLC-splint | AAA AAA AAA ATT TCG CCA TCT TCC TAT AGT GAC TC (SEQ ID NO: 49) |
| HPLC-5' | GAGTCACTATrA*GG (SEQ ID NO: 50) |
| HPLC-3' | pAAGATGGCGAAA-FAM (SEQ ID NO: 51) |

In Vitro Selection.

Figure 7:
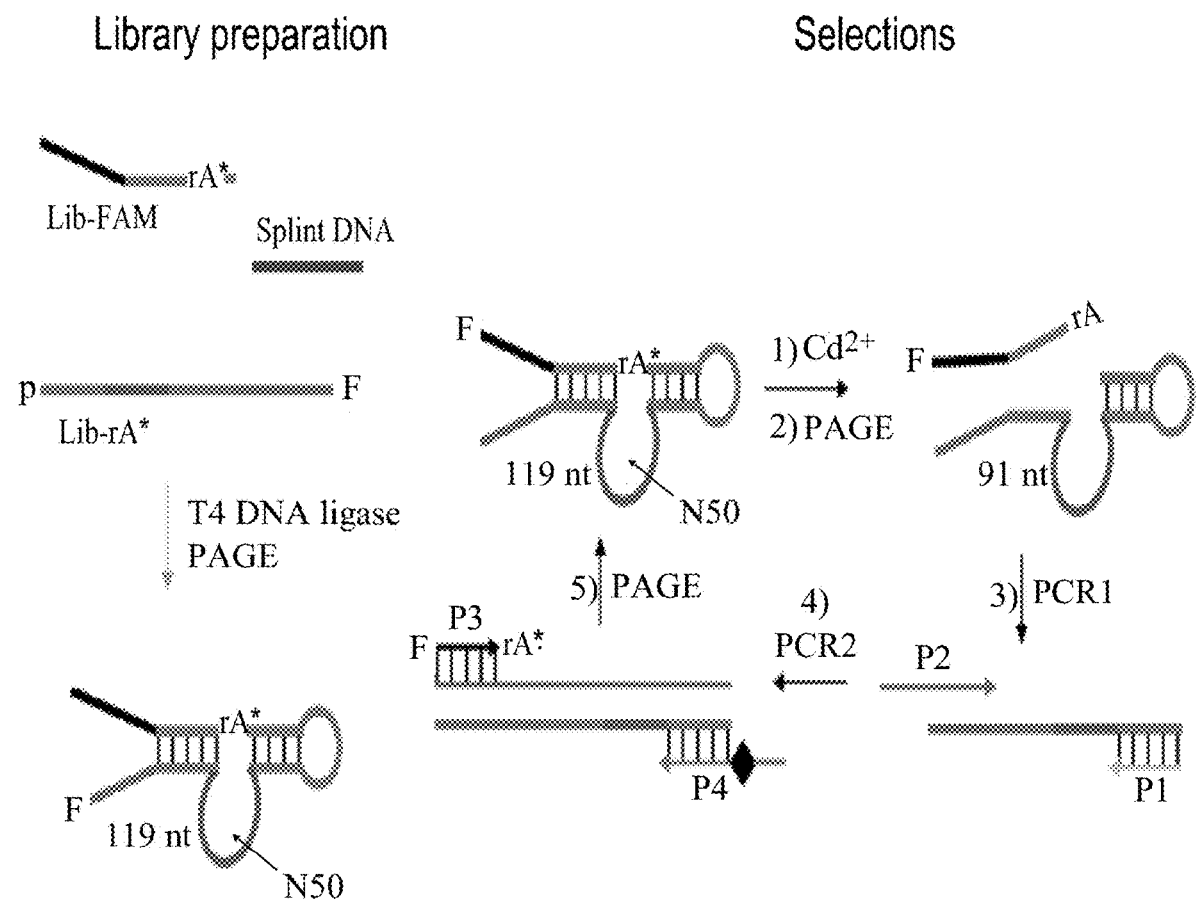
FIG. 7 illustrates the scheme of direct in vitro selection of $Cd^{2+}$-dependent PS-modified DNAzymes.

FIG. 7 shows the selection scheme used. The initial library was prepared by ligating Lib-FAM (0.2 nmol) and Lib-rA* (0.3 nmol) with a splint DNA (0.3 nmol) using T4 ligase following the vendor's protocol. The ligated DNA was purified with 10% dPAGE and extracted from the gel with buffer B (1 mM EDTA, 10 mM Tris-HCl, pH 7.0). After ethanol precipitation, the library was re-suspended in 60 pit buffer C (50 mM MES, pH 6.0, 25 mM NaCl) and used for the first round of selection. For each subsequent round, the library was generated from PCR. For blocked selection, before each selection step, the library was annealed with 150 pmol of each of the two blocking DNAs to inactivate the Ce13 related sequences. After incubating with $Cd^{2+}$ (see Table 4 for incubation time and metal concentration), the reaction was quenched with 8 M urea and the cleaved product was purified by 10% dPAGE. The selected DNA was extracted from the gel, desalted with a Sep-Pak C18 column (Waters), and then suspended in 70 μL HEPES buffer (5 mM, pH 7.5). Two PCR steps were used to amplify the selected DNA. In PCR1, P1 and P2 primers were used and in PCR2, P3 and P4 were used as described previously (Huang et al. (2015) *Nucleic Acids Res.*, 43, 461-469). For negative selections, the library was treated with a metal mixture containing $Zn^{2+}$, $Pb^{2+}$ and $Cu^{2+}$ (20 μM each). The uncleaved oligonucleotides were harvested for a positive selection with $Cd^{2+}$.

TABLE 4

In vitro selection conditions.

| Round | [$Cd^{2+}$] (μM) | Incubation time (min) |
|---|---|---|
| Selection 1. Direct selection | | |
| 1 | 50 | 60 |
| 2 | 50 | 60 |
| 3 | 50 | 60 |
| 4 | 50 | 60 |
| 5 | 50 | 30 |
| 6 | 50 | 15 |
| Selection 2. Blocked selection | | |
| 1 | 50 | 60 |
| 2 | 50 | 60 |
| 3 | 50 | 60 |
| 4 | 50 | 60 |
| 5 | 50 | 60 |
| 6 | 50 | 40 |
| 7 | 50 | 40 |
| Selection 3. Blocked selection with negative selections | | |
| Round | [$Zn^{2+}$, $Cu^{2+}$, $Pb^{2+}$] (−) or [$Cd^{2+}$] (+) (μM) | Incubation time (min) |
| 8 (−) | 50 | 60 |
| 8 (+) | 50 | 30 |
| 9 (−) | 50 | 120 |
| 9 (+) | 50 | 20 |
| 10 (−) | 20 | 120 |
| 10 (+) | 50 | 10 |
| 11 (−) | 20 | 240 |
| 11 (+) | 50 | 5 |
| 12 (−) | 10 | 120 |
| 12 (+) | 50 | 5 |
| 13 (−) | 10 | 120 |
| 13 (+) | 50 | 5 |

TABLE 4-continued

In vitro selection conditions.

| 14 (−) | 10 | 1440 |
| 14 (+) | — | — |
| 15 (−) | 10 | 240 |
| 15 (+) | 50 | 5 |

Sequencing.

Three DNA sequencing experiments were performed. For each one, the PCR1 product was cloned using the TA-TOPO cloning kit (Life Technologies) and transformed into Efficiency DH5α competent cells following the vendor's protocol. The plasmid DNA was extracted and purified using DirectPrep 96 miniprep kit (QIAGEN). The extracted DNA was submitted to TCAG DNA Sequencing Facility (Toronto, ON).

Enzyme Assays.

Gel-based assays were performed with FAM-labeled PS substrate (0.7 µM) and enzyme (1.1 µM) annealed in buffer C. A final of 10 µM $Cd^{2+}$ (or other metals/concentrations) was added to initiate the cleavage reaction. The products were separated on a dPAGE gel and analyzed using a ChemiDoc MP imaging system (Bio-Rad). All the assays were run at least in duplicate.

HPLC Separation of Diastereomers.

An Agilent 1260 Infinity Quaternary HPLC system with an Inspire C18 column (5 µm, 250 mm×4.6 mm, Dikma) was used for diastereomer separation. The HPLC separation was carried out based on previously published protocols (Frederiksen et al. (2009) In Herschalag, D. (ed.), *Methods in enzymology*, vol 468. pp. 289-309). The 5'-half of the substrate containing the PS modification was injected at 20 µL, (100 µM) with a flow rate of 1 mL/min. The column was heated to 45° C. Two solvents were prepared for eluting the sample: solvent A 0.1 M $NH_4OAc$; solvent B=20% 0.1 M $NH_4OAc$ and 80% $CH_3CN$. From time 0 to 10 min, 97% solvent A and 3% solvent B were used. From 10 min to 90 min, solvent A was gradually decreased to 90%, while solvent B increased to 10%.

For the subsequent ligation reaction, HPLC-5', HPLC-3' and splint DNA were mixed at 1:1.5:1.5 ratio in buffer (10 mM $MgCl_2$, 50 mM Tris-HCl, pH 7.5). The mixture was annealed at 95° C. for 1 min followed by slow cooling to room temperature. The T4 ligation protocol provided by the vendor was followed. The ligated DNA product was purified with 15% dPAGE at 650V for 1.5 h, and DNA was extracted from the gel with buffer (1 mM EDTA, 10 mM Tris-HCl, pH 7.0). The extracted DNA was further desalted using a Sep-Pak C18 cartridge (Waters). The purified DNA was then lyophilized overnight and re-suspended in 5 mM HEPES (pH 7.5) for further analysis.

DNAzyme-Based Chiral Separation.

The FAM-labeled PS substrate (1 µM) was annealed with 17E or BN-Cd16 (3 µM) in buffer D (50 mM MOPS, pH 7.5, 25 mM NaCl) or buffer C, respectively. $MgCl_2$ (10 mM) was added to the 17E sample (overnight), while $CdCl_2$ (10 µM) was added to the BN-Cd16 sample (1 h). Both samples were then desalted with Sep-Pak columns, and the uncleaved substrate was separated by 10% dPAGE. After another desalting step, the purified substrate was re-suspended in 5 mM HEPES (pH7.5) and the DNA concentration was determined by Nanodrop 1000 (Thermo).

Biosensor Assays.

The sensing kinetics were measured in a 96-well plate using a microplate reader (M3, SpectraMax). The sensor complex was formed by annealing the FAM-labeled PS substrate (after 17E treatment) and the quencher-labeled enzyme (molar ratio=1:1.5) in buffer C. The final sensor concentration was 50 nM in 1 mM HEPES (pH 7.5, 100 µL, each well). 1 µL metal ion was added to initiate cleavage and the signaling kinetics was monitored (Ex=485 nm; Em=520 nm).

Detecting $Cd^{2+}$ in Rice.

White rice was obtained from a local supermarket and ground into a fine powder. The rice powder (500 mg) was loaded into a Pyrex tube and HCl (100 mM, 1 mL) was added. After cooking at 95° C. for 3 h, NaOH (100 mM, 1 mL) was added to neutralize the sample. After centrifugation at 15,000 rpm, the supernatant was collected. For detection, 2 µL of the extracted sample with various concentrations $Cd^{2+}$ was added into 98 µL sensor.

Results and Discussion

Direct Selections with a PS-Modified Library.

Figure 8A:
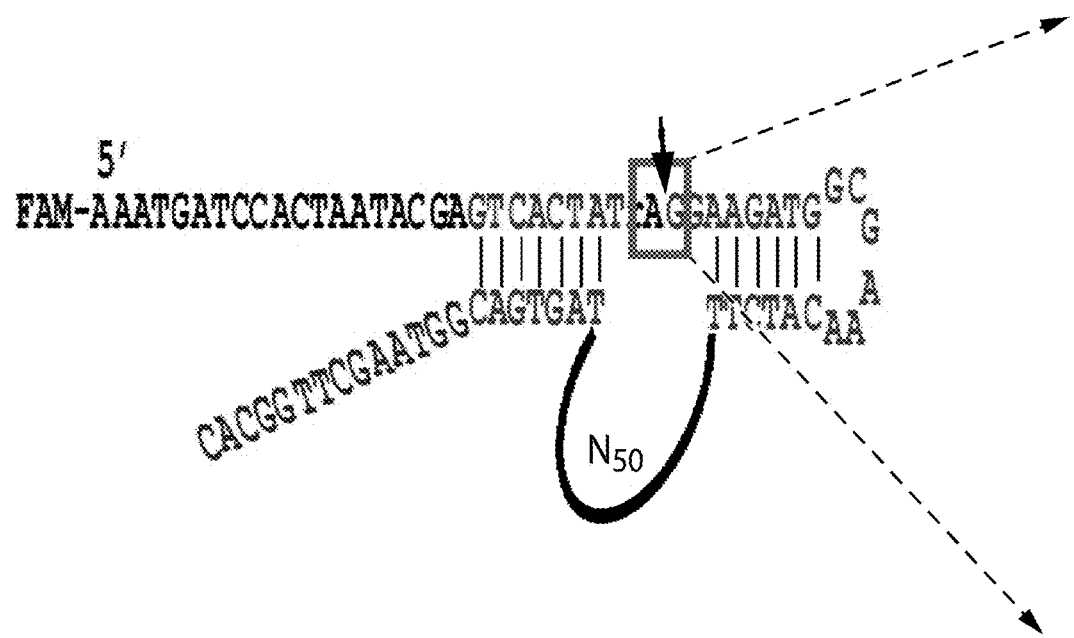
FIG. 8 illustrates the library sequence for the PS DNAzyme selection (A), and the structure of the cleavage junction (rAG), where rA denotes ribo-adenosine, in which a PS linkage is utilized (B). A representative sequence from the direct selection, where the blue/cyan nucleotides are from the randomized $N_{50}$ region (C) is shown. The star at the cleavage site represents the PS. This sequence is similar to Ce13. Two blocking sequences are complementary to the cyan region and they differ only by one base (underlined) (D). The progress of the direct (unblocked) and blocked selections is graphically illustrated (E). The red dots indicate the rounds for DNA sequencing.

To isolate $Cd^{2+}$-specific DNA, in vitro selection was carried out with a library containing 50 random nucleotides ($N_{50}$, ~$10^{14}$ random sequences, FIG. 8A). The cleavage site is indicated by the arrowhead at the single RNA (rA) position. This scissile bond is ~1-million-fold less stable compared to the rest of the DNA linkages. A PS modification was introduced at this cleavage junction (FIG. 8B) to increase affinity towards thiophilic $Cd^{2+}$.

In each round, $Cd^{2+}$ was added to induce cleavage. The cleaved oligonucleotides were harvested by gel electrophoresis and amplified by PCR to seed the next round of selection. Saturated activity was obtained after 5 rounds (FIG. 8E, black bars), yielding ~35% cleavage. The round 6 library was cloned and sequenced. Interestingly, 34 out of the 35 obtained sequences were similar to the Ce13 DNAzyme, which was first isolated in a lanthanide-dependent selection. A representative sequence (FIG. 8C) shows a hairpin (in blue) and a large loop (in cyan) that constitutes the catalytic core. Each individual clone may differ in the hairpin but the loop sequence was highly conserved. Since Ce13 is active with $Cd^{2+}$ using a PS-modified substrate, it is not surprising that it was isolated again. This result also suggests that Ce13 is a preferred (or easy-to-obtain) solution for $Cd^{2+}$-dependent PS RNA cleavage. However, this DNAzyme is not specific for $Cd^{2+}$ (e.g. also active with $Pb^{2+}$, $Cu^{2+}$, $Hg^{2+}$ and $Ce^{3+}$).

Blocked Selections.

Figure 8B:
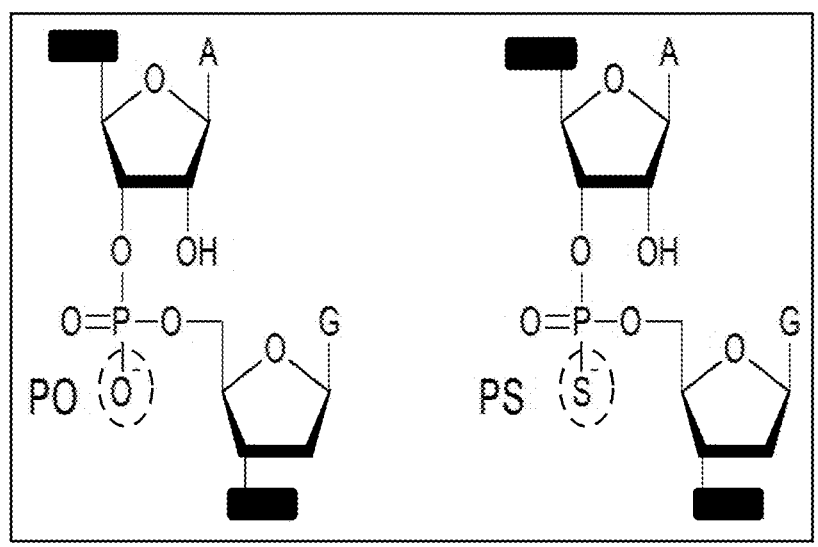
Figure 8C:
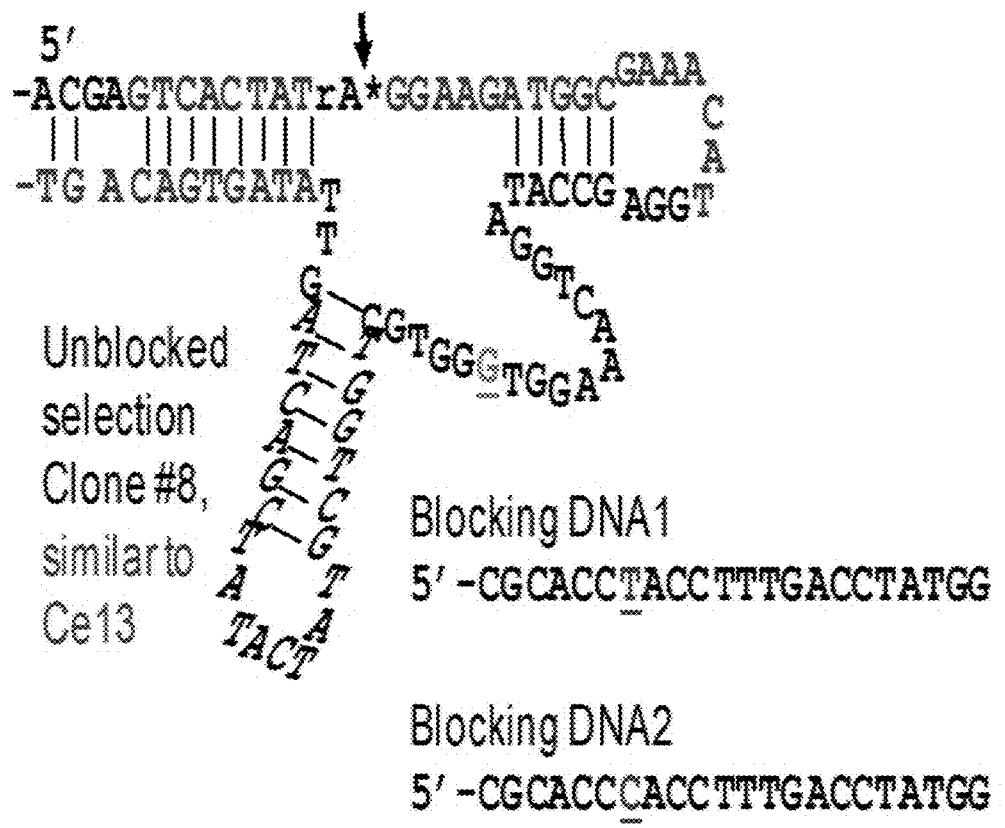
Figure 8D:
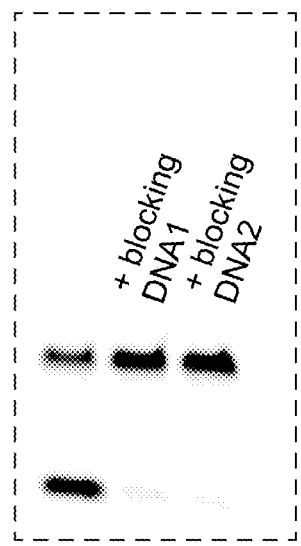
Figure 8E:
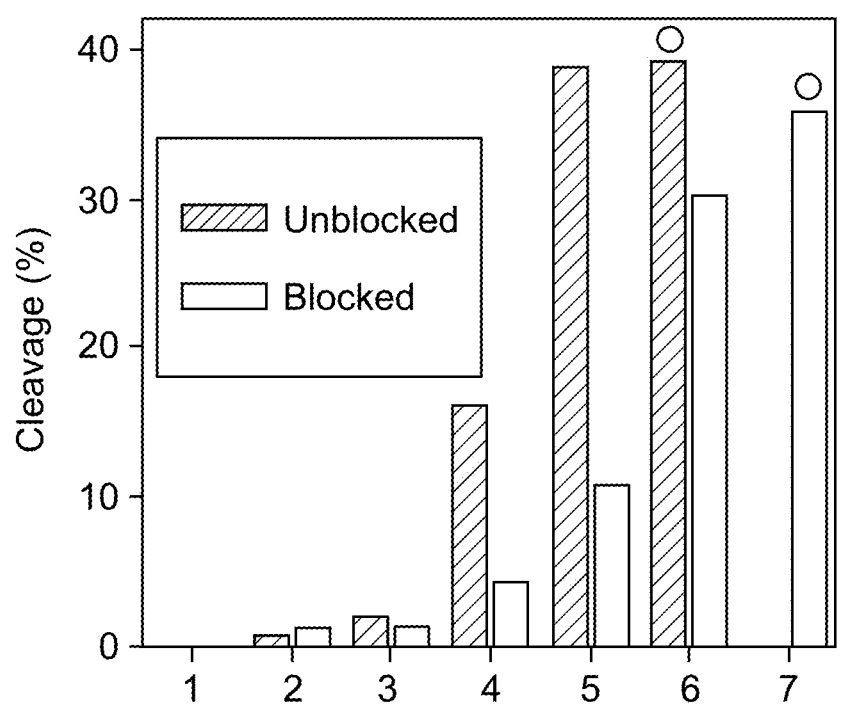
Figure 9A:
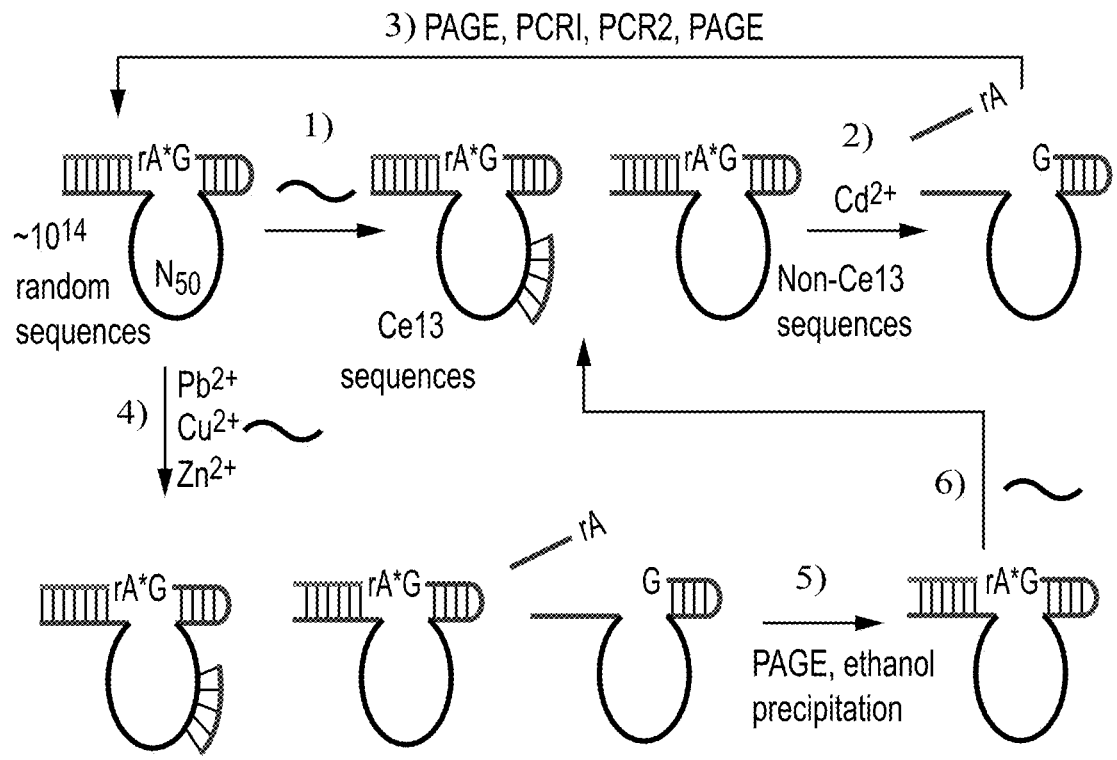
FIG. 9 illustrates (A) a scheme for the blocked and negative selection to develop novel DNAzymes; (B) selection progress from round 8 of the blocked selection. For each round, both positive and negative selections were carried out. The round 15 library was sequenced; (C) a trans-cleaving DNAzyme derived from BN-Cd16 and (D) alignment of the enzyme loop for sequences similar to BN-Cd16.

To isolate a new DNAzyme, a re-selection was performed. Ce13 is active with lanthanides and $Pb^{2+}$ (without the PS modification). Therefore, if the library is not PS-modified, it is unlikely that Ce13 could be isolated. The conserved sequence of Ce13 is quite long (e.g. the 15 nucleotides in cyan in FIG. 8C). Only one of the nucleotides (marked by underline) may change from G to A. It was hypothesized that the library might be evolved against this sequence by using blocking DNA complementary to these conserved nucleotides. Two blocking DNAs were designed as shown in FIG. 8C which completely inactivate the Ce13 DNAzyme (FIG. 8D). In the new selection scheme (FIG. 9A), an excess amount of blocking DNA (150 pmol) was first hybridized with the library to inactivate the Ce13 sequence (step 1). Then, $Cd^{2+}$ was added (step 2) and the cleaved oligonucleotides were amplified (step 3). It took 7 rounds to reach activity plateau (FIG. 8B, gray bars). This is probably due to suppression of the highly active Ce13 population. The round 7 library was sequenced and the Ce13 variants were indeed eliminated. This enriched library, however, had a high sequence diversity, suggesting that many solutions for $Cd^{2+}$-dependent cleavage are available. After treating the round 7 library with a metal mixture ($Pb^{2+}$, $Cu^{2+}$ and $Zn^{2+}$, 20 µM each), nearly 60% cleavage occurred after 1 h, indicating this library still lacked specificity for $Cd^{2+}$.

Blocked Negative Selections.

Figure 9B:
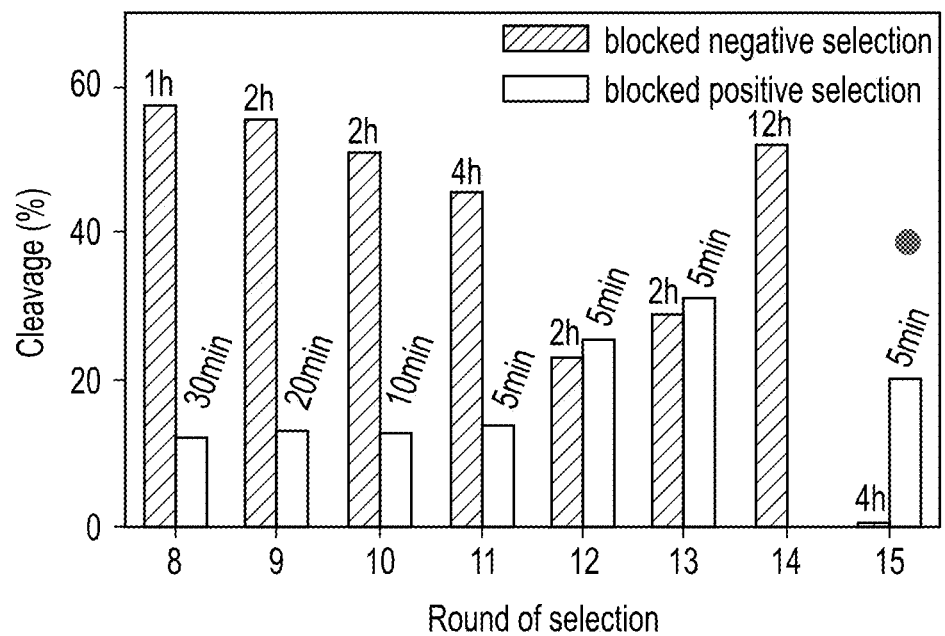

The competing metals were all thiophilic, which may explain their activity. After incubating with a metal mixture ($Pb^{2+}$, $Zn^{2+}$, and $Cu^{2+}$, step 4, FIG. 9A), the cleaved oligonucleotides were discarded and the remaining uncleaved library was harvested (step 5). Then the library was incubated with $Cd^{2+}$ for the positive selection (step 2). To achieve high specificity, stringent conditions were used for the negative selection by extending reaction time (FIG. 9B, black bars). The activity of the competing metals went down from 58% cleavage in 1 h in round 8 to ~30% in 2 h in round 13. A 12 h incubation followed by a 4 h incubation was then conducted. At the end (round 15), very little cleavage with the metal mixture was observed, suggesting a significant selectivity improvement.

To ensure high activity, the reaction time was shortened for the positive $Cd^{2+}$-dependent selections. In the last four rounds, the reaction time was only 5-min and ~20% cleavage was consistently achieved (FIG. 9B, red bars). At round 15, since both the negative and positive activities were optimized, this library was sequenced.

DNAzyme Secondary Structure Analysis.

Figures 9C, 9D:
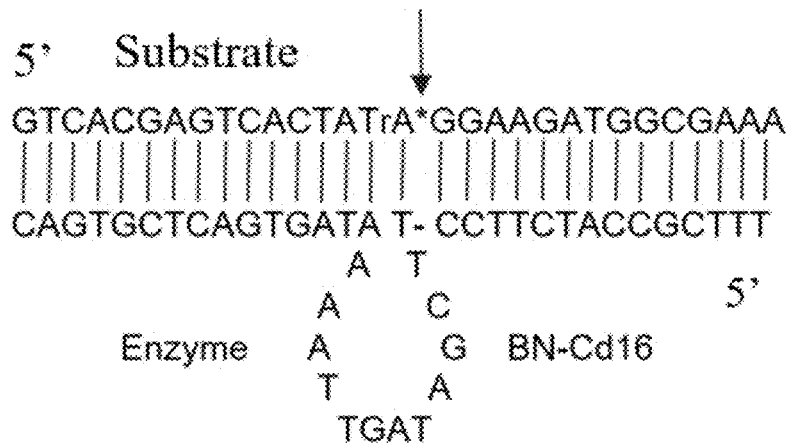

Out of the 37 sequences, 19 are aligned to a single family, and a representative sequence is clone #16, its trans-cleaving structure being shown in FIG. 9C, where the redundant nucleotides are removed. The enzyme loop is very small, containing only 12 nucleotides. This loop sequence is well aligned (FIG. 9D): the underlined nucleotides are highly conserved; the bolded nucleotides can be changed from purine to purine or from pyrimidine to pyrimidine, while the two remaining nucleotides are more variable. Overall, this appears to be a well-defined new DNAzyme.

High $Cd^{2+}$ Specificity.

Figure 10A:
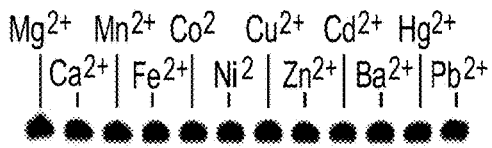
FIG. 10 illustrates the results of biochemical characterization of the BN-Cd16 DNAzyme including gel images of BN-Cd16 with the PS substrate reacting (A) in the presence of 10 µM various metals after 10 min incubation, and (B) with 10 µM $Cd^{2+}$ as a function of time; (C) Kinetics of the PS substrate cleavage by BN-Cd16 with different metal ions (10 µM); (D) Comparison of rate of cleavage of BN-Cd16 and Ce13d with the PS substrate; (E) Comparison of the fraction of cleavage by $Hg^{2+}$ (10 µM) with these two DNAzymes; (F) Cleavage percentage with three concentrations of various competing metals; and (G) Fraction of cleavage after 15 min as a function of $Cd^{2+}$ concentration. All the assays were run in 50 mM MES buffer (pH 6.0) with 25 mM NaCl.

A few sequences in FIG. 9D were tested, and they all have similar $Cd^{2+}$-dependent activity, confirming the sequence alignment. The #16 sequence was chosen for further studies (named BN-Cd16 or Cd16 in short). Its metal specificity was first measured with 10 µM divalent metal ions (FIG. 10A), and $Cd^{2+}$ indeed shows the best cleavage. Moderate activity was observed with $Cu^{2+}$, $Pb^{2+}$ and $Hg^{2+}$, while none of the other metal ions produced any cleavage up to 1 mM (FIG. 10F). In particular, the $Cd^{2+}$ selectivity over $Zn^{2+}$ was more than 100,000-fold based on their cleavage rates. Therefore, BN-Cd16 solves the challenging problem of separating $Cd^{2+}$ and $Zn^{2+}$.

Figure 10B:
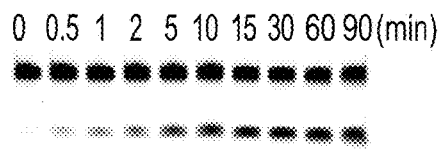
Figure 10C:
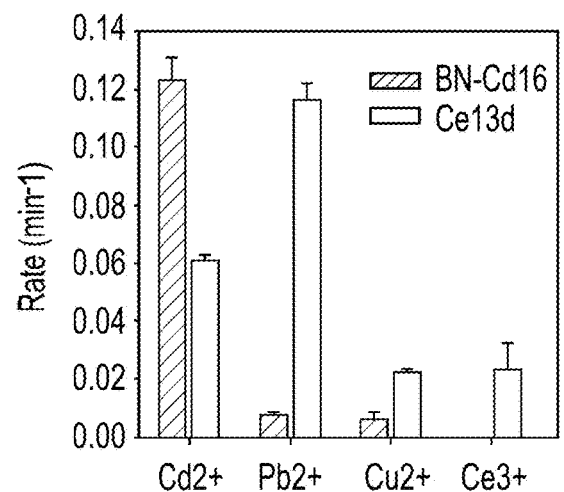
Figure 10D:
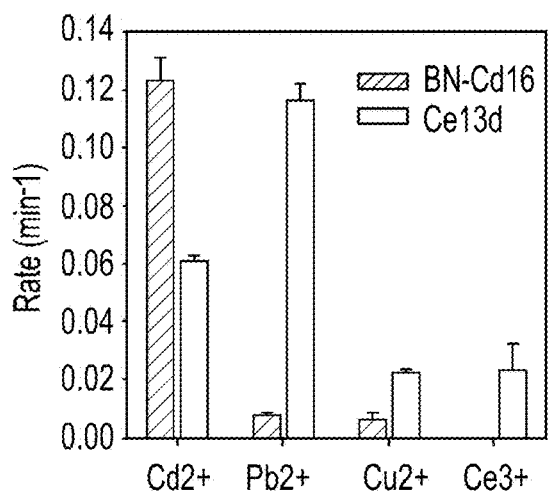

Next, the kinetics of BN-Cd16 was measured with the active metal ions, and a gel image with $Cd^{2+}$ is shown in FIG. 10B. The cleavage rate with 10 µM $Cd^{2+}$ is 0.12 $min^{-1}$, 15-fold higher than that with $Cu^{2+}$ and 20-fold higher than $Pb^{2+}$ (FIG. 10D, black bars). $Hg^{2+}$ produced an interesting cleavage kinetic profile, showing ~8% cleavage only in the first half minute. $Hg^{2+}$ can cleave PS RNA even in the absence of any DNAzyme due to its extremely strong thiophilicity.

Figure 10E:
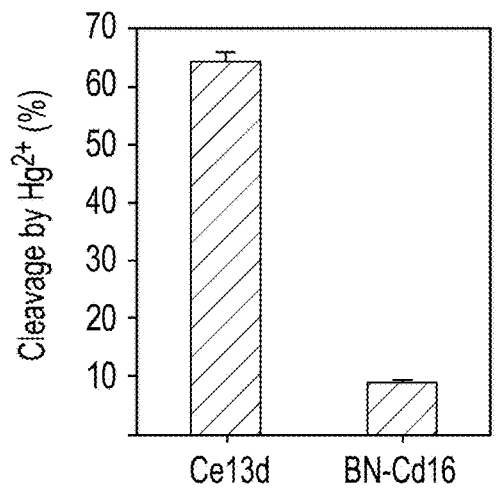
Figure 10F:
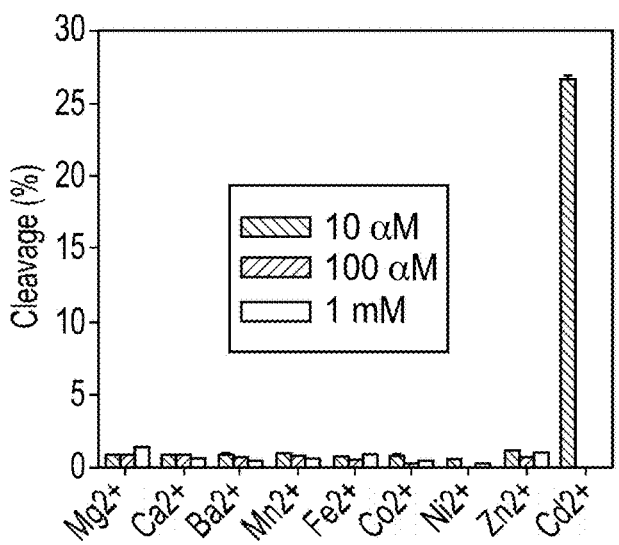
Figure 10G:
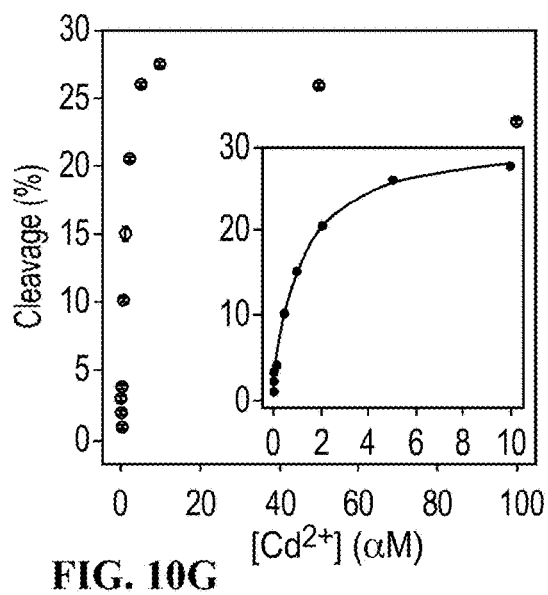

For comparison, the cleavage rate of Ce13 was measured (FIG. 10D, red bars), where all the four metals showed significant activity. Since the $Hg^{2+}$ rate cannot be accurately measured, the final cleavage yield is compared (FIG. 10E). Ce13 produced ~8-fold more cleavage. Taken together, BN-Cd16 is highly selective for $Cd^{2+}$ and it represents a significant improvement over Ce13. For practical $Cd^{2+}$ detection, there is likely to be low nM transition metals, where selectivity for $Cd^{2+}$ will be further improved. The effect of $Cd^{2+}$ concentration (FIG. 10G) on cleavage was also studied. The highest activity was observed with 10 µM $Cd^{2+}$; further increasing $Cd^{2+}$ reduced activity slightly. The apparent $K_d$ is estimated to be 1.2 µM $Cd^{2+}$ (inset of FIG. 10G).

In addition to this most abundant family, a few other sequences were also tested. For example, BN-Cd13 (three similar sequences found in the library) is quite active (Figure S5A), but not selective (Figure S5B). BN-Cd04 has very low activity (Figure S5A). BN-Cd18 has poor selectivity (Figure S6). BN-Cd40 is quite selective (Figure S6) but very slow (Figure S7). Overall, BN-Cd16 is an optimal sequence both in terms of activity and specificity for $Cd^{2+}$.

Stereochemistry.

For all these assays, $Cd^{2+}$ cleaved about 35% of the substrate. This could be increased somewhat by increasing enzyme concentration and reaction time, to result in cleavage closer to but less than 50%.

Introducing a PS modification results in two diastereomers at the phosphorus center ($R_p$ and $S_p$, FIG. 11A). Most enzymes use $Mg^{2+}$, which likes oxygen-based ligands. When the pro-$R_p$ oxygen was replaced by sulfur, the $Mg^{2+}$-dependent activity was nearly abolished (>100-fold slower). This activity can often be rescued by thiophilic metals such as $Cd^{2+}$ or $Mn^{2+}$. When the pro-$S_p$ oxygen was replaced, the effect was much smaller (e.g. ~5-fold). This indicates that these enzymes use the pro-$R_p$ oxygen to bind $Mg^{2+}$.

During in vitro selection and assays, these two isomers were not separated. It is likely that only one isomer is active. To test each diastereomer separately, the 5'-half of the substrate containing the PS center was separated and then ligated to the other half of the substrate bearing a 5'-phosphate and 3'-FAM (FIG. 11B). HPLC separation of the isomers shows two well resolved peaks (FIG. 11C). It is known that the $R_p$ form is eluted first followed by the $S_p$. These substrate diastereomers were then separately hybridized with the BN-Cd16 DNAzyme and their activities in the presence of $Cd^{2+}$ were measured (FIG. 11D). The $R_p$ substrate exhibits a rate of 0.15 $min^{-1}$, while the $S_p$ substrate exhibits a rate of about 0.0013 $min^{-1}$. Therefore, the $R_p$ form is ~100-fold faster than the $S_p$ form. The fact that these two isomers have different reaction rates supports that cleavage reaction takes place at the rA*G site.

DNAzyme-Based Chiral Separation.

Figure 12A:
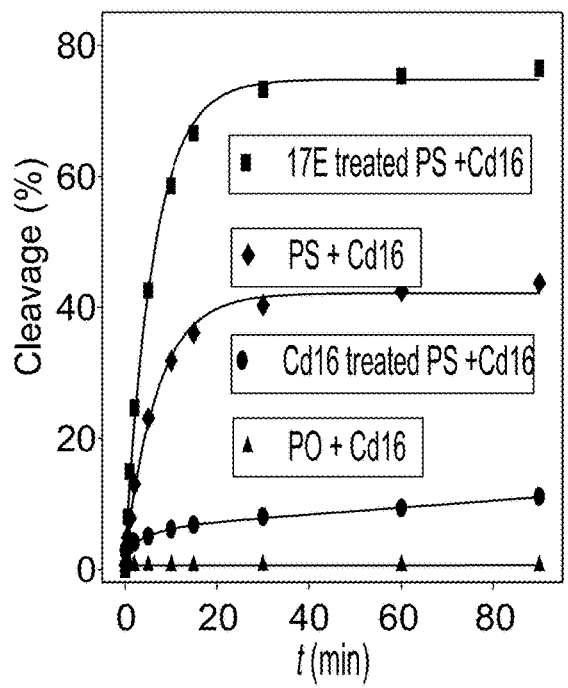
FIG. 12 illustrates the kinetics of PO, PS, and treated PS substrate cleavage by (A) the BN-Cd16 DNAzyme in the presence of 10 µM $Cd^{2+}$, or by (B) the 17E DNAzyme in the presence of 10 mM $Mg^{2+}$; and (C) the scheme of experiment design for treating the PS substrate to remove the $S_p$ population by the 17E DNAzyme and to increase reaction yield.
Figure 12B:
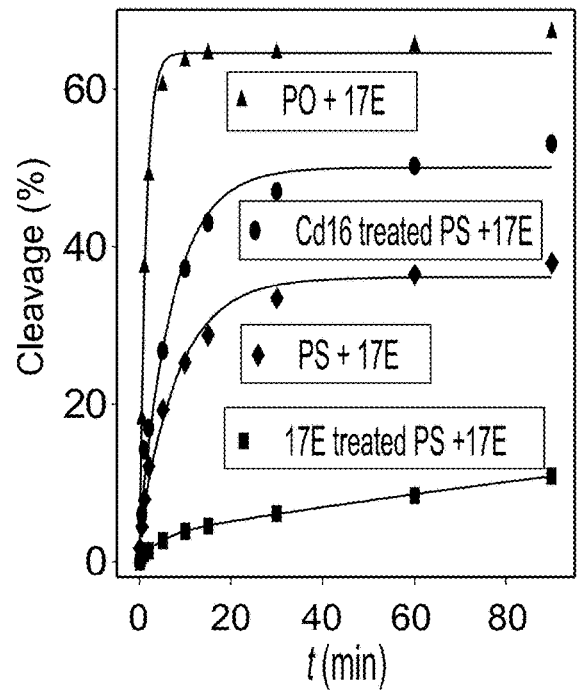

The above method requires both HPLC purification and a ligation step, limiting the yield of products. A DNAzyme-based method for chiral separation was developed. 17E is a well-characterized and $Mg^{2+}$-dependent DNAzyme. Since 17E shares the same substrate sequence as the current BN-Cd16 DNAzyme, the PS substrate used herein was reacted with 17E in the presence of 10 mM $Mg^{2+}$. In 90 min, ~40% cleavage was achieved (FIG. 12B, rate=0.12 $min^{-1}$). For comparison, the normal PO substrate was determined to have a rate of 0.76 $min^{-1}$ (FIG. 12B). This ~6-fold rate difference reflects a typical thio effect. The uncleaved PS substrate (after the 17E treatment) was isolated after gel electrophoresis and hybridized with the BN-Cd16 DNAzyme. Upon adding $Cd^{2+}$, ~80% cleavage was achieved (FIG. 12A), which is significantly higher than the untreated PS substrate (FIG. 12A). The rate of cleavage (0.16 $min^{-1}$) was similar to that of the untreated substrate (0.12 $min^{-1}$), and also similar to the above purified $R_p$ form. Therefore, the same species is responsible for the cleavage before and after the 17E DNAzyme treatment. When the 17E treated substrate was reacted with 17E again, only ~10% cleavage was observed (FIG. 12B). This result implies that the 17E treatment selectively removed one of the isomers, and this was determined to be the $S_p$ isomer.

The remaining isomer active with BN-Cd16/$Cd^{2+}$ was thus enriched. This study exemplifies the use of nucleic acid-based enzymes for chiral separation.

Figure 12C:
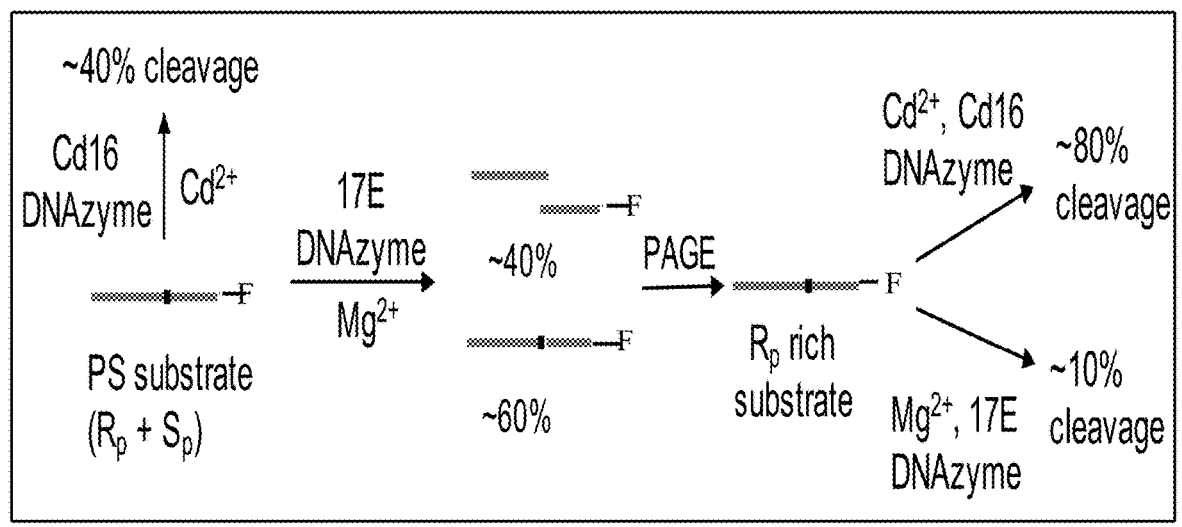

The 10-23 DNAzyme is a similar $Mg^{2+}$-dependent DNAzyme that was selected together with 17E (as described in Santoro and Joyce (1997). *Proc. Natl. Acad. Sci. U.S.A.,* 94, 4262-4266). The 10-23 DNAzyme uses the pro-$R_p$ oxygen to bind $Mg^{2+}$. Since the 10-23 DNAzyme is a variant of 17E, it is expected also to use the same R-isomer. In fact, all known RNA-cleaving ribozymes use the pro-$R_p$ oxygen to bind $Mg^{2+}$. Based on the results, BN-Cd16 uses the $R_p$ sulfur to bind $Cd^{2+}$. Once the $S_p$ population is removed by 17E, the remaining $R_p$ rich population is all active with BN-Cd16 (FIG. 12C). This is the first time that a DNAzyme has been used to achieve chiral separation. In preparing this sensor (vide infra), 3 nmol substrate were purified in one run, which can be readily scaled up.

To further confirm this, the PS substrate was treated with BN-Cd16 and 10 μM $Cd^{2+}$. This treatment should remove most of the $R_p$ isomer. The remaining uncleaved $S_p$ rich substrate should be less active with BN-Cd16. This was indeed true (FIG. 12A), yielding only ~10% cleavage. In a separate experiment, the activity of the PO substrate with BN-Cd16 and $Cd^{2+}$ (FIG. 12A) was measured, where no cleavage was observed. This highlights the importance of the PS. In fact, BN-Cd16 cannot cleave the PO substrate by any tested metals, which also explains its high metal specificity (e.g. strong oxygen effect).

$Cd^{2+}$ Turning Over.

Since $Cd^{2+}$ has relatively strong affinity with sulfur, one question is whether $Cd^{2+}$ can turnover multiple DNAzymes or is it sequestered after each reaction. To test this, 5 μM DNAzyme complex and 0.2 μM $Cd^{2+}$ was used. The cleavage fraction was quantified in terms of turnover number, and multiple turnover is indeed possible. Each turnover takes ~50 min, and can be accelerated by using more $Cd^{2+}$. This might be useful for improving sensitivity for detecting $Cd^{2+}$.

A $Cd^{2+}$ Sensing Beacon.

Figure 13A:
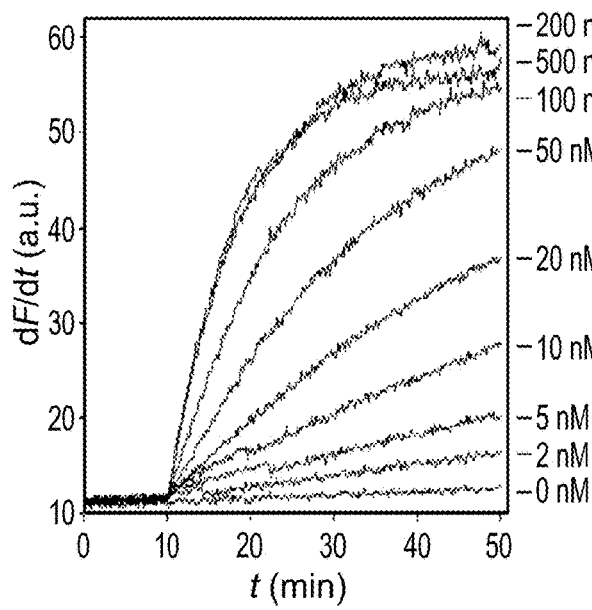
FIG. 13 illustrates (A) kinetics of sensor fluorescence enhancement with various concentrations of $Cd^{2+}$. The arrowhead points the time of $Cd^{2+}$ addition; (B) initial rate of fluorescence enhancement (from 1 to 10 min after adding $Cd^{2+}$) as a function of $Cd^{2+}$ concentration. Inset: the linear response at low $Cd^{2+}$ concentrations; (C) sensor response to 100 nM of various metals (shown on (D); and (D) sensor selectivity quantified at two metal concentrations. Inset: a scheme showing the sensor design.
Figure 13B:
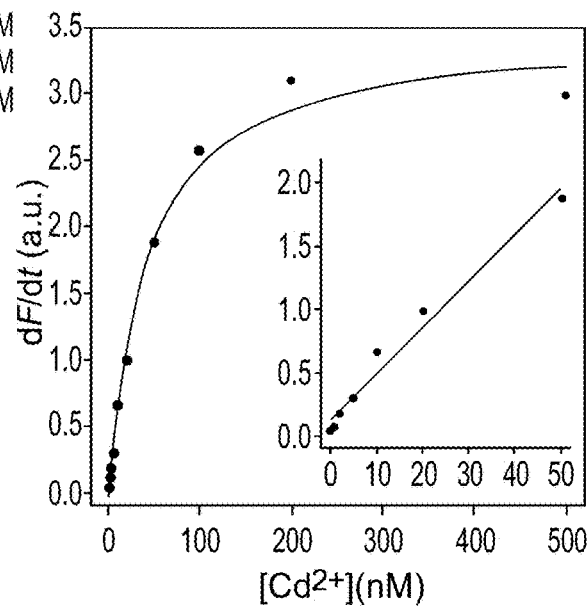
Figure 13C:
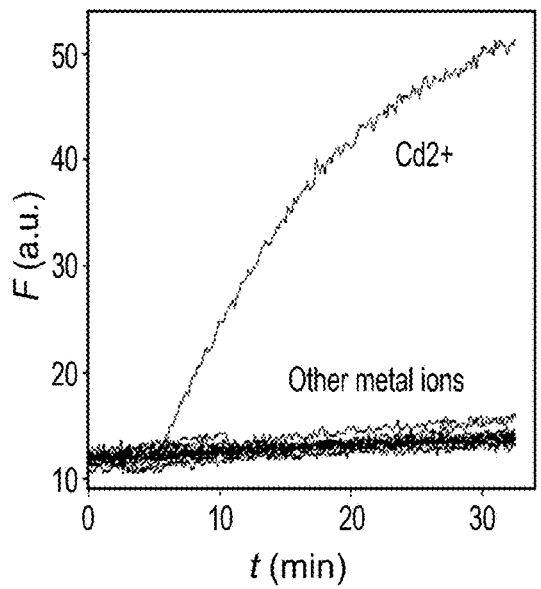
Figure 13D:
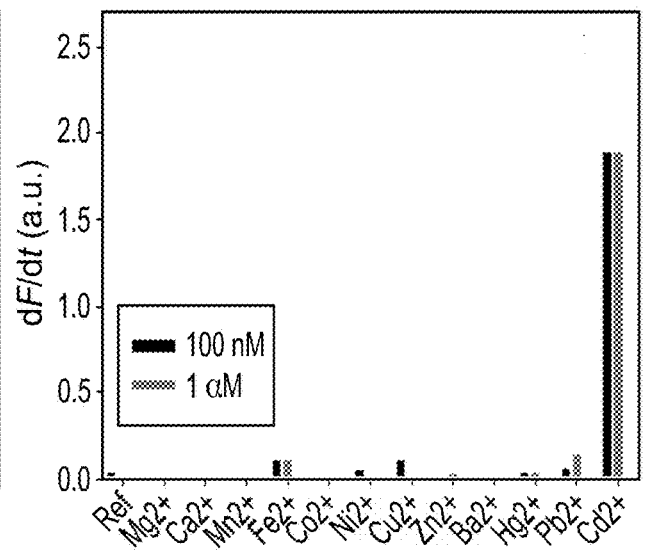

To test Cd16 DNAzyme for $Cd^{2+}$ detection, a biosensor was designed. The 5'-end of the substrate was labeled with a FAM fluorophore and the 3'-end of the enzyme was labeled with a dark quencher (inset of FIG. 13D). In the hybridized complex, the fluorescence was quenched. When $Cd^{2+}$ was added, a concentration dependent fluorescence enhancement was observed (FIG. 13A). At high $Cd^{2+}$ concentrations, most fluorescence increase took place in the first few minutes. The slope of these kinetic traces were measured from minute 1 to 10 after adding $Cd^{2+}$ (FIG. 13B). The data in the first minute were filtered to eliminate potential $Hg^{2+}$ interference. The detection limit was 1.1 nM $Cd^{2+}$ based on 3σ/slope calculation (inset). The EPA maximal contamination level in drinking water is 5 μg/L (45 nM) $Cd^{2+}$, which is right in the middle of the present dynamic range.

The sensor response to other metal ions was then measured (FIG. 13C, D), and only $Cd^{2+}$ showed an obvious signal increase. To improve sensitivity, the substrate was first treated with 17E to remove the $S_p$ population. Without the 17E treatment, the amount of fluorescence enhancement was ~40% lower.

Detecting $Cd^{2+}$ in Rice.

Figure 14A:
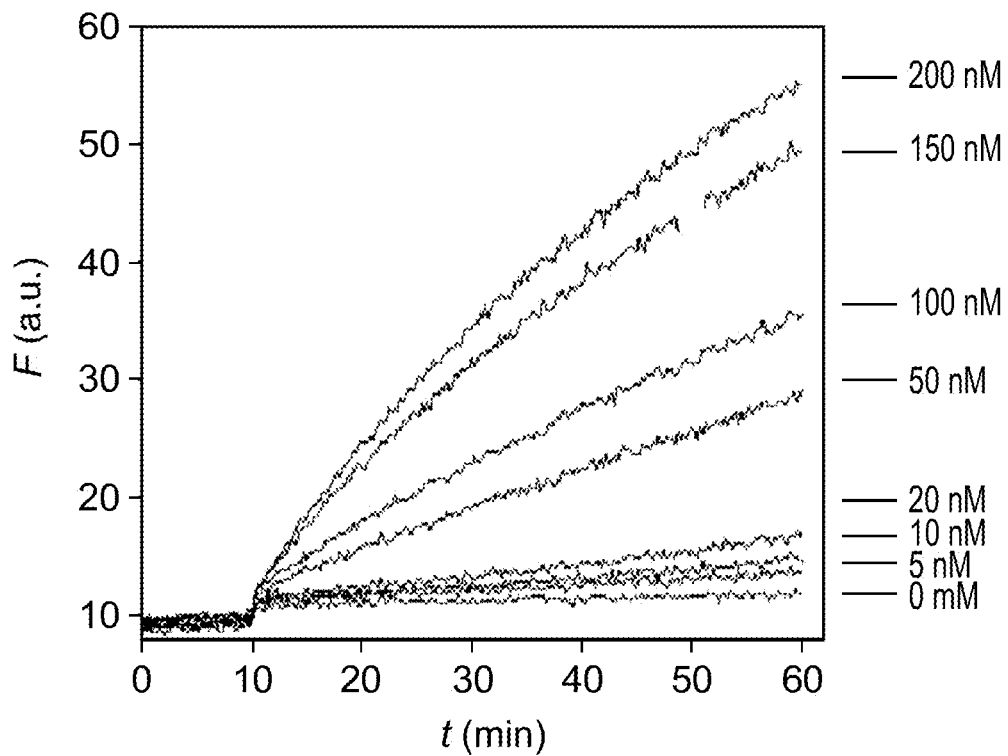
FIG. 14 illustrates use of a DNAzyme for sensing Cd in rice, including (A) the sensor response kinetics to various concentrations of $Cd^{2+}$ in rice extracts added at 10 min; and (B) the slope of sensor signal increase as a function of $Cd^{2+}$ concentration.
Figure 14B:
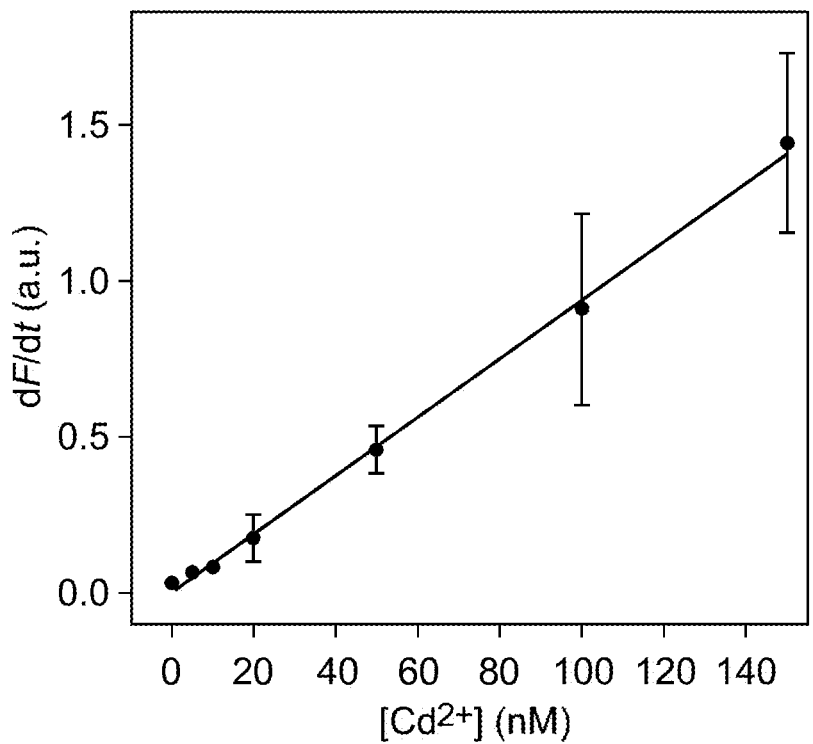

To confirm the use of the present sensor, a rice sample containing cadmium was used. The World Health Organization (WHO) has set the limit of $Cd^{2+}$ to be 0.4 mg/kg polished rice grain (i.e. 0.4 ppm). Ground rice powder was digested with hydrochloric acid under heating at 95° C. for 3 hours. The digested sample was neutralized with NaOH base and then diluted 50 times into the sensor solution (1 mM HEPES, pH 7.5). The $Cd^{2+}$ concentration was determined to be 17.8 nM at the toxic limit. The kinetics of the sensor response was monitored (FIG. 14A), and the detection limit was determined to be 1.6 nM $Cd^{2+}$, which is >10-fold lower than the WHO limit. This proof-of-concept experiment supports the feasibility of using this sensor for an aqueous rice extract.

References referred to herein are incorporated by reference.

The invention claimed is:

1. A substrate-bound DNAzyme complex comprising a DNAzyme bound to a nucleic acid-based substrate, wherein:
   i) the DNAzyme comprises a pair of binding arms which hybridize to binding regions on the nucleic acid-based substrate, and a catalytic domain between the binding arms which catalyzes cleavage of the nucleic acid-based substrate, wherein the nucleotide sequence of the catalytic domain is selected from the nucleotide sequence of the catalytic domain of a DNAzyme selected from the group consisting of Ce13d, Lu12, Tm7, 17E, 10-23, 39E, GR5 and Cd16, and
   ii) the nucleic acid-based substrate comprises a phosphorothioate-modified ribonucleotide DNAzyme cleavage site between the binding regions, wherein the catalytic domain of the DNAzyme catalyzes cleavage of the phosphorothioate-modified ribonucleotide cleavage site in the presence of a thiophilic metal.

2. The DNAzyme complex of claim 1, wherein the binding arms of the DNAzyme comprise from 5 to 20 nucleotides.

3. The DNAzyme complex of claim 1, wherein the nucleotide sequence of the binding arms of the DNAzyme is selected from the nucleotide sequence of the binding arms of Ce13d, Lu12, Tm7, 17E, 10-23, 39E, Cd16 or GR5, wherein the nucleotide sequence of the binding arms and the catalytic domain are from the same DNAzyme.

4. The DNAzyme complex of claim 1, wherein the substrate has the sequence, 5' GTCACGAGTCACTATrAG-GAAGATGGCGAAA3' (SEQ ID NO: 2).

5. A thiophilic metal-detecting DNAzyme array comprising at least two different DNAzyme complexes as defined in claim 1.

6. A method of detecting the presence of a thiophilic metal in a sample, comprising:
   i) incubating the sample with a substrate-bound DNAzyme complex comprising a DNAzyme bound to a labelled nucleic acid-based substrate, wherein the DNAzyme comprises a pair of binding arms which hybridize to binding regions on the nucleic acid-based substrate, and a catalytic domain between the binding arms which catalyzes cleavage of the nucleic acid-based substrate, wherein the nucleotide sequence of the catalytic domain is selected from the nucleotide sequence of the catalytic domain of a DNAzyme selected from the group consisting of Ce13d, Lu12, Tm7, 17E, 10-23, 39E, GR5 and Cd16, and the labelled nucleic acid-based substrate comprises a phosphorothioate-modified ribonucleotide DNAzyme cleavage site between the binding regions, wherein the catalytic domain of the DNAzyme catalyzes cleavage of the phosphorothioate-modified ribonucleotide substrate cleavage site in the presence of a thiophilic metal to release a labelled substrate cleavage product from the DNAzyme complex;
   ii) conducting a separation step to separate labelled substrate cleavage product from the DNAzyme; and
   iii) detecting the presence of the metal in the sample by detecting labelled substrate cleavage product.

7. The method of claim 6, wherein the metal is selected from the group consisting of mercury, lead, copper, thallium, silver and cadmium.

8. The method of claim 6, wherein the sample is an aqueous sample incubated with 5 nM to 1 μM of the substrate-bound DNAzyme complex at room temperature and at a pH in the range of about 6-7.8.

9. The method of claim 8, wherein the nucleotide sequence of the binding arms of the DNAzyme is selected from the nucleotide sequence of binding arms of Ce13d, Lu12, Tm7, 17E, 10-23, 39E, Cd16 or GR5, wherein the nucleotide sequence of the binding arms and the catalytic domain are from the same DNAzyme.

10. The method of claim 6, wherein the DNAzyme is Ce13d.

11. The method of claim 6, wherein the substrate has the sequence, 5'GTCACGAGTCACTATrAGGAA-GATGGCGAAA3' (SEQ ID NO: 2).

12. The method of claim 6, wherein the DNAzyme comprises the sequence, 5'-TTT CGC CAT CTT CCT TCG ATA GTT AAA ATA GTG ACT CGT GAC-3' (SEQ ID NO: 37).

* * * * *